United States Patent
Palczewski et al.

(10) Patent No.: US 12,251,373 B2
(45) Date of Patent: *Mar. 18, 2025

(54) COMPOUNDS AND METHODS OF TREATING RETINAL DEGENERATION

(71) Applicants: CASE WESTERN RESERVE UNIVERSITY, Cleveland, OH (US); UNIVERSITY OF PITTSBURGH—OF THE COMMONWEALTH SYSTEM OF HIGHER EDUCATION, Pittsburgh, PA (US)

(72) Inventors: Krzysztof Palczewski, Ivrine, CA (US); Yuanyuan Chen, Pittsburgh, PA (US)

(73) Assignees: CASE WESTERN RESERVE UNIVERSITY, Cleveland, OH (US); UNIVERSITY OF PITTSBURGH—OF THE COMMONWEALTH SYSTEM OF HIGHER EDUCATION, Pittsburgh, PA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/461,023

(22) Filed: Sep. 5, 2023

(65) Prior Publication Data

US 2024/0041847 A1 Feb. 8, 2024

Related U.S. Application Data

(63) Continuation of application No. 17/544,454, filed on Dec. 7, 2021, now Pat. No. 11,744,826, which is a continuation of application No. 16/609,162, filed as application No. PCT/US2018/030251 on Apr. 30, 2018, now Pat. No. 11,191,752.

(60) Provisional application No. 62/645,576, filed on Mar. 20, 2018, provisional application No. 62/491,811, filed on Apr. 28, 2017.

(51) Int. Cl.
| | |
|---|---|
| *A61K 31/4402* | (2006.01) |
| *A61K 31/365* | (2006.01) |
| *A61K 31/381* | (2006.01) |
| *A61P 29/00* | (2006.01) |

(52) U.S. Cl.
CPC ........ *A61K 31/4402* (2013.01); *A61K 31/365* (2013.01); *A61K 31/381* (2013.01); *A61P 29/00* (2018.01)

(58) Field of Classification Search
CPC .. A61P 29/00; A61K 31/4402; A61K 365/381
See application file for complete search history.

(56) References Cited

U.S. PATENT DOCUMENTS

| | | | | |
|---|---|---|---|---|
| 1,191,752 | A * | 7/1916 | Walsh et al. | F27B 1/08 |
| | | | | 432/101 |
| 7,012,094 | B1 | 3/2006 | Bertenshaw et al. | |
| 11,191,752 | B2 * | 12/2021 | Palczewski | A61P 29/00 |
| 11,744,826 | B2 * | 9/2023 | Palczewski | A61P 29/00 |
| | | | | 514/357 |
| 2002/0032230 | A1 | 3/2002 | Pal et al. | |
| 2014/0235562 | A1 | 8/2014 | Palczewski et al. | |

OTHER PUBLICATIONS

Behnen et al. "A Small Chaperone Improves Folding and Routing of Rhodopsin Mutants Linked to Inherited Blindness," iScience, Jun. 29, 2018 (Jun. 29, 2018), vol. 4, pp. 1-19.

Chen et al. "A novel small molecule chaperone of rod opsin and its potential therapy for retinal degeneration," Nature Communications, May 17, 2018 (May 17, 2018), vol. 9, No. 1976, pp. 1-18.

Chen et al. "Transcriptome Profiling of NIH3T3 Cell Lines Expressing Opsin and the P23H Opsin Mutant Identifies Candidate Drugs for the Treatment of Retinitis Pigmentosa," Pharmacol Res, Nov. 9, 2016 (Nov. 9, 2016), vol. 115, pp. 1-13.

Herrera-Hernandez et al. "Flavonoid allosteric modulation of mutated visual rhodopsin associated with retinitis pigmentosa," Scientific Reports, Sep. 11, 2017 (Sep. 11, 2017), vol. 7, No. 11167, pp. 1-13.

Noorwez et al. "Pharmacological Chaperone-mediated in Vivo Folding and Stabilization of the P23H-opsin Mutant Associated with Autosomal Dominant Retinitis Pigmentosa," The Journal of Biological Chemistry, Apr. 18, 2003 (Apr. 18, 2003), vol. 278, No. 16, pp. 14442-14450.

* cited by examiner

*Primary Examiner* — D Margaret M Seaman
(74) *Attorney, Agent, or Firm* — Tarolli, Sundheim, Covell & Tummino LLP

(57) ABSTRACT

A method of treating retinal degeneration in a subject includes administering to the subject a therapeutically effective amount of a compound of formula (I).

5 Claims, 14 Drawing Sheets

Specification includes a Sequence Listing.

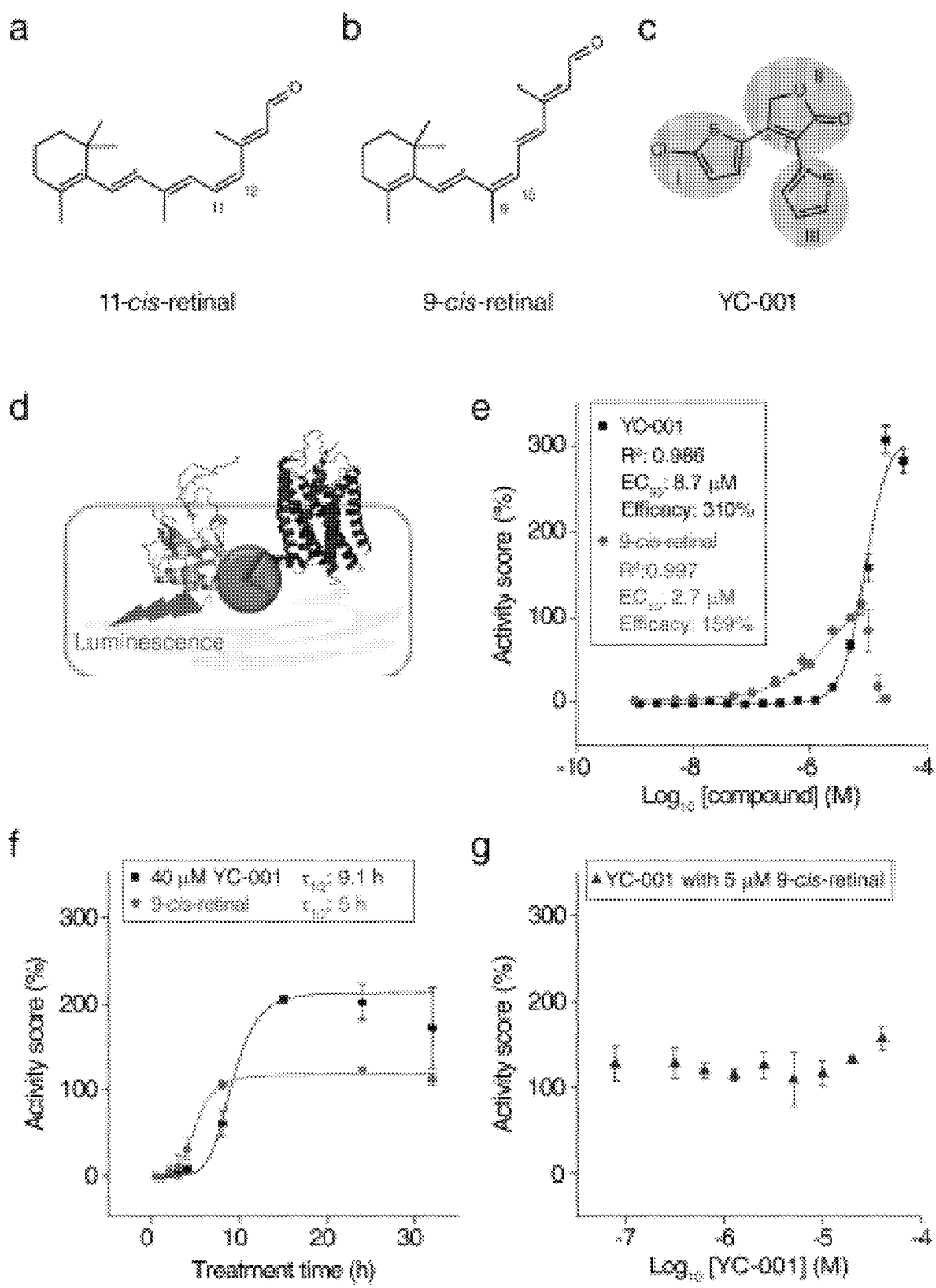
Figs. 1A-G

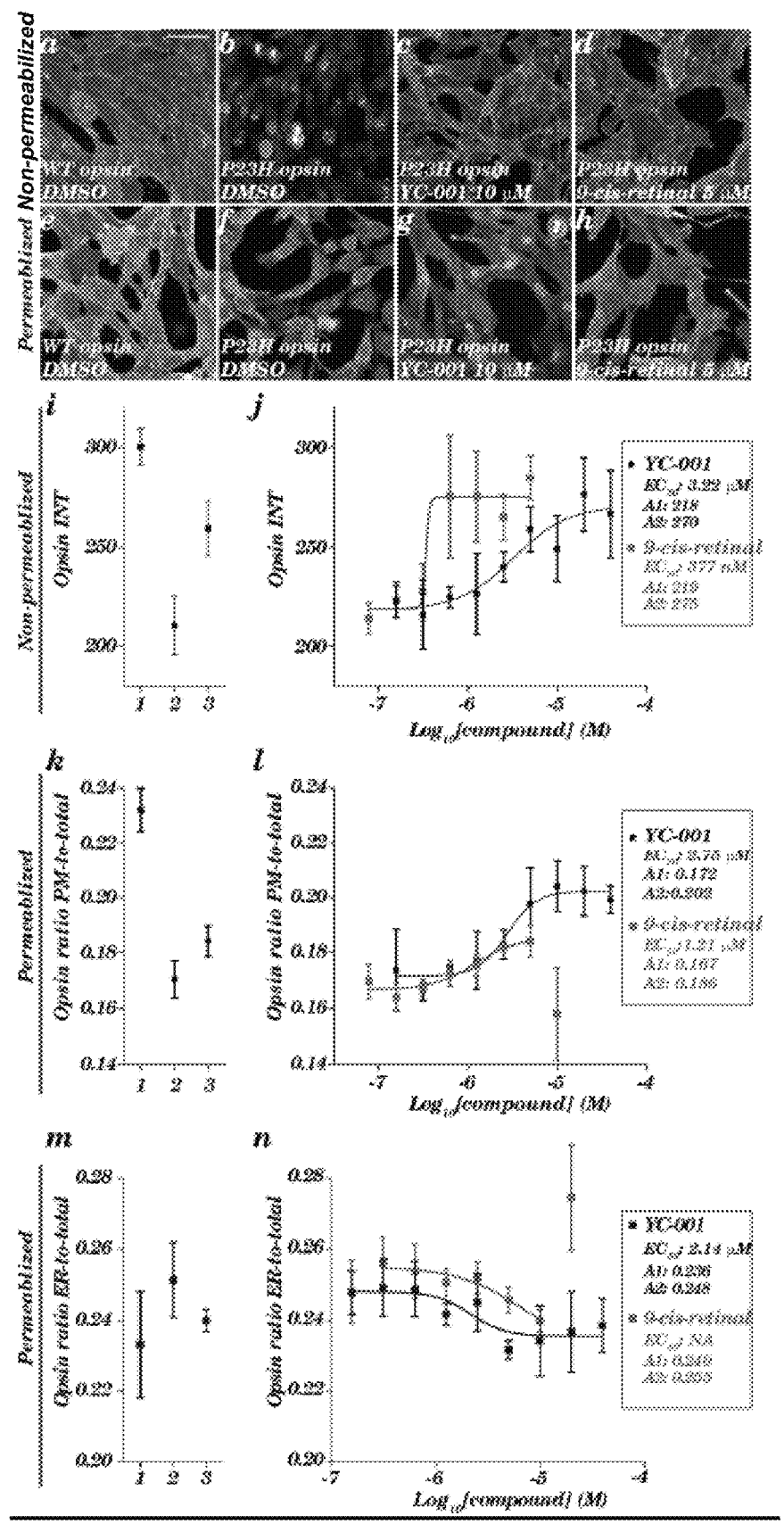
Figs. 2A-N

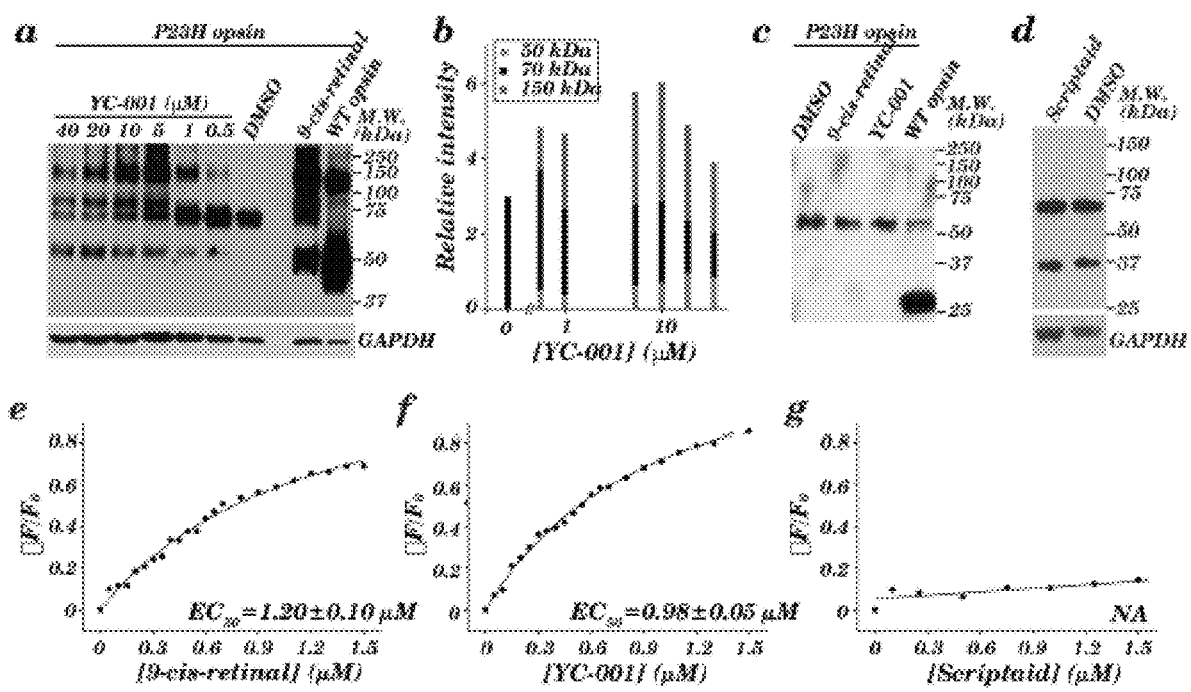
Figs. 3A-G

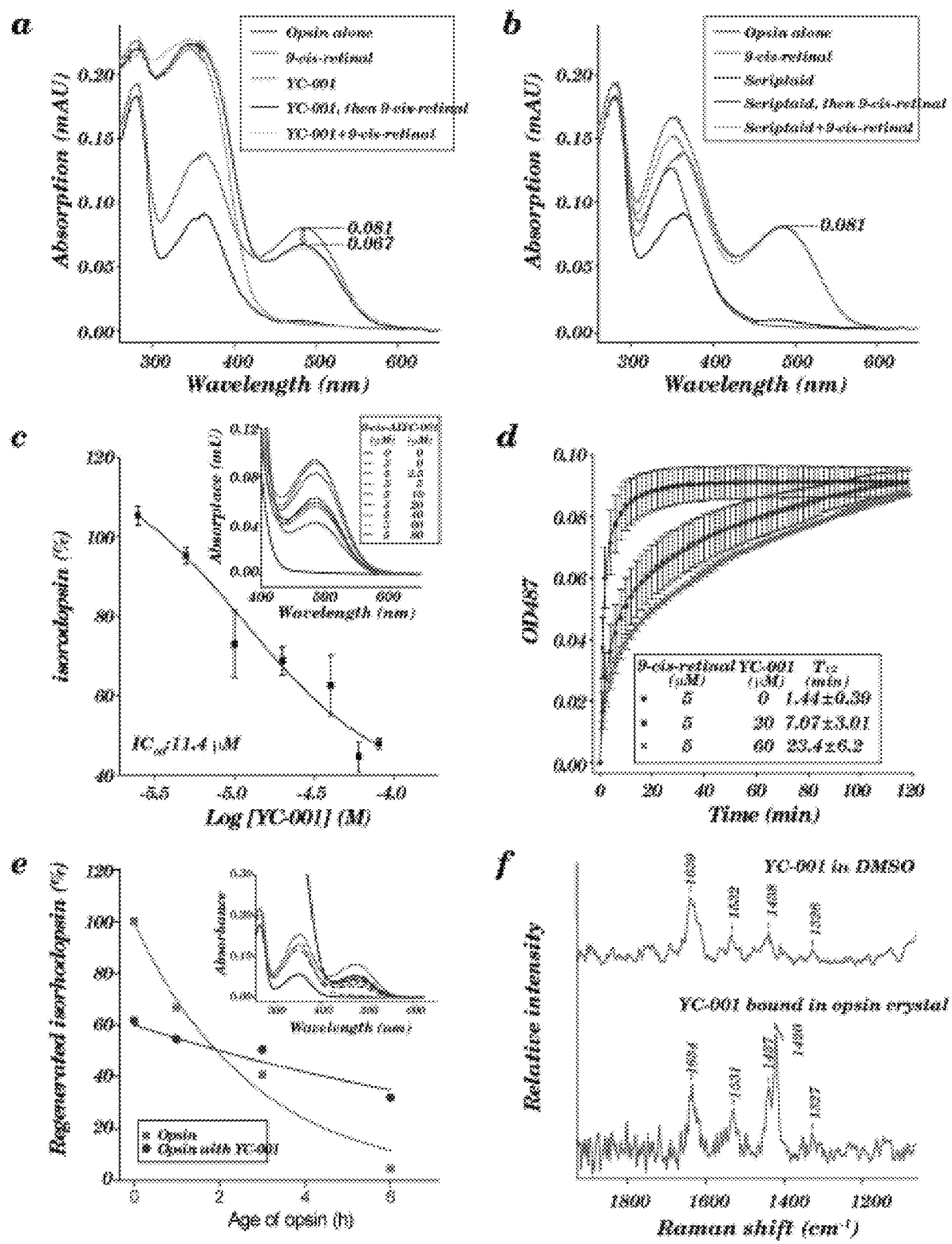
Figs. 4A-F

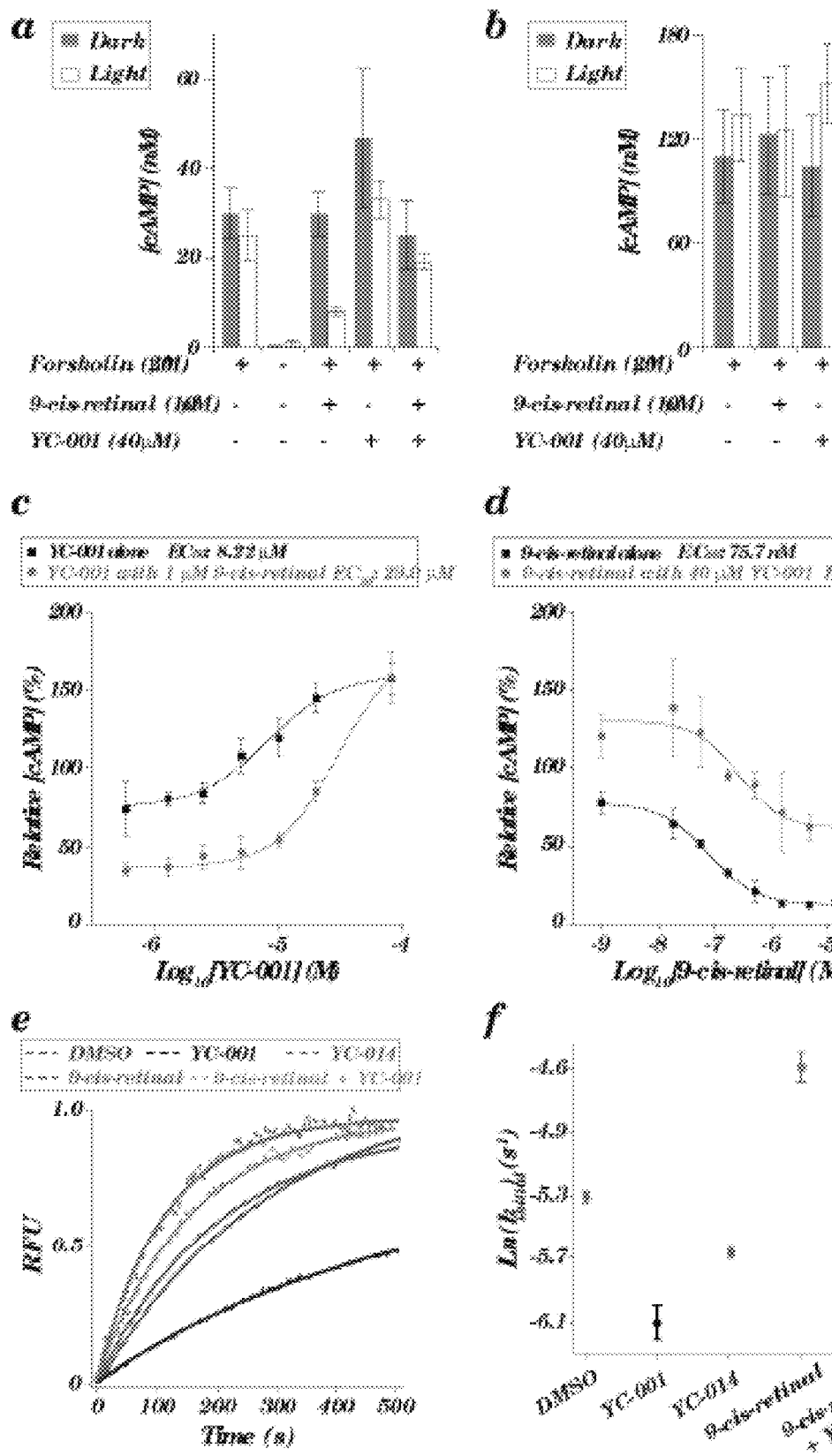
Figs. 5A-F

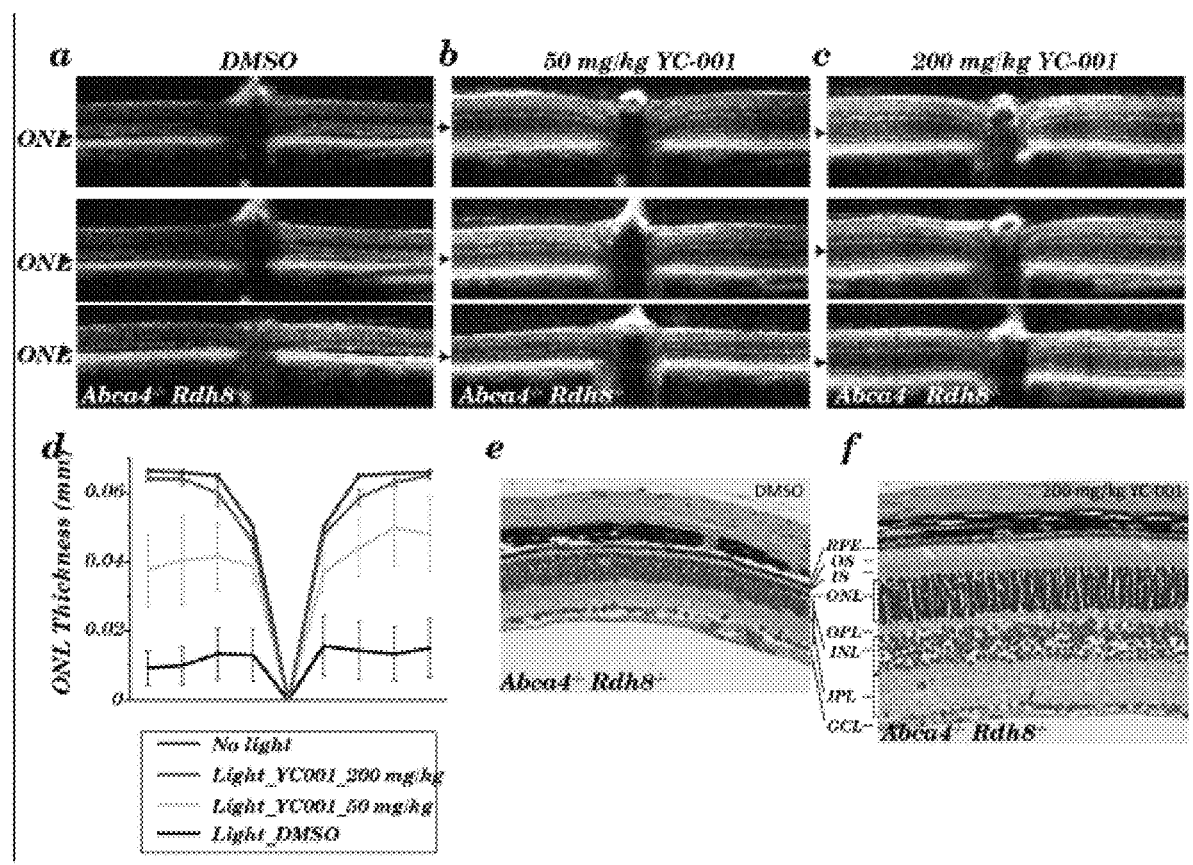
Figs. 6A-F

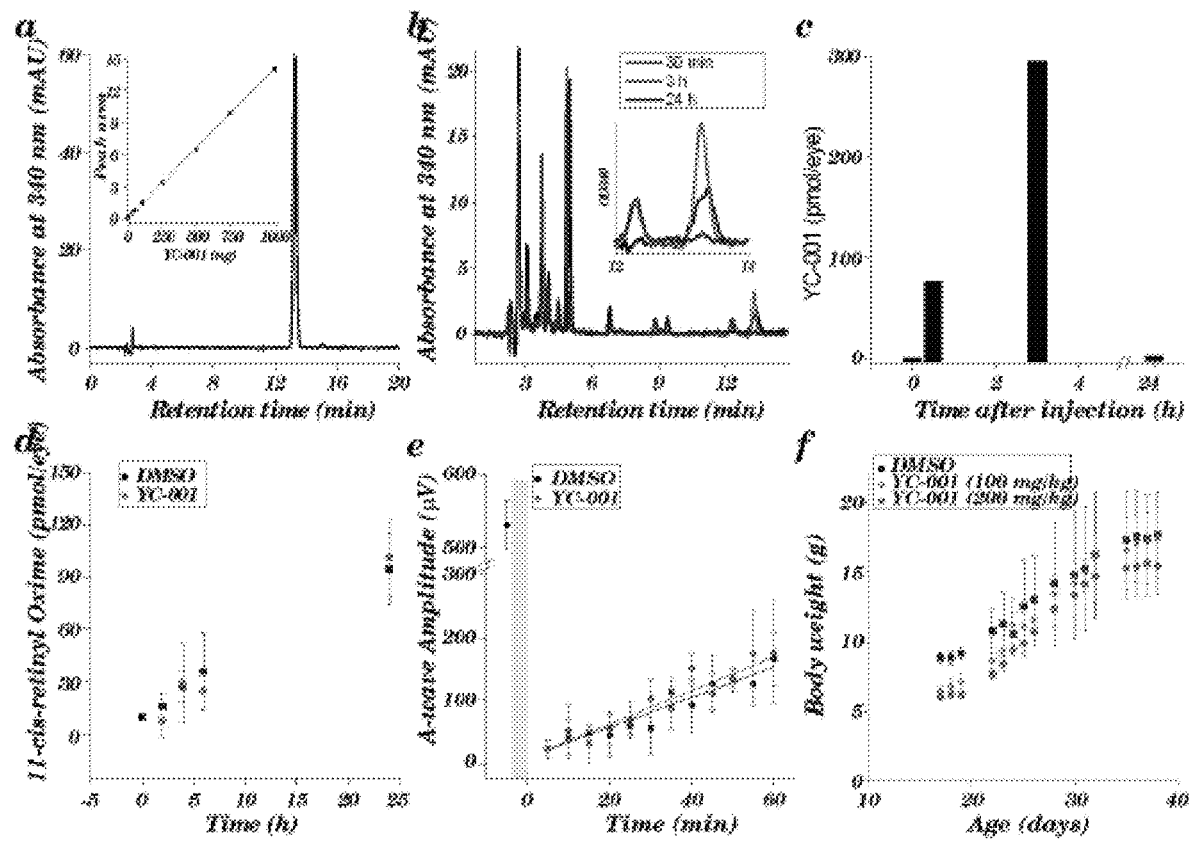
Figs. 7A-F

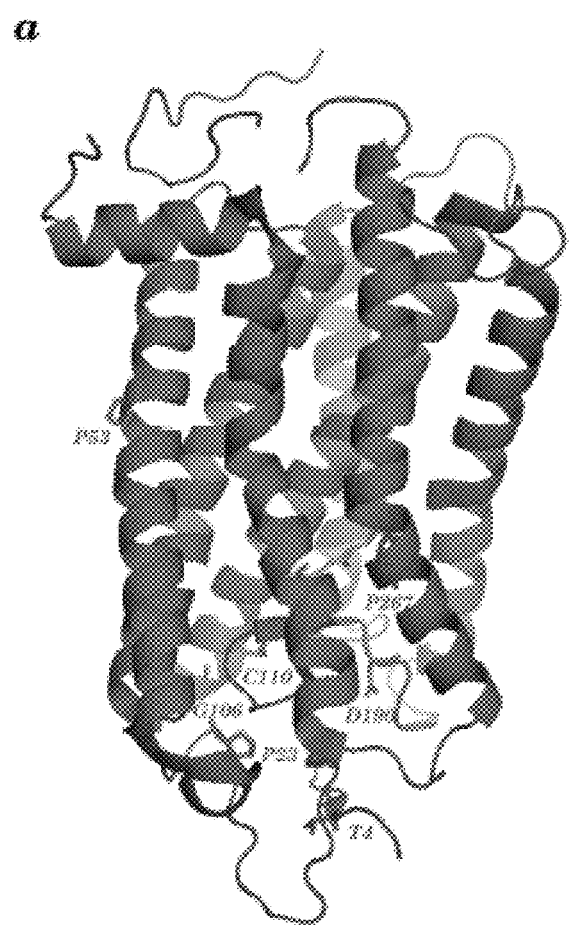 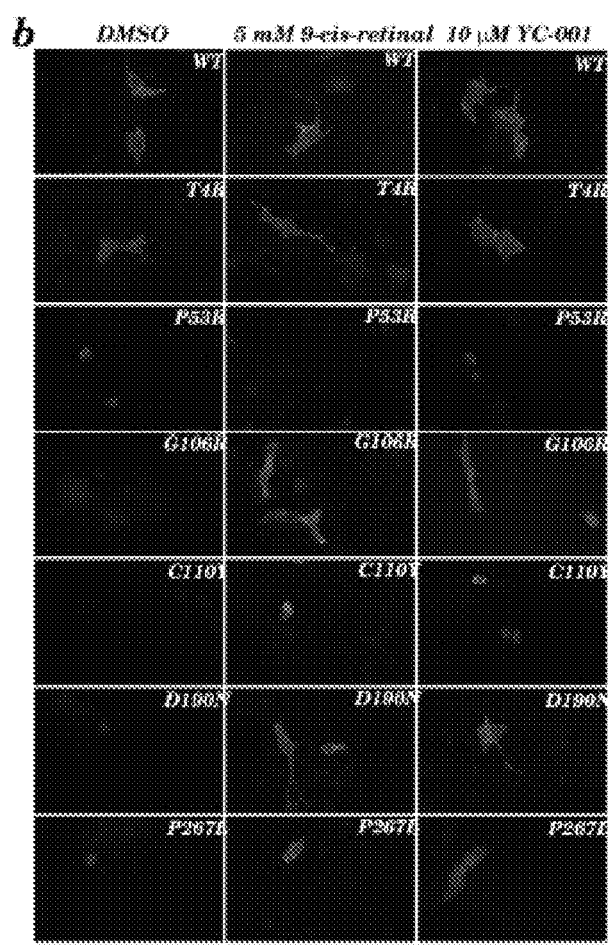
Figs. 8A-B

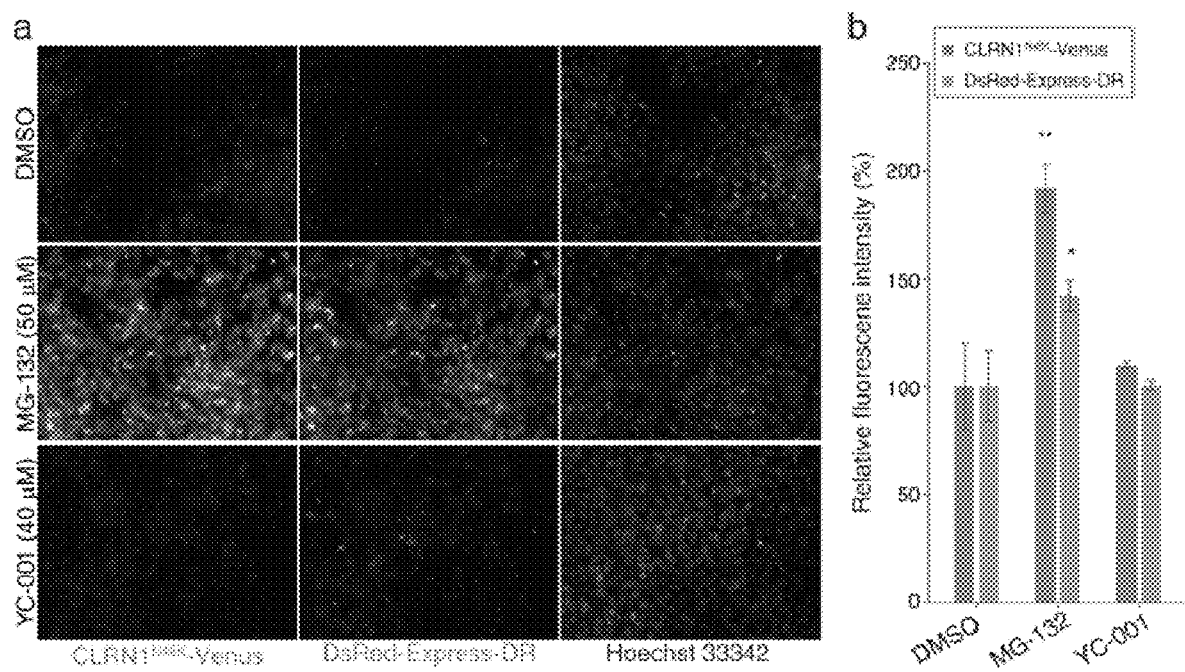
Figs. 9A-B
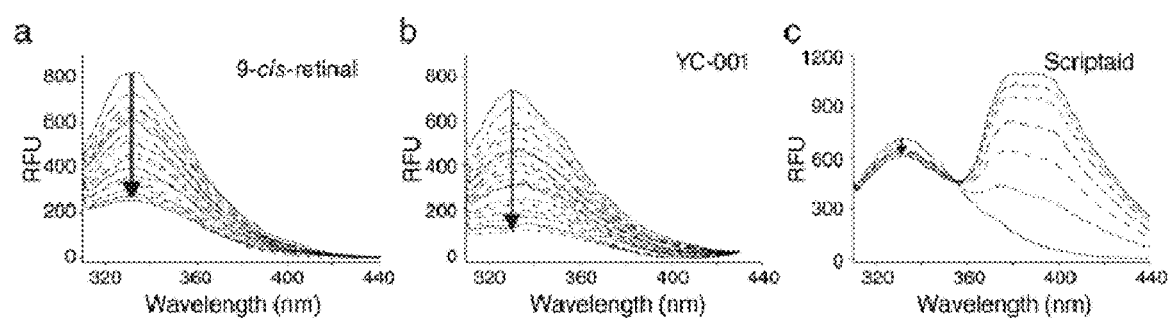
Figs. 10A-C

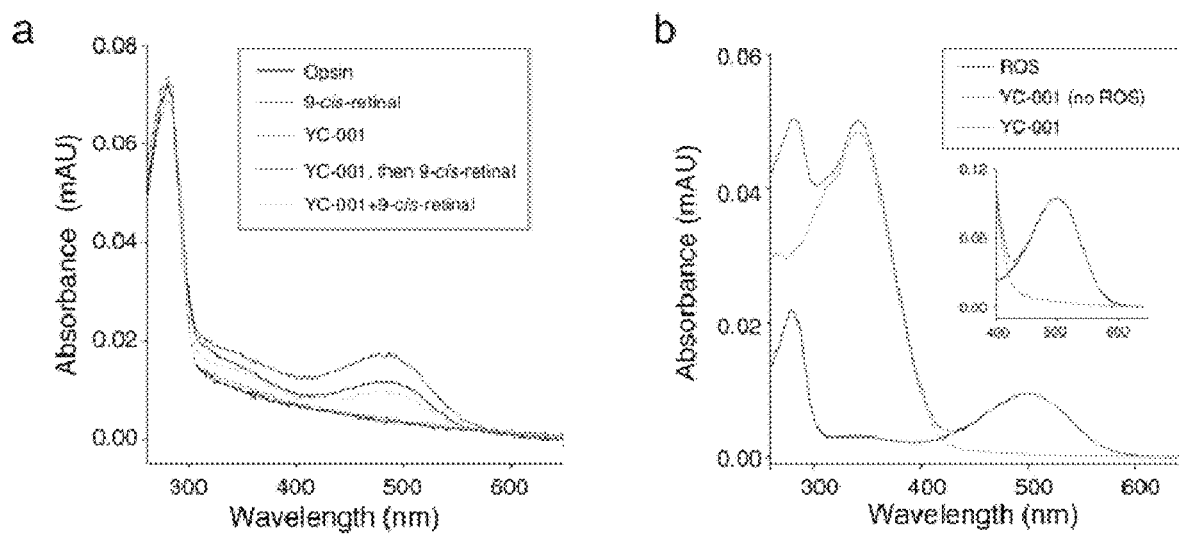
Figs. 11A-B
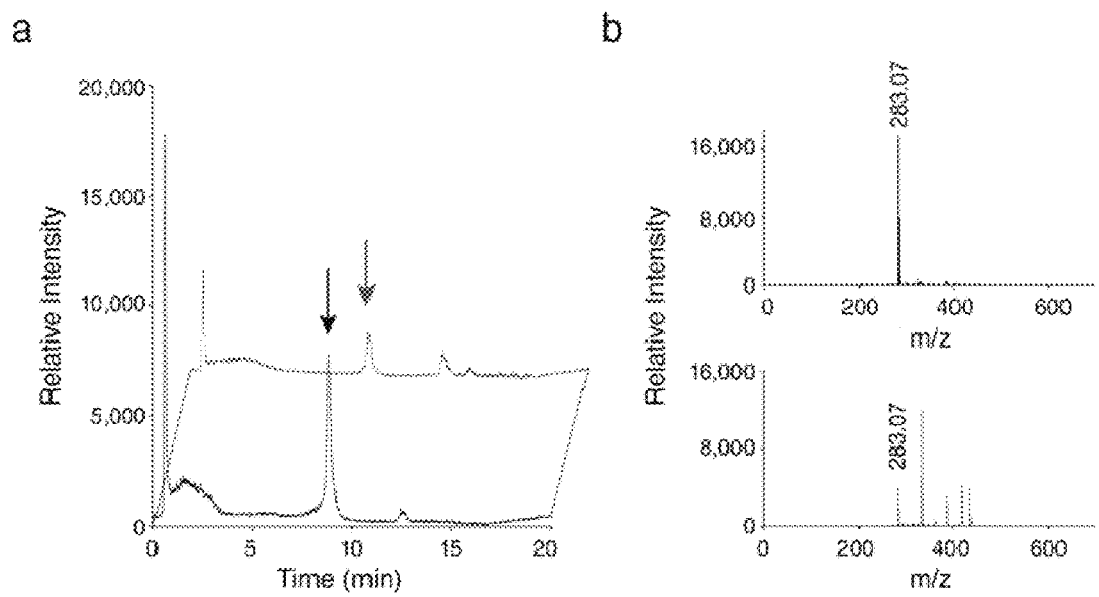
Figs. 12A-B

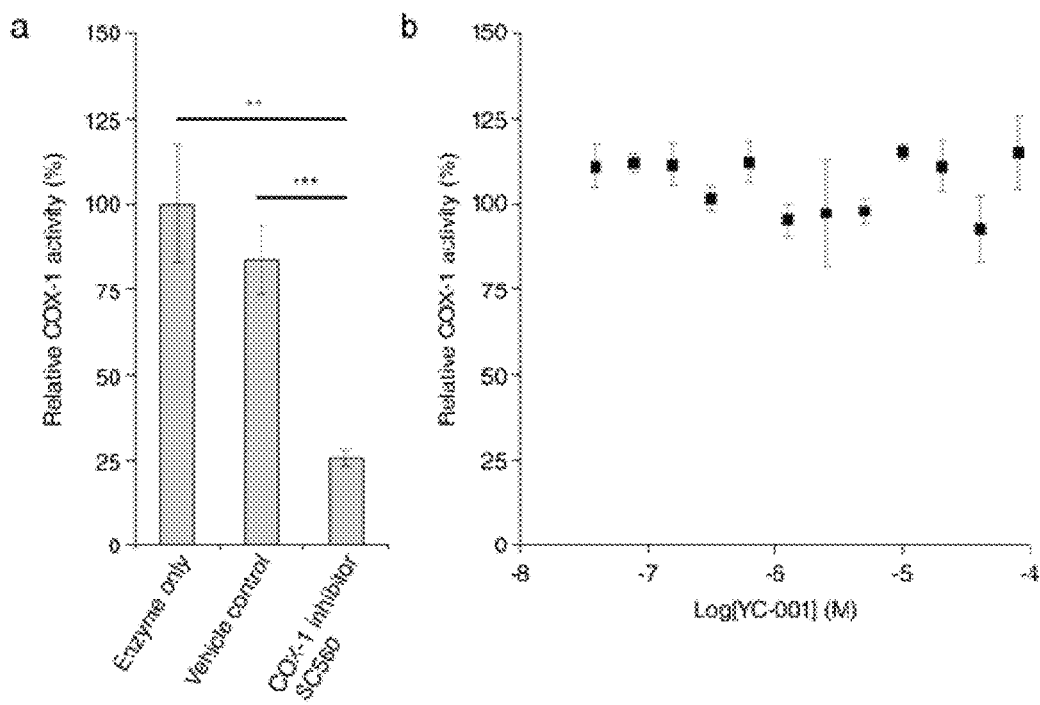
Figs. 13A-B
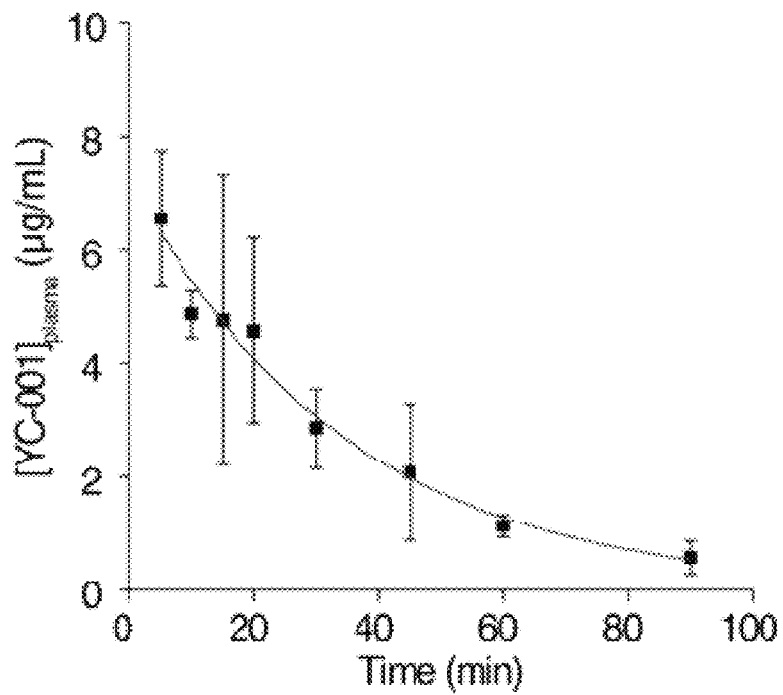
| Name (Unit) | Dose (mg/kg) | Route | n | $T_{1/2}$ (min) | $C_0$ (µg/mL) | $K_e$ (min⁻¹) | $V_d$ (L/kg) | Clearance (L/min/kg) |
|---|---|---|---|---|---|---|---|---|
| Value | 200 | i.p. | 32 | 34.5 | 7.28 | 0.0201 | 27.5 | 0.552 |
Fig. 14

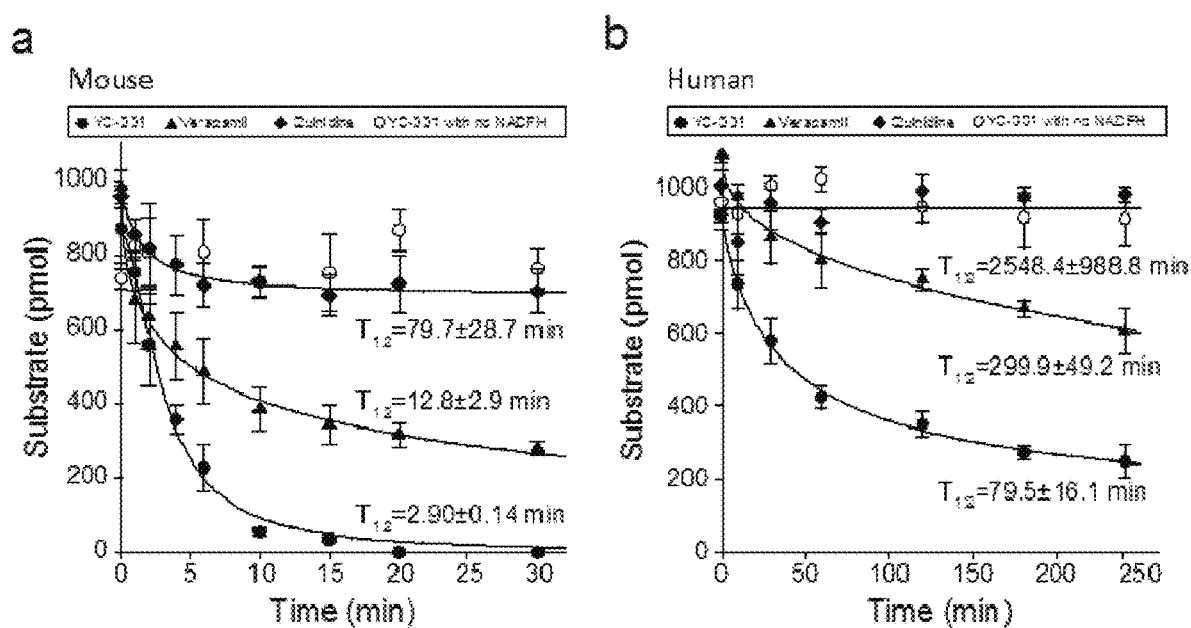
Figs. 15A-B

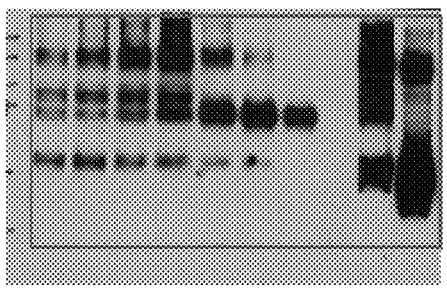
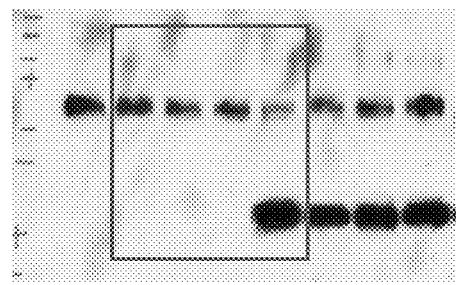
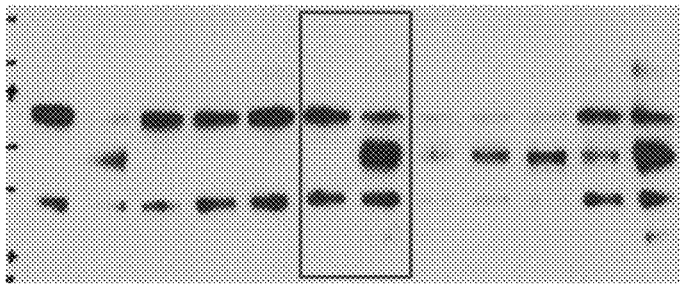
Figs. 16A-C a
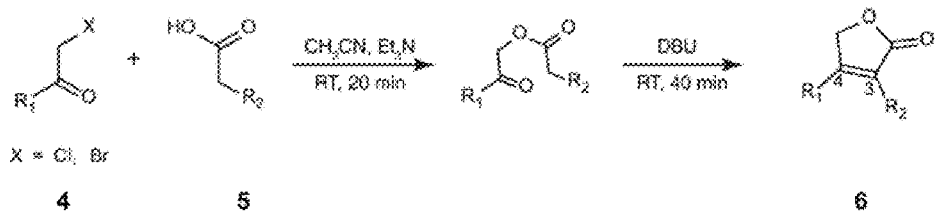
b
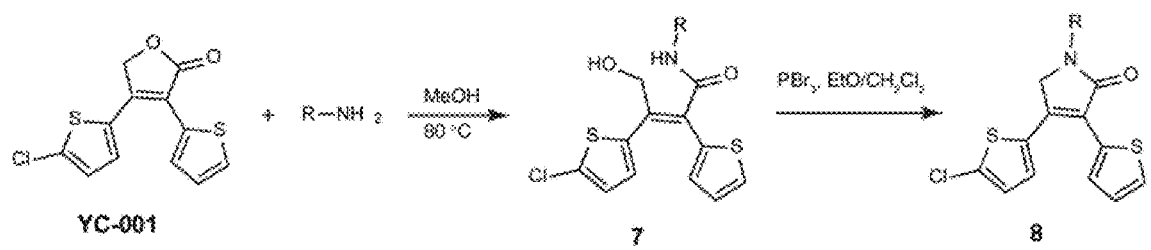
c
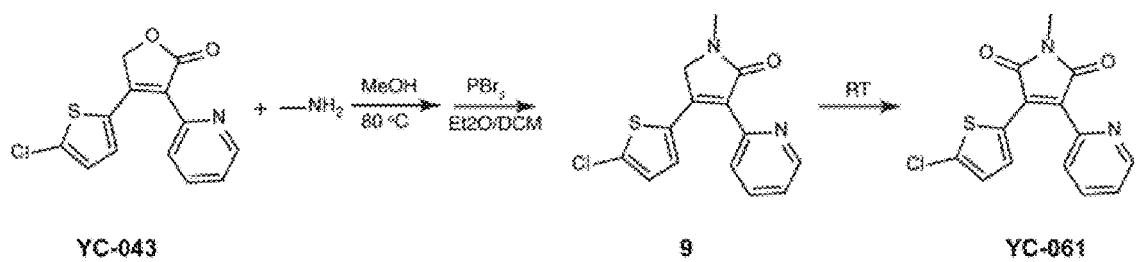
d
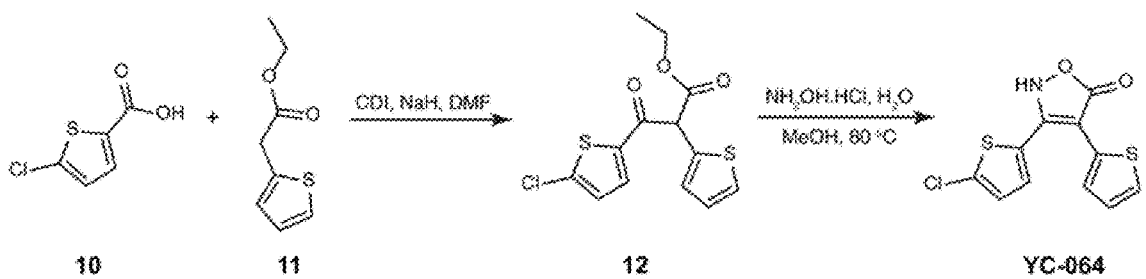
e
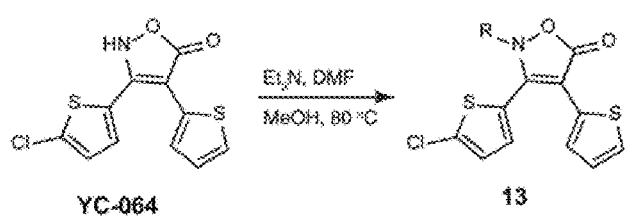
Figs. 17A-E

COMPOUNDS AND METHODS OF TREATING RETINAL DEGENERATION

RELATED APPLICATION

This application claims priority from U.S. Provisional Application Nos. 62/491,811, filed Apr. 28, 2017 and 62/645,576 filed Mar. 20, 2018, the subject matter of which are incorporated herein by reference in their entirety.

GOVERNMENT FUNDING

This invention was made with government support under EY024992, EY021126, EY025214, and EY011373 awarded by the National Institutes of Health.

The government has certain rights in the invention.

SEQUENCE LISTING

The instant application contains a Sequence Listing which has been submitted electronically in XML format and is hereby incorporated by reference in its entirety. Said XML copy, created on Sep. 5, 2023, is named CWR-026277US CON-2.st.26 and is 12,973 bytes in size.

BACKGROUND

Protein misfolding diseases, collectively referred to as proteopathies, are associated with a variety of neurodegenerative, metabolic, and muscular conditions, as well as disorders affecting vision. A significant number of genetic mutations identified in inherited retinal degenerations lead to protein misfolding. One of the most frequent mutations causing Leber congenital amaurosis (LCA) is the R91W RPE65 mutation which leads to the instability of an essential retinoid isomerase normally required to regenerate the 11-cis-chromophore for maintenance of vision and cone cell survival. Additionally, a common double mutation in ABCA4(L541P/A1038V) causes the recessive form of Stargardt disease, as the ATP binding cassette subfamily A member 4 (ABCA4) photoreceptor cell-specific ABC transporter is completely degraded due to misfolding. The P23H RHO mutation, is found in approximately 10% of the cases of autosomal dominant retinitis pigmentosa (RP) reported in North America, and is characterized by the inherent instability of opsin, the rod visual pigment protein, and the disruption of rod photoreceptor cell homeostasis. Unfortunately, most inherited retinal degenerations currently lack effective and safe treatments.

RP is a progressive retinal degeneration, inherited in autosomal dominant (ad), autosomal recessive (ar) and X-linked forms. Defects in more than 60 genes have been found to cause RP, among which the RHO gene encoding the protein component of the rhodopsin pigment is the most common causal gene for adRP. More than 140 mutations have been identified within RHO that mostly cause adRP, and the P23H mutation is the most frequent adRP mutation found in North America. It is an example of a class II rhodopsin mutation, which share common features pointing to the structural instability of opsin. The severity of adRP associated with the P23H RHO mutation varies individually. In general, compared to C-terminal RHO mutations which manifest in the rapid loss of vision, the P23H rhodopsin mutation results in a relatively slow progression that takes decades until a severe vision loss occurs. This slow disease progression creates an ideal therapeutic window for pharmacological interventions to preserve surviving rod photoreceptors and maintain vision for this specific type of adRP. Mechanistic studies and drug discovery targeting the stabilization of the P23H opsin mutant can provide therapies not only for patients carrying this particular mutation, but other cases associated with different rhodopsin mutations as well.

SUMMARY

This application relates to compounds and methods of treating retinal degeneration associated with inherited rhodopsin mutations in the ocular tissue of a subject. The retinal degeneration, can include, for example, macular degeneration, including age-related macular degeneration, Stargardt disease, and retinitis pigmentosa. The retinitis pigmentosa can include autosomal dominate retinitis pigmentosa associated with a P23H RHO mutation.

The method of treating the retinal degeneration in a subject can include administering to the subject a therapeutically effective amount of a small molecule compound that can act as a chaperone of rhodopsin.

In some embodiments, the small molecule chaperone of rhodopsin can include a compound of formula (I):

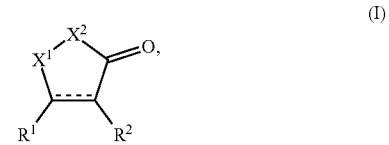

(I)

wherein $X^1$ is $CH_2$, $C=O$, $N-R^3$;

wherein $X^2$ is O or $N-R^4$.

wherein $R^1$ and $R^2$ are each independently selected from the group consisting of hydrogen a substituted or unsubstituted cycloalkyl, heterocyclyl, aryl, and heteroaryl, wherein at least one of $R^1$ or $R^2$ is not H;

wherein $R^3$ and $R^4$ are each independently selected from the group consisting of hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof;

and pharmaceutically acceptable salts thereof.

In some embodiments, the small molecule chaperone of rhodopsin can include a compound of formula (II):

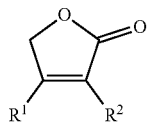
(II)

wherein R¹ and R² are each independently selected from the group consisting of hydrogen a substituted or unsubstituted cycloalkyl, heterocyclyl, aryl, and heteroaryl, wherein at least one of R¹ or R² is,

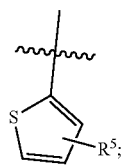

wherein R⁵ is hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof;

and pharmaceutically acceptable salts thereof.

In some embodiments, the small molecule chaperone of rhodopsin can include a compound of formula (III):

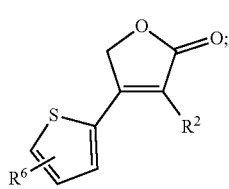
(III)

wherein R² and R⁶ are each individually hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof;

and pharmaceutically acceptable salts thereof.

In still other embodiments, the small molecule chaperone of rhodopsin can include a compound of formula (IV):

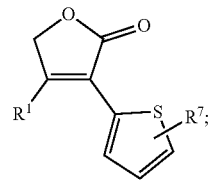
(IV)

wherein R² and R⁷ are each individually hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof;

and pharmaceutically acceptable salts thereof.

In some embodiments, the small molecule chaperone of rhodopsin can include a compound selected from the group consisting of:

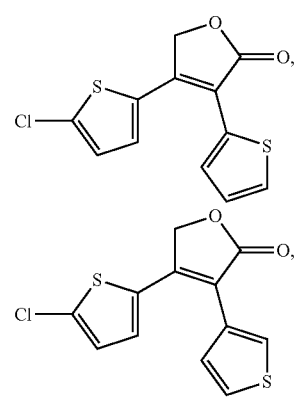

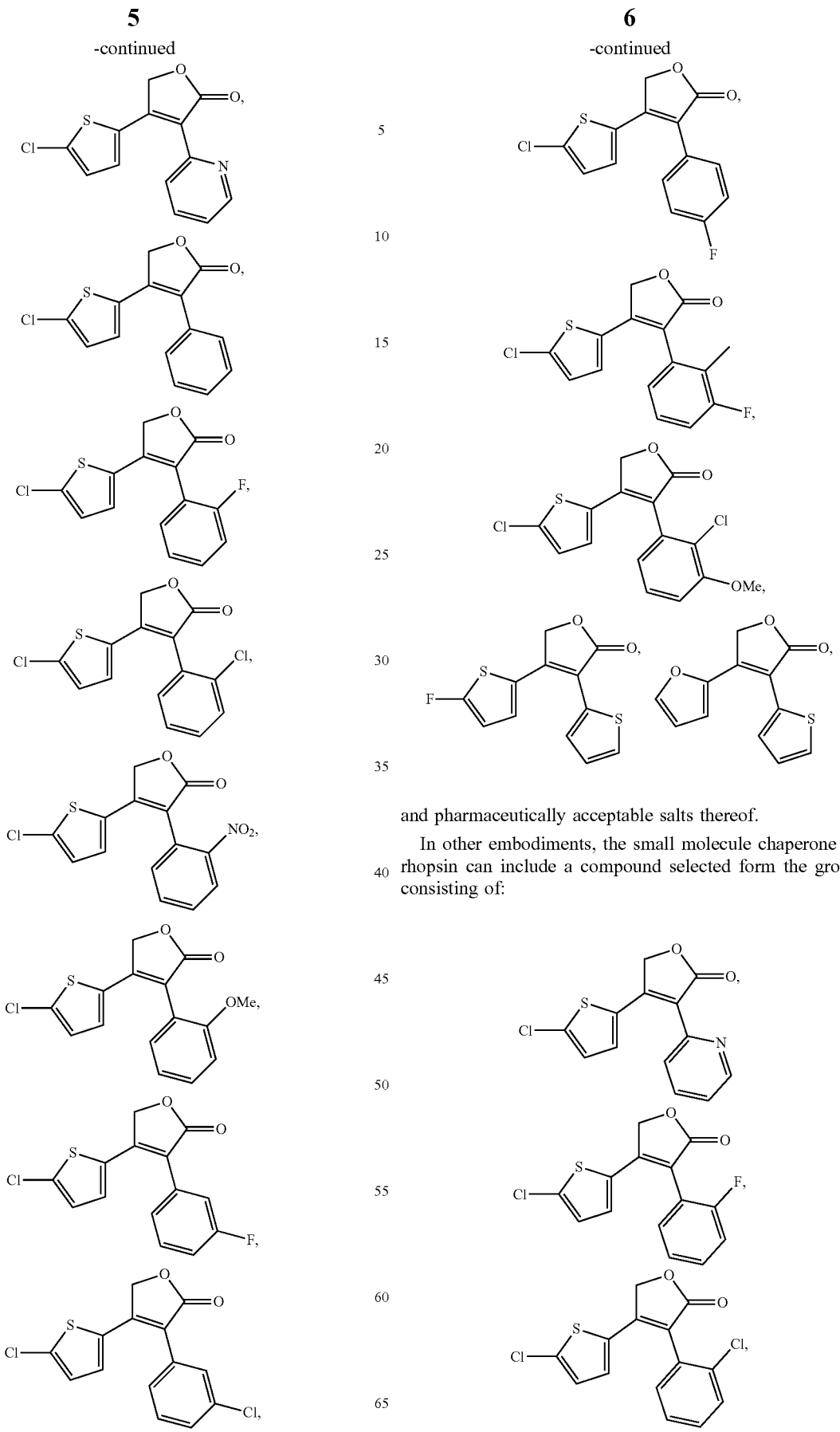
and pharmaceutically acceptable salts thereof.
In other embodiments, the small molecule chaperone of rhopsin can include a compound selected form the group consisting of:
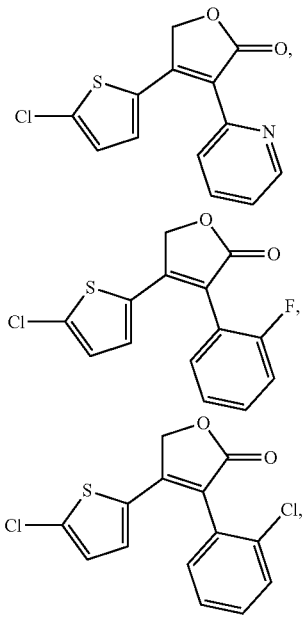

-continued

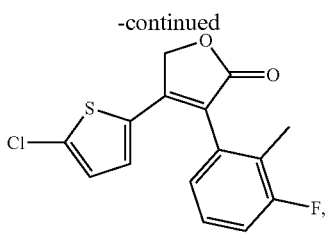

and pharmaceutically acceptable salts thereof.

In some embodiments, the compounds described herein can promote rod photoreceptor cell homeostasis in the subject. In other embodiments, the compounds described herein can inhibit early ER associated protein degradation (ERAD) pathway in photoreceptor cells of the subject. In still other embodiments, the compounds described herein can inhibit photoreceptor cell death in the subject.

In other embodiments, the compounds can be delivered to a subject by at least one of topical administration, systemic administration, intravitreal injection, and/or intraocular delivery. In one example, the compounds described herein can be provided in a preparation for systemic delivery.

BRIEF DESCRIPTION OF THE DRAWINGS

FIGS. 1(A-G) illustrate images and plots showing YC-001 rescues P23H opsin from the ER to the plasma membrane. (a-c), Chemical structures of 11-cis-retinal, 9-cis-retinal, and YC-001, respectively. The three chemical moieties of YC-001 are shaded and numbered. (d). Diagram of the β-Gal fragment complementation assay used for the HTS. Briefly, two complementary fragments of β-Gal (EA and PK) were individually fused with a plasma membrane-anchored peptide, the pleckstrin homology domain of phospholipase C δ (PLC-EA, in cyan), and the mouse P23H opsin mutant (P23H-PK, in magenta), respectively. A U2OS stable cell line was generated that co-expressed both PLC-EA and P23H-PK. Due to its inherent instability, P23H-PK accumulated in the ER, whereas PLC-EA remained on the plasma membrane, leading to a loss of β-Gal activity due to the separation of the two fragments of this enzyme. Upon treatment with an active compound that rescues the folding and transport of P23H opsin to the plasma membrane, a recovery of β-Gal activity is observed due to co-localization of PK and EA. (e) The activities of YC-001 (black boxes) and 9-cis-retinal (magenta circles) were tested in a dose-dependent manner employing the β-Gal fragment complementation assay. Each compound was preincubated for 24 h before β-Gal activity was tested. Activity scores were standardized to the effect of 5 µM 9-cis-retinal as 100%. Dose dependence was fitted by the Hill function with Origin software. $R^2$, $EC_{50}$ (µM), and Max score for each compound were obtained from curve fitting and are listed in the graph. The experiment was repeated 3 times. (f) Activities of 40 µM YC-001 (black boxes) and 5 µM 9-cis-retinal (magenta circles) were tested as a function of time with the (3-Gal fragment complementation assay. The time course graph was fitted with a Hill function and $T_{1/2}$s were obtained and listed in the graph. This experiment was repeated twice. (g) Activities of YC-001 together with 5 µM 9-cis-retinal were tested in a dose-dependent manner and plotted in black triangles. This experiment was repeated twice. The activity scores were plotted as the averages of three biological replicates, with the error bars as the s.d.s.

FIGS. 2(A-N) illustrate images and plots showing high-content imaging analysis of P23H mutant opsin. (a-h) are fluorescence images of NIH3T3 cells expressing mouse WT or P23H opsin imaged with Cy3 (yellow) and DAPI (blue). Scale bar, 50 µm. Images in (a-d) are from cells with rhodopsin immunostained on the cell surface only (Non-permeabilized). Images in (e-h) were from cells with rhodopsin immunostained in the whole cell (Permeabilized). Images (a,e) are from NIH3T3 cells expressing WT opsin treated with 0.1% DMSO. Images (b-d) and (f-h) are from NIH3T3 cells expressing P23H opsin treated with 0.1% DMSO, 10 µM YC-001 or 5 µM 9-cis-retinal, left to right, respectively. Graphs (i-n). Graphs (i) and (i) were quantified from cell-surface immunostaining intensities of opsin on the plasma membrane (Opsin INT); graphs K and L are ratios of opsin staining on the plasma membrane compared to the whole cell from whole-cell immunostained images (Opsin Ratio PM-to-total); graphs (m,n) are ratios of opsin staining in the ER region compared to whole cell staining from whole-cell immunostained images (Opsin Ratio ER-to-total). (i,k,m) show immunofluorescence intensities of opsin in controls: 1, NIH3T3 cells expressing WT opsin treated with 0.1% DMSO; 2, NIH3T3 cells expressing P23H opsin treated with 0.1% DMSO; 3, NIH3T3 cells expressing P23H opsin treated with 5 µm 9-cis-retinal in the dark. Graphs (j,l,n) are quantifications of P23H opsin on the plasma membrane (j,l) or ER (n) of NIH3T3 cells, treated with a series of doses of YC-001 (black boxes) or 9-cis-retinal (magenta boxes). Values are averages of triplicate determinations, and error bars are s.d.s from those triplicates. Dose-response curves were fitted using Origin software with $EC_{50}$ (µM), A1 (low plateau) and A2 (high plateau) of each compound listed in the inset box. This experiment was repeated twice.

FIGS. 3(A-G) illustrate immunoblots, a graph, and plots showing YC-001 improved the glycosylation profile of P23H opsin. (a) Effect of different treatments on immunoblots of lysates from NIH3T3 cells expressing WT or P23H opsin. Top panel, immunoblot of opsin; bottom panel, immunoblot of GAPDH. Lanes from left to right, immunoblots from a total of 15 µg lysate from NIH3T3 cells expressing P23H opsin that were treated with 40, 20, 10, 5, 1, or 0.5 µM YC-001, 0.1% DMSO, or 5 µM 9-cis-retinal, respectively; WT opsin, immunoblot from a total of 5 µg lysate from NIH3T3 cells expressing WT opsin treated with 0.1% DMSO. (b) Relative intensities of P23H opsin bands at 50 kDa (blue bars), 70 kDa (black bars) and 120 kDa (magenta bars) represented in cumulative bars as a function of YC-001 dosage. The band at 50 kDa is an opsin monomer with mature glycosylation; the band at 70 kDa is an opsin dimer with immature glycosylation; the band at 120 kDa is an opsin dimer with mature glycosylation. (c) Immunoblot of opsin from cell lysates deglycosylated by PNGaseF. Lanes from left to right, lysates from NIH3T3 cells expressing P23H opsin treated with either 0.1% DMSO, 5 µM 9-cis-retinal or 10 µM YC-001, respectively; WT opsin, lysate from NIH3T3 cells expressing WT opsin treated with 0.1% DMSO. (d) Immunoblot of P23H opsin from cells treated with 10 µM scriptaid or 0.1% DMSO, respectively. Immunoblot of GAPDH is shown on the bottom as a loading control. (e-g), Ligand binding affects the chromophore-binding pocket of rod opsin. Bovine opsin within the ROS disc membranes was used for this assay. Trp fluorescence of opsin was measured both before and after addition of ligands (FIG. 11). Changes of fluorescence intensity at 330 nm (ΔF/F0) are plotted as a function of the concentration of 9-cis-retinal (e), YC-001 (f), or scriptaid (g), respectively.

Binding curves were fitted with the Hill function using Origin software. $EC_{50}$s (μM) of each ligand were calculated and averaged from three biological repeats±s.d.s and are indicated in the respective graphs. This experiment was repeated twice.

FIGS. 4(A-F) illustrate plots showing YC-001 delays isorhodopsin pigment regeneration. Bovine opsin (2.5 μM) in ROS membranes was incubated with compounds (20 μM) for 30 min at RT. After membrane solubilization, absorbance at 487 nm was recorded to measure the amount of isorhodopsin. (a) UV-visible absorption spectra of opsin (black) and opsin treated with 9-cis-retinal (magenta), YC-001 (light green), YC-001 followed by 9-cis-retinal for 15 min each (blue), and a mixture of YC-001 and 9-cis-retinal (grey). (b) UV-visible absorption spectra of opsin treated with 9-cis-retinal (magenta), scriptaid (dark green) scriptaid followed by 9-cis-retinal for 15 min each (purple), and a mixture of 9-cis-retinal and scriptaid (grey). (c) Percentage of regenerated isorhodopsin from sequential treatment with YC-001 and 9-cis-retinal for 15 min each as a function of YC-001 concentration in a log format. Isorhodopsin regenerated with 9-cis-retinal alone was normalized as 100%. Values and error bars were averages and s.d.s from three biological. Inset, absorption spectra of opsin with 5 μM 9-cis-retinal and 0 (red), 2.5 (pink), 5 (magenta), 10 (purple), 20 (dark blue), 40 (cyan), 60 (light blue), or 80 μM YC-001 (green), respectively. (d) Time course of isorhodopsin regeneration in the presence of 0, 20 or 60 μM YC-001 followed by addition 5 μM 9-cis-retinal for 15 min each (black, blue and magenta boxes, respectively). Values and error bars were averages and s.d.s of three biological repeats. Data were fitted with second-order exponential decay and apparent half-lives ($T_{1/2}$±standard error) are shown in the inset box. (e) Percentage of regenerated isorhodopsin from aged opsin (magenta) or opsin incubated with YC-001 (blue) at RT for 0, 1, 3 and 6 h before regeneration with 9-cis-retinal. Isorhodopsin regenerated from opsin at 0 h with no treatment was set at 100%. Plots of regenerated isorhodopsin levels were fitted by the exponential decay function. The inset shows the absorption spectra of regenerated isorhodopsin from aged opsins. Black, opsin alone. (f) Raman spectrum of YC-001 in DMSO solution (top) and a difference spectrum after subtracting the spectrum of rod opsin crystal from that of opsin crystal soaked with YC-001 (bottom). Each experiment was repeated twice.

FIGS. 5(A-F) illustrate graphs and plots showing YC-001 is an inverse agonist and antagonist to rod opsin. Rhodopsin couples to $G_{i/o}$ signaling in a light-dependent manner leading to the reduction of cAMP level in mammalian cells. Forskolin was added to the cells to saturate their cAMP levels. (a) Levels of cAMP in NIH3T3-(Opsin/GFP) cells treated as noted under the chart. Cells treated in the dark and in light were in grey and white bars, respectively. Bar values are the averages of three replicates, and error bars are s.d.s of the replicates. (b) Levels of cAMP in NIH3T3-(GFP) cells treated with PBS, 10 μM 9-cis-retinal, or 40 μM YC-001, respectively. (c) cAMP levels in NIH3T3-(Opsin/GFP) cells treated with a series of YC-001 doses in the presence (magenta circles) or absence of 1 μM of 9-cis-retinal (black squares) under light. Doses of YC-001 tested were 80, 20, 10, 5, 2.5, 1.25, 0.625 and 0.313 μM. The cAMP level in cells treated with forskolin only was normalized as 100%, and that treated without forskolin as 0%. (d) cAMP levels in NIH3T3-(Opsin/GFP) cells treated with a dose series of 9-cis-retinal in the presence (magenta circles) or absence of 40 μM of YC-001 (black squares) under light. Doses of 9-cis-retinal tested were 40, 13.3, 4.44, 1.48, 0.494, 0.165, 0.055, 0.018 and 0.001 μM. (e) $G_t$ activation by bovine rod opsin or isorhodopsin. Constitutive activity of bovine opsin in disc membranes or photoactivated isorhodopsin activity was recorded by fluorescence with excitation and emission at 300 and 345 nm, respectively, as a function of time, due to GTPγS-induced dissociation of the opsin/isorhodopsin:$G_t$ complex. Dashed experimental lines were fitted by the first-order exponential decay functions shown in solid lines. Each condition was repeated in three biological replicates and initial rates and error bars were averages and s.d.s. shown in (f). Opsin were treated with DMSO (grey), 40 μM YC-001 (black), 40 μM YC-014 (blue), 40 μM 9-cis-retinal (magenta), and a mixture of 40 μM 9-cis-retinal and 40 μM YC-001 (orange). Each experiment was repeated twice.

FIGS. 6(A-F) illustrate images and plots showing YC-001 protects Abca4$^{-/-}$Rdh8$^{-/-}$ mouse retinas from light damage. Due to the loss of both ABCA4 and RDH8, all-trans-retinal cannot be efficiently cleared from the ROS of Abca4$^{-/-}$-Rdh8$^{-/-}$ mice. Thus, their retinas undergo degeneration upon exposure to intense light. Here, Abca4$^{-/-}$Rdh8$^{-/-}$ mice were treated with either DMSO or YC-001 i.p. 30 min before exposure to 10,000 lux light for 30 min. SD-OCT images were taken seven days after light exposure (a-d). Mice then were sacrificed and their eyes were used for histological imaging (e,f). (a) SD-OCT images from mice treated with 50 μL DMSO. Arrowheads indicate significantly degenerated ONL. Scale bar, 200 μm. (b,c) SD-OCT images from mice treated with 50 or 200 mg kg$^{-1}$ bw of YC-001, respectively. (d) Plots of ONL thickness from SD-OCT images in (a-c). Lines represent averaged ONL thicknesses from three mice and error bars are the s.d.s. (e) HE staining of Abca4$^{-/-}$Rdh8$^{-/-}$ mouse retina seven days after pre-incubation in DMSO and exposure to 10,000 lux light. Scale bar, 100 μm. (f) HE staining of Abca4$^{-/-}$Rdh8$^{-/-}$ mouse retina seven days after pre-incubation with 200 mg kg$^{-1}$ bw YC-001 and exposure to 10,000 lux light. RPE, retinal pigmented epithelium; OS, outer segment; IS, inner segment; ONL, outer nuclear layer; OPL, outer plexiform layer; INL, inner nuclear layer; IPL, inner plexiform layer; GCL, ganglion cell layer. This experiment was repeated twice.

FIGS. 7(A-F) illustrate plots showing YC-001 enters mouse eyes not affecting the visual cycle. (a) HPLC chromatogram of a YC-001 standard indicating a peak at a retention time of 13.2 min with an absorbance at 340 nm. Inset shows the standard curve of YC-001 hexane extracts with its peak area versus its weight in ng. (b) HPLC chromatogram of hexane extracts from six-weeks old C57BL/6 mouse eyes 0.5, 3 or 24 h after i.p. injection with YC-001 at 200 mg kg$^{-1}$ bw in black, magenta, and blue, respectively. The inset is an enlarged chromatogram of the peaks with retention times from 12 to 14 min. (c) Amounts of YC-001 in pmol per eye plotted as a function of time after injection with YC-001. Time 0 denotes mice not injected with YC-001. (d) Amounts of 11-cis-retinyl-oxime representing the relative amounts of regenerated rhodopsin pigment were plotted as a function of time after bleaching. Six-weeks-old C57BL/6 mice were injected with 200 mg kg$^{-1}$ bw YC-001 (magenta) or 50 μL DMSO i.p. 30 min before their exposure to 10,000 lux light for 10 min. Mice then were placed in the dark and euthanized at 0, 2, 4, 6 and 24 h after bleaching. Retinyl-oximes were extracted from homogenized eyes and separated by HPLC. (e) Recovery of mouse scotopic ERG a-wave amplitude plotted as a function of time after bleaching. Dark-adapted C57BL/6 mice received YC-001 (200 mg kg$^{-1}$ bw) or DMSO by ip injection 1 h before light exposure. Mice with dilated pupils were then exposed to 2000 lux light for 5 min. Yellow shade represents 5 min illumination. Scotopic a-wave amplitude from unbleached dark-adapted mice was shown before time 0. (f) Bw of YC-001 or DMSO treated mice plotted as a function of their age. C57BL/6 mice were treated with 100 or 200 mg kg$^{-1}$ bw YC-001 by daily i.p. injections, starting on Day 14. Black, DMSO; blue, 100 mg kg$^{-1}$ YC-001; magenta, 200 mg kg$^{-1}$ YC-001. Values and error bars were from averages and s.d.s, n=3. Each experiment was repeated twice.

FIGS. 8(A-B) illustrate images showing the effect of YC-001 on the transport of rod opsin mutants. (a), Illustration of seven autosomal dominant retinitis pigmentosa associated mutation sites on the bovine rhodopsin crystal structure (PDB ID: 1f88). The overall structure of rhodopsin is shown in blue with 11-cis-retinal labeled in orange. Side chains of T4, P23, G106, D190, and P267 are labeled in red, and side chains of P53 and C110 are labeled in magenta. (b), Cell surface immunostained images of rod opsin mutants expressed in NIH3T3 cells exposed to DMSO, 9-cis-retinal or YC-001. Cells transfected with human rhodopsin WT or mutants were treated with DMSO (0.1%) or YC-001 (10 μM) for 24 h. Cells were fixed and only rod opsin on the cell surface was immunostained with Alexa 488-conjugated B6-30 anti-rhodopsin antibody. Green fluorescence images were taken under a 20× objective. 9-cis-retinal was tested at 5 μM and YC-001 at 10 μM, as labeled in each panel. This experiment was repeated twice.

FIGS. 9(A-B) illustrate an image and graph showing YC-001 does not stabilize clarin1$^{N48K}$-Venus. a Fluorescence images of HEK-293 cells expressing both CLRN1$^{N48K}$-Venus and DsRed-Express-DR treated with either DMSO (top), MG-132 (middle) or YC-001 (bottom). Left to right are fluorescence images of CLRN1$^{N48K}$-Venus, DsRed-Express-DR and Hoechst33342, respectively. b Relative fluorescence intensities of CLRN1$^{N48K}$-Venus (green bars) and DsRed-Express-DR from HEK-293 cells treated with DMSO, MG-132 or YC-001. Fluorescence intensities from DMSO-treated cells were normalized to 100%. Bars were averaged from sixteen biological replicates and standard deviations are shown as error bars. **, P=1.05× 10$^{-5}$, *P=7.00×10$^{-4}$ compared to DMSO-treated control, using a two-tailed Student test.

FIGS. 10(A-C) illustrate plots showing YC-001 binds to rod opsin in a manner that affects the chromophore-binding pocket. The Trp fluorescence spectra of opsin were recorded upon titration with different concentrations of either 9-cis-retinal (a), YC-001 (b) or scriptaid (c) in the dark. RFU, relative fluorescence units. Quenching of Trp opsin fluorescence by increasing concentrations of ligands is indicated with arrows. Changes of fluorescence intensity at 330 nm (ΔF/F0) are plotted as a function of the concentration of 9-cis-retinal, YC-001 and scriptaid, respectively in FIG. 3e-g. The increased peak around 400 nm was due to scriptaid fluorescence. Each experiment was repeated three times.

FIGS. 11(A-B) illustrate plots showing YC-001 binds to rod opsin through a non-covalent interaction. a Absorption spectra of isorhodopsin or opsin purified under conditions provided in FIG. 4 (a,b) by 1D4 immunoaffinity chromatography. b Absorption spectra of rhodopsin in ROS disc membranes under treatment with YC-001. Brown, ROS membranes; light green, YC-001 only; dark green, ROS disc membranes incubated with excess YC-001 for 90 min. Inset shows the enlarged region of the absorption spectra from 400 to 650 nm. Each experiment was repeated twice.

FIGS. 12(A-B) illustrate plots showing LC-MS analysis of YC-001 from mouse eyes. a Chromatogram of ions with m/z from 283 to 284. Black, YC-001 standard; red, extract from eyes of a mouse treated with YC-001, collected after purification with a retention time of 13.2 min (FIG. 13b). b MS spectra at a LC retention time of 8.8 min (arrows in a). Top, YC-001 standard; bottom, mouse eye extract. The peak with m/z at 283.07 corresponds to YC-001. This experiment was repeated for twice.

FIGS. 13(A-B) illustrate plots showing YC-001 does not affect the activity of COX-1. a Changes of relative COX-1 activity (% of Enzyme only) treated with DMSO as vehicle control and a COX-1 inhibitor, SC560, as positive control. Values and error bars indicate mean±SD (n=3). p<0.01 SC560 versus Enzyme only. *p<0.001 SC560 versus vehicle control. b The dose-response graph showed relative COX-1 activity (% of Enzyme only) treated with different concentrations of YC-001 in Log format. Relative COX-1 activities were normalized by the activity of Enzyme only as 100%. Values and error bars indicate mean±SD (n=3). This experiment was repeated twice.

FIG. 14 illustrates a plot showing fast elimination of YC-001 in the plasma of C57BL/6 mice following intraperitoneal (i.p.) injection. The plot of plasma concentration of YC-001 ([YC-001]$_{plasma}$) versus time is shown in the top graph. [YC-001]$_{plasma}$ was measured at 5, 10, 15, 20, 30, 45, 60 and 90 min after administration via i.p. injection at 200 mg/kg body weight. Each data point and error bar was the average and standard deviation of [YC-001]$_{plasma}$ from four mice (2 female and 2 male) at 8-12 weeks of age, respectively. The elimination curve was fitted with the first-order exponential decay (y=C$_0$×e$^{(-xT/2)}$) using Origin Software. The bottom table shows the pharmacokinetic parameters estimated from the YC-001 elimination curve. K$_e$= 0.693/T$_{1/2}$, V$_d$=Dose/C$_0$, and Clearance=K$_e$×V$_d$. Dose, dose of YC-001 administered; Route, route of administration; n, total number of mice used for the plot; T$_{1/2}$, the half-life; C$_0$, the initial plasma concentration of YC-001 at time 0; K$_e$, estimated elimination rate constant; V$_d$, estimated volume of distribution. This experiment was performed once.

FIGS. 15(A-B) illustrate plots showing YC-001 is quickly cleared by mouse (a) or human liver microsomes (b). To predict the stability of YC-001 in the liver after in vivo treatment, 5 μM YC-001 was incubated with 0.125 mg/mL mouse or human liver microsomes and 1 mM NADPH for 30 or 250 min at 37° C. (solid circles). Verapamil (solid triangles) and Quinidine (solid diamonds) were tested under the same conditions, as rapid- and slow-clearance controls, respectively. YC-001 incubated with liver microsomes without NADPH was used as a negative control (open circles). The amount of each compound at different times was quantified by LC-MS. Each data point was obtained from an average of three biological repeats, with standard deviations of the repeats as corresponding error bars. Data from each compound was fitted to a first-order exponential decay with Sigmaplot software. Half-life (T$_{1/2}$) and initial Clearance (Cl$_{int}$) of each compound are listed in the bottom table. Cl$_{int}$ (μL min$^{-1}$ mg$^{-1}$)=0.693×1/T$_{1/2}$ (min)×volume (μL)/mg. This experiment was repeated once with human and mouse liver microsomes.

FIGS. 16(A-C) illustrate full scans of immunoblotted membranes. Areas used in FIG. 4 are framed by red rectangles.

FIGS. 17(A-E) illustrate the synthesis of analogs of YC-001. a Synthesis of analogs of YC-001 with substitutions at C3 or C4 positions. X=Cl or Br. R1 and R2 are substitutions of subgroup I and III of YC-001 shown in FIG. 1C. Analogs of YC-001 were prepared by the condensation of α-halogeno ketones (4) with substituted acetic acids (5) in the presence of trimethylamine (Et3N) and acetonitrile (CH3CN) at room temperature (RT) for 20 min followed by intramolecular cyclization of the acetate intermediate with 1,8-diazabicycolo[5.4.0]undec-7-ene (DBU), yielding the analogs of YC-001 (6). b Synthesis of analogs substituting the furan-2(5H)-one scaffold of YC-001 with a 1,5-dihydro-2H-pyrrol-2-one ring. Target compounds (8) were prepared by treatment of YC-001 with the appropriate amine ($NH_2$—R) neat or with methanol (MeOH) at 80° C. followed by intramolecular cyclization of the amide intermediate (7) with $PBr_3$ and ethylene oxide ($Et_2O$) or $CH_2Cl_2$. C Synthesis of YC-061. YC-043 was treated with methylamine in the presence of MeOH at 80° C. followed by incubation with $PBr_3$ and $Et_2O$ or $CH_2Cl_2$ to yield N-methyl analogue (9), which was then oxidized to YC-061 during purification and RT incubation. d Two-step synthesis of YC-064. A Claisen condensation of ethyl 2-(thiophen-2-yl)acetate (11) and (5-chlorothiophen-2-yl)imidazolide (10) produced the -ketoester (12) with carbonyldiimidazole (CDI), sodium hydride (NaH) and dimethylformamide (DMF). YC-064 was then obtained by cyclocondensation of hydroxylamine hydrochloride ($NH_2OH \cdot HCl$) with -ketoester (12) in the presence of MeOH at 80° C. e Synthesis of analogs replacing the furan-2(5H)-one scaffold of YC-001 with an isoxazol-5(2H)-one ring. Type 13 YC compounds were synthesized by N-alkylation of YC-064 with trimethylamine ($Et_3N$), DMF and MeOH at 80° C.

DETAILED DESCRIPTION

For convenience, certain terms employed in the specification, examples, and appended claims are collected here. Unless defined otherwise, all technical and scientific terms used herein have the same meaning as commonly understood by one of ordinary skill in the art to which this application belongs.

The articles "a" and "an" are used herein to refer to one or to more than one (i.e., to at least one) of the grammatical object of the article. By way of example, "an element" means one element or more than one element.

The terms "comprise," "comprising," "include," "including," "have," and "having" are used in the inclusive, open sense, meaning that additional elements may be included. The terms "such as", "e.g.", as used herein are non-limiting and are for illustrative purposes only. "Including" and "including but not limited to" are used interchangeably.

The term "or" as used herein should be understood to mean "and/or", unless the context clearly indicates otherwise.

As used herein, the term "about" or "approximately" refers to a quantity, level, value, number, frequency, percentage, dimension, size, amount, weight or length that varies by as much as 15%, 10%, 9%, 8%, 7%, 6%, 5%, 4%, 3%, 2% or 1% to a reference quantity, level, value, number, frequency, percentage, dimension, size, amount, weight or length. In one embodiment, the term "about" or "approximately" refers a range of quantity, level, value, number, frequency, percentage, dimension, size, amount, weight or length±15%, ±10%, ±9%, ±8%, ±7%, ±6%, ±5%, ±4%, ±3%, ±2%, or ±1% about a reference quantity, level, value, number, frequency, percentage, dimension, size, amount, weight or length.

It will be noted that the structure of some of the compounds of the application include asymmetric (chiral) carbon or sulfur atoms. It is to be understood accordingly that the isomers arising from such asymmetry are included herein, unless indicated otherwise. Such isomers can be obtained in substantially pure form by classical separation techniques and by stereochemically controlled synthesis.

The compounds of this application may exist in stereoisomeric form, therefore can be produced as individual stereoisomers or as mixtures.

The term "isomerism" means compounds that have identical molecular formulae but that differ in the nature or the sequence of bonding of their atoms or in the arrangement of their atoms in space. Isomers that differ in the arrangement of their atoms in space are termed "stereoisomers". Stereoisomers that are not mirror images of one another are termed "diastereoisomers", and stereoisomers that are non-superimposable mirror images are termed "enantiomers", or sometimes optical isomers. A carbon atom bonded to four nonidentical substituents is termed a "chiral center" whereas a sulfur bound to three or four different substituents, e.g., sulfoxides or sulfinimides, is likewise termed a "chiral center".

The term "chiral isomer" means a compound with at least one chiral center. It has two enantiomeric forms of opposite chirality and may exist either as an individual enantiomer or as a mixture of enantiomers. A mixture containing equal amounts of individual enantiomeric forms of opposite chirality is termed a "racemic mixture". A compound that has more than one chiral center has 2n–1 enantiomeric pairs, where n is the number of chiral centers. Compounds with more than one chiral center may exist as either an individual diastereomer or as a mixture of diastereomers, termed a "diastereomeric mixture". When one chiral center is present, a stereoisomer may be characterized by the absolute configuration (R or S) of that chiral center. Alternatively, when one or more chiral centers are present, a stereoisomer may be characterized as (+) or (−). Absolute configuration refers to the arrangement in space of the substituents attached to the chiral center. The substituents attached to the chiral center under consideration are ranked in accordance with the Sequence Rule of Cahn, Ingold and Prelog. (Cahn et al, Angew. Chem. Inter. Edit. 1966, 5, 385; errata 511; Cahn et al., Angew. Chem. 1966, 78, 413; Cahn and Ingold, J Chem. Soc. 1951 (London), 612; Cahn et al., Experientia 1956, 12, 81; Cahn, J., Chem. Educ. 1964, 41, 116).

The term "geometric Isomers" means the diastereomers that owe their existence to hindered rotation about double bonds. These configurations are differentiated in their names by the prefixes cis and trans, or Z and E, which indicate that the groups are on the same or opposite side of the double bond in the molecule according to the Cahn-Ingold-Prelog rules. Further, the structures and other compounds discussed in this application include all atropic isomers thereof.

The term "atropic isomers" are a type of stereoisomer in which the atoms of two isomers are arranged differently in space. Atropic isomers owe their existence to a restricted rotation caused by hindrance of rotation of large groups about a central bond. Such atropic isomers typically exist as a mixture, however as a result of recent advances in chromatography techniques, it has been possible to separate mixtures of two atropic isomers in select cases.

The terms "crystal polymorphs" or "polymorphs" or "crystal forms" means crystal structures in which a compound (or salt or solvate thereof) can crystallize in different crystal packing arrangements, all of which have the same elemental composition. Different crystal forms usually have different X-ray diffraction patterns, infrared spectral, melting points, density hardness, crystal shape, optical and electrical properties, stability and solubility. Recrystallization solvent, rate of crystallization, storage temperature, and other factors may cause one crystal form to dominate. Crystal polymorphs of the compounds can be prepared by crystallization under different conditions.

The term "derivative" refers to compounds that have a common core structure, and are substituted with various groups as described herein.

The term "bioisostere" refers to a compound resulting from the exchange of an atom or of a group of atoms with another, broadly similar, atom or group of atoms. The objective of a bioisosteric replacement is to create a new compound with similar biological properties to the parent compound. The bioisosteric replacement may be physico-chemically or topologically based. Examples of carboxylic acid bioisosteres include acyl sulfonimides, tetrazoles, sulfonates, and phosphonates. See, e.g., Patani and LaVoie, Chem. Rev. 96, 3147-3176 (1996).

The phrases "parenteral administration" and "administered parenterally" are art-recognized terms, and include modes of administration other than enteral and topical administration, such as injections, and include, without limitation, intravenous, intramuscular, intrapleural, intravascular, intrapericardial, intraarterial, intrathecal, intracapsular, intraorbital, intracardiac, intradermal, intraperitoneal, transtracheal, subcutaneous, subcuticular, intra-articular, subcapsular, subarachnoid, intraspinal and intrasternal injection and infusion.

The term "treating" is art-recognized and includes inhibiting a disease, disorder or condition in a subject, e.g., impeding its progress; and relieving the disease, disorder or condition, e.g., causing regression of the disease, disorder and/or condition. Treating the disease or condition includes ameliorating at least one symptom of the particular disease or condition, even if the underlying pathophysiology is not affected.

The term "preventing" is art-recognized and includes stopping a disease, disorder or condition from occurring in a subject, which may be predisposed to the disease, disorder and/or condition but has not yet been diagnosed as having it. Preventing a condition related to a disease includes stopping the condition from occurring after the disease has been diagnosed but before the condition has been diagnosed.

The term "pharmaceutical composition" refers to a formulation containing the disclosed compounds in a form suitable for administration to a subject. In a preferred embodiment, the pharmaceutical composition is in bulk or in unit dosage form. The unit dosage form is any of a variety of forms, including, for example, a capsule, an IV bag, a tablet, a single pump on an aerosol inhaler, or a vial. The quantity of active ingredient (e.g., a formulation of the disclosed compound or salts thereof) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, intranasal, inhalational, and the like. Dosage forms for the topical or transdermal administration of a compound described herein includes powders, sprays, ointments, pastes, creams, lotions, gels, solutions, patches, nebulized compounds, and inhalants. In a preferred embodiment, the active compound is mixed under sterile conditions with a pharmaceutically acceptable carrier, and with any preservatives, buffers, or propellants that are required.

The term "flash dose" refers to compound formulations that are rapidly dispersing dosage forms.

The term "HDAC inhibitor" or "inhibitor of HDAC" encompasses any synthetic, recombinant, or naturally-occurring inhibitor, including any pharmaceutical salts or hydrates of such inhibitors, and any free acids, free bases, or other free forms of such inhibitors capable of inhibiting the activity of a histone deacetylase (HDAC). "Hydroxamic acid derivative," as used herein, refers to the class of histone deacetylase inhibitors that are hydroxamic acid derivatives. Specific examples of inhibitors are provided herein.

The term "immediate release" is defined as a release of compound from a dosage form in a relatively brief period of time, generally up to about 60 minutes. The term "modified release" is defined to include delayed release, extended release, and pulsed release. The term "pulsed release" is defined as a series of releases of drug from a dosage form. The term "sustained release" or "extended release" is defined as continuous release of a compound from a dosage form over a prolonged period.

The phrase "pharmaceutically acceptable" is art-recognized. In certain embodiments, the term includes compositions, polymers and other materials and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The phrase "pharmaceutically acceptable carrier" is art-recognized, and includes, for example, pharmaceutically acceptable materials, compositions or vehicles, such as a liquid or solid filler, diluent, excipient, solvent or encapsulating material, involved in carrying or transporting any subject composition from one organ, or portion of the body, to another organ, or portion of the body. Each carrier must be "acceptable" in the sense of being compatible with the other ingredients of a subject composition and not injurious to the patient. In certain embodiments, a pharmaceutically acceptable carrier is non-pyrogenic. Some examples of materials which may serve as pharmaceutically acceptable carriers include: (1) sugars, such as lactose, glucose and sucrose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, sunflower oil, sesame oil, olive oil, corn oil and soybean oil; (10) glycols, such as propylene glycol; (11) polyols, such as glycerin, sorbitol, mannitol and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

The compounds of the application are capable of further forming salts. All of these forms are also contemplated herein.

"Pharmaceutically acceptable salt" of a compound means a salt that is pharmaceutically acceptable and that possesses the desired pharmacological activity of the parent compound. For example, the salt can be an acid addition salt. One embodiment of an acid addition salt is a hydrochloride salt. The pharmaceutically acceptable salts can be synthesized from a parent compound that contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, ethanol, isopropanol, or acetonitrile being preferred. Lists of salts are found in Remington's Pharmaceutical Sciences, 18th ed. (Mack Publishing Company, 1990).

The compounds described herein can also be prepared as esters, for example pharmaceutically acceptable esters. For example, a carboxylic acid function group in a compound can be converted to its corresponding ester, e.g., a methyl, ethyl, or other ester. Also, an alcohol group in a compound can be converted to its corresponding ester, e.g., an acetate, propionate, or other ester.

The compounds described herein can also be prepared as prodrugs, for example pharmaceutically acceptable prodrugs. The terms "pro-drug" and "prodrug" are used interchangeably herein and refer to any compound, which releases an active parent drug in vivo. Since prodrugs are known to enhance numerous desirable qualities of pharmaceuticals (e.g., solubility, bioavailability, manufacturing, etc.) the compounds can be delivered in prodrug form. Thus, the compounds described herein are intended to cover prodrugs of the presently claimed compounds, methods of delivering the same and compositions containing the same. "Prodrugs" are intended to include any covalently bonded carriers that release an active parent drug in vivo when such prodrug is administered to a subject. Prodrugs are prepared by modifying functional groups present in the compound in such a way that the modifications are cleaved, either in routine manipulation or in vivo, to the parent compound. Prodrugs include compounds wherein a hydroxy, amino, sulfhydryl, carboxy, or carbonyl group is bonded to any group that may be cleaved in vivo to form a free hydroxyl, free amino, free sulfhydryl, free carboxy or free carbonyl group, respectively.

Examples of prodrugs include, but are not limited to, esters (e.g., acetate, dialkylaminoacetates, formates, phosphates, sulfates, and benzoate derivatives) and carbamates (e.g., N,N-dimethylaminocarbonyl) of hydroxy functional groups, ester groups (e.g., ethyl esters, morpholinoethanol esters) of carboxyl functional groups, N-acyl derivatives (e.g., N-acetyl) N-Mannich bases, Schiff bases and enaminones of amino functional groups, oximes, acetals, ketals and enol esters of ketone and aldehyde functional groups in compounds of Formula I, and the like, See Bundegaard, H. "Design of Prodrugs" p 1-92, Elsevier, New York-Oxford (1985).

The term "protecting group" refers to a grouping of atoms that when attached to a reactive group in a molecule masks, reduces or prevents that reactivity. Examples of protecting groups can be found in Green and Wuts, Protective Groups in Organic Chemistry, (Wiley, 2.sup.nd ed. 1991); Harrison and Harrison et al., Compendium of Synthetic Organic Methods, Vols. 1-8 (John Wiley and Sons, 1971-1996); and Kocienski, Protecting Groups, (Verlag, 3$^{rd}$ ed. 2003).

The term "amine protecting group" is intended to mean a functional group that converts an amine, amide, or other nitrogen-containing moiety into a different chemical group that is substantially inert to the conditions of a particular chemical reaction. Amine protecting groups are preferably removed easily and selectively in good yield under conditions that do not affect other functional groups of the molecule. Examples of amine protecting groups include, but are not limited to, formyl, acetyl, benzyl, t-butyldimethylsilyl, t-butyldiphenylsilyl, t-butyloxycarbonyl (Boc), p-methoxybenzyl, methoxymethyl, tosyl, trifluoroacetyl, trimethylsilyl (TMS), fluorenyl-methyloxycarbonyl, 2-trimethylsilyl-ethyoxycarbonyl, 1-methyl-1-(4-biphenylyl) ethoxycarbonyl, allyloxycarbonyl, benzyloxycarbonyl (CBZ), 2-trimethylsilyl-ethanesulfonyl (SES), trityl and substituted trityl groups, 9-fluorenylmethyloxycarbonyl (FMOC), nitro-veratryloxycarbonyl (NVOC), and the like. Those of skill in the art can identify other suitable amine protecting groups.

Representative hydroxy protecting groups include those where the hydroxy group is either acylated or alkylated such as benzyl, and trityl ethers as well as alkyl ethers, tetrahydropyranyl ethers, trialkylsilyl ethers and allyl ethers.

Additionally, the salts of the compounds described herein, can exist in either hydrated or unhydrated (the anhydrous) form or as solvates with other solvent molecules. Nonlimiting examples of hydrates include monohydrates, dihydrates, etc. Nonlimiting examples of solvates include ethanol solvates, acetone solvates, etc.

The term "solvates" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate.

The compounds, salts and prodrugs described herein can exist in several tautomeric forms, including the enol and imine form, and the keto and enamine form and geometric isomers and mixtures thereof. Tautomers exist as mixtures of a tautomeric set in solution. In solid form, usually one tautomer predominates. Even though one tautomer may be described, the present application includes all tautomers of the present compounds. A tautomer is one of two or more structural isomers that exist in equilibrium and are readily converted from one isomeric form to another. This reaction results in the formal migration of a hydrogen atom accompanied by a switch of adjacent conjugated double bonds. In solutions where tautomerization is possible, a chemical equilibrium of the tautomers will be reached. The exact ratio of the tautomers depends on several factors, including temperature, solvent, and pH. The concept of tautomers that are interconvertible by tautomerizations is called tautomerism.

Of the various types of tautomerism that are possible, two are commonly observed. In keto-enol tautomerism a simultaneous shift of electrons and a hydrogen atom occurs.

Tautomerizations can be catalyzed by: Base: 1. deprotonation; 2. formation of a delocalized anion (e.g., an enolate); 3. protonation at a different position of the anion; Acid: 1. protonation; 2. formation of a delocalized cation; 3. deprotonation at a different position adjacent to the cation.

The term "analog" refers to a chemical compound that is structurally similar to another but differs slightly in composition (as in the replacement of one atom by an atom of a different element or in the presence of a particular functional group, or the replacement of one functional group by another functional group). Thus, an analog is a compound that is similar or comparable in function and appearance, but not in structure or origin to the reference compound.

A "patient," "subject," or "host" to be treated by the subject method may mean either a human or non-human animal, such as a mammal, a fish, a bird, a reptile, or an amphibian. Thus, the subject of the herein disclosed methods can be a human, non-human primate, horse, pig, rabbit, dog, sheep, goat, cow, cat, guinea pig or rodent. The term does not denote a particular age or sex. Thus, adult and newborn subjects, as well as fetuses, whether male or female, are intended to be covered. In one aspect, the subject is a mammal. A patient refers to a subject afflicted with a disease or disorder.

The terms "prophylactic" or "therapeutic" treatment is art-recognized and includes administration to the host of one or more of the subject compositions. If it is administered prior to clinical manifestation of the unwanted condition (e.g., disease or other unwanted state of the host animal such as, but not limited to, myelination disturbances, myelin deficiencies, myelin loss and ineffective myelin repair) then the treatment is prophylactic, i.e., it protects the host against developing the unwanted condition, whereas if it is administered after manifestation of the unwanted condition, the treatment is therapeutic (i.e., it is intended to diminish, ameliorate, or stabilize the existing unwanted condition or side effects thereof).

The terms "therapeutic agent", "drug", "medicament" and "bioactive substance" are art-recognized and include molecules and other agents that are biologically, physiologically, or pharmacologically active substances that act locally or systemically in a patient or subject to treat a disease or condition. The terms include without limitation pharmaceutically acceptable salts thereof and prodrugs. Such agents may be acidic, basic, or salts; they may be neutral molecules, polar molecules, or molecular complexes capable of hydrogen bonding; they may be prodrugs in the form of ethers, esters, amides and the like that are biologically activated when administered into a patient or subject.

The phrase "therapeutically effective amount" or "pharmaceutically effective amount" is an art-recognized term. In certain embodiments, the term refers to an amount of a therapeutic agent that produces some desired effect at a reasonable benefit/risk ratio applicable to any medical treatment. In certain embodiments, the term refers to that amount necessary or sufficient to eliminate, reduce or maintain a target of a particular therapeutic regimen. The effective amount may vary depending on such factors as the disease or condition being treated, the particular targeted constructs being administered, the size of the subject or the severity of the disease or condition. One of ordinary skill in the art may empirically determine the effective amount of a particular compound without necessitating undue experimentation. In certain embodiments, a therapeutically effective amount of a therapeutic agent for in vivo use will likely depend on a number of factors, including: the rate of release of an agent from a polymer matrix, which will depend in part on the chemical and physical characteristics of the polymer; the identity of the agent; the mode and method of administration; and any other materials incorporated in the polymer matrix in addition to the agent.

The term "ED50" is art-recognized. In certain embodiments, ED50 means the dose of a drug, which produces 50% of its maximum response or effect, or alternatively, the dose, which produces a pre-determined response in 50% of test subjects or preparations. The term "LD50" is art-recognized. In certain embodiments, LD50 means the dose of a drug, which is lethal in 50% of test subjects. The term "therapeutic index" is an art-recognized term, which refers to the therapeutic index of a drug, defined as LD50/ED50.

The terms "$IC_{50}$," or "half maximal inhibitory concentration" is intended to refer to the concentration of a substance (e.g., a compound or a drug) that is required for 50% inhibition of a biological process, or component of a process, including a protein, subunit, organelle, ribonucleoprotein, etc.

With respect to any chemical compounds, the present application is intended to include all isotopes of atoms occurring in the present compounds. Isotopes include those atoms having the same atomic number but different mass numbers. By way of general example and without limitation, isotopes of hydrogen include tritium and deuterium, and isotopes of carbon include C-13 and C-14.

When a bond to a substituent is shown to cross a bond connecting two atoms in a ring, then such substituent can be bonded to any atom in the ring. When a substituent is listed without indicating the atom via which such substituent is bonded to the rest of the compound of a given formula, then such substituent can be bonded via any atom in such substituent. Combinations of substituents and/or variables are permissible, but only if such combinations result in stable compounds.

When an atom or a chemical moiety is followed by a subscripted numeric range (e.g., $C_{1-6}$), it is meant to encompass each number within the range as well as all intermediate ranges. For example, "$C_{1-6}$ alkyl" is meant to include alkyl groups with 1, 2, 3, 4, 5, 6, 1-6, 1-5, 1-4, 1-3, 1-2, 2-6, 2-5, 2-4, 2-3, 3-6, 3-5, 3-4, 4-6, 4-5, and 5-6 carbons.

The term "alkyl" is intended to include both branched (e.g., isopropyl, tert-butyl, isobutyl), straight-chain e.g., methyl, ethyl, propyl, butyl, pentyl, hexyl, heptyl, octyl, nonyl, decyl), and cycloalkyl (e.g., alicyclic) groups (e.g., cyclopropyl, cyclopentyl, cyclohexyl, cycloheptyl, cyclooctyl), alkyl substituted cycloalkyl groups, and cycloalkyl substituted alkyl groups. Such aliphatic hydrocarbon groups have a specified number of carbon atoms. For example, $C_{1-6}$ alkyl is intended to include $C_1$, $C_2$, $C_3$, $C_4$, $C_5$, and $C_6$ alkyl groups. As used herein, "lower alkyl" refers to alkyl groups having from 1 to 6 carbon atoms in the backbone of the carbon chain. "Alkyl" further includes alkyl groups that have oxygen, nitrogen, sulfur or phosphorous atoms replacing one or more hydrocarbon backbone carbon atoms. In certain embodiments, a straight chain or branched chain alkyl has six or fewer carbon atoms in its backbone (e.g., $C_1$-$C_6$ for straight chain, $C_3$-$C_6$ for branched chain), for example four or fewer. Likewise, certain cycloalkyls have from three to eight carbon atoms in their ring structure, such as five or six carbons in the ring structure.

The term "alkenyl" refers to a linear, branched or cyclic hydrocarbon group of 2 to about 24 carbon atoms containing at least one double bond, such as ethenyl, n-propenyl, isopropenyl, n-butenyl, isobutenyl, octenyl, decenyl, tetradecenyl, hexadecenyl, eicosenyl, tetracosenyl, cyclopentenyl, cyclohexenyl, cyclooctenyl, and the like. Generally, although again not necessarily, alkenyl groups can contain 2 to about 18 carbon atoms, and more particularly 2 to 12 carbon atoms. The term "lower alkenyl" refers to an alkenyl group of 2 to 6 carbon atoms, and the specific term "cycloalkenyl" intends a cyclic alkenyl group, preferably having 5 to 8 carbon atoms. The term "substituted alkenyl" refers to alkenyl substituted with one or more substituent groups, and the terms "heteroatom-containing alkenyl" and "heteroalkenyl" refer to alkenyl or heterocycloalkenyl (e.g., heterocylcohexenyl) in which at least one carbon atom is replaced with a heteroatom. If not otherwise indicated, the terms "alkenyl" and "lower alkenyl" include linear, branched, cyclic, unsubstituted, substituted, and/or heteroatom-containing alkenyl and lower alkenyl, respectively.

The term "alkynyl" refers to a linear or branched hydrocarbon group of 2 to 24 carbon atoms containing at least one triple bond, such as ethynyl, n-propynyl, and the like. Generally, although again not necessarily, alkynyl groups can contain 2 to about 18 carbon atoms, and more particularly can contain 2 to 12 carbon atoms. The term "lower alkynyl" intends an alkynyl group of 2 to 6 carbon atoms. The term "substituted alkynyl" refers to alkynyl substituted with one or more substituent groups, and the terms "heteroatom-containing alkynyl" and "heteroalkynyl" refer to alkynyl in which at least one carbon atom is replaced with a heteroatom. If not otherwise indicated, the terms "alkynyl" and "lower alkynyl" include linear, branched, unsubstituted, substituted, and/or heteroatom-containing alkynyl and lower alkynyl, respectively.

The terms "alkyl", "alkenyl", and "alkynyl" are intended to include moieties which are diradicals, i.e., having two points of attachment. A nonlimiting example of such an alkyl moiety that is a diradical is —$CH_2CH_2$—, i.e., a $C_2$ alkyl group that is covalently bonded via each terminal carbon atom to the remainder of the molecule.

The term "alkoxy" refers to an alkyl group bound through a single, terminal ether linkage; that is, an "alkoxy" group may be represented as —O-alkyl where alkyl is as defined above. A "lower alkoxy" group intends an alkoxy group containing 1 to 6 carbon atoms, and includes, for example, methoxy, ethoxy, n-propoxy, isopropoxy, t-butyloxy, etc. Preferred substituents identified as "$C_1$-$C_6$ alkoxy" or "lower alkoxy" herein contain 1 to 3 carbon atoms, and particularly preferred such substituents contain 1 or 2 carbon atoms (i.e., methoxy and ethoxy).

The term "aryl" refers to an aromatic substituent containing a single aromatic ring or multiple aromatic rings that are fused together, directly linked, or indirectly linked (such that the different aromatic rings are bound to a common group such as a methylene or ethylene moiety). Aryl groups can contain 5 to 20 carbon atoms, and particularly preferred aryl groups can contain 5 to 14 carbon atoms. Examples of aryl groups include benzene, phenyl, pyrrole, furan, thiophene, thiazole, isothiazole, imidazole, triazole, tetrazole, pyrazole, oxazole, isooxazole, pyridine, pyrazine, pyridazine, and pyrimidine, and the like. Furthermore, the term "aryl" includes multicyclic aryl groups, e.g., tricyclic, bicyclic, e.g., naphthalene, benzoxazole, benzodioxazole, benzothiazole, benzoimidazole, benzothiophene, methylenedioxyphenyl, quinoline, isoquinoline, napthridine, indole, benzofuran, purine, benzofuran, deazapurine, or indolizine. Those aryl groups having heteroatoms in the ring structure may also be referred to as "aryl heterocycles", "heterocycles," "heteroaryls" or "heteroaromatics". The aromatic ring can be substituted at one or more ring positions with such substituents as described above, as for example, halogen, hydroxyl, alkoxy, alkylcarbonyloxy, arylcarbonyloxy, alkoxycarbonyloxy, aryloxycarbonyloxy, carboxylate, alkylcarbonyl, alkylaminocarbonyl, aralkylaminocarbonyl, alkenylaminocarbonyl, alkylcarbonyl, arylcarbonyl, aralkylcarbonyl, alkenylcarbonyl, alkoxycarbonyl, aminocarbonyl, alkylthiocarbonyl, phosphate, phosphonato, phosphinato, cyano, amino (including alkylamino, dialkylamino, arylamino, diaryl amino, and al kylaryl amino), acylamino (including alkylcarbonylamino, arylcarbonylamino, carbamoyl and ureido), amidino, imino, sulfhydryl, alkylthio, arylthio, thiocarboxylate, sulfates, alkylsulfinyl, sulfonato, sulfamoyl, sulfonamido, nitro, trifluoromethyl, cyano, azido, heterocyclyl, alkylaryl, or an aromatic or heteroaromatic moiety. Aryl groups can also be fused or bridged with alicyclic or heterocyclic rings, which are not aromatic so as to form a multicyclic system (e.g., tetralin, methylenedioxyphenyl). If not otherwise indicated, the term "aryl" includes unsubstituted, substituted, and/or heteroatom-containing aromatic substituents.

The term "alkaryl" refers to an aryl group with an alkyl substituent, and the term "aralkyl" refers to an alkyl group with an aryl substituent, wherein "aryl" and "alkyl" are as defined above. Exemplary aralkyl groups contain 6 to 24 carbon atoms, and particularly preferred aralkyl groups contain 6 to 16 carbon atoms. Examples of aralkyl groups include, without limitation, benzyl, 2-phenyl-ethyl, 3-phenyl-propyl, 4-phenyl-butyl, 5-phenyl-pentyl, 4-phenylcyclohexyl, 4-benzylcyclohexyl, 4-phenylcyclohexylmethyl, 4-benzylcyclohexylmethyl, and the like. Alkaryl groups include, for example, p-methylphenyl, 2,4-dimethylphenyl, p-cyclohexylphenyl, 2,7-dimethylnaphthyl, 7-cyclooctylnaphthyl, 3-ethyl-cyclopenta-1,4-diene, and the like.

The terms "heterocyclyl" or "heterocyclic group" include closed ring structures, e.g., 3- to 10-, or 4- to 7-membered rings, which include one or more heteroatoms. "Heteroatom" includes atoms of any element other than carbon or hydrogen. Examples of heteroatoms include nitrogen, oxygen, sulfur and phosphorus.

Heterocyclyl groups can be saturated or unsaturated and include pyrrolidine, oxolane, thiolane, piperidine, piperazine, morpholine, lactones, lactams, such as azetidinones and pyrrolidinones, sultams, and sultones. Heterocyclic groups such as pyrrole and furan can have aromatic character. They include fused ring structures, such as quinoline and isoquinoline. Other examples of heterocyclic groups include pyridine and purine. The heterocyclic ring can be substituted at one or more positions with such substituents as described above, as for example, halogen, hydroxyl, alkylcarbonyloxy, arylcarbonyloxy, alkoxycarbonyloxy, aryloxycarbonyloxy, carboxylate, alkylcarbonyl, alkoxycarbonyl, aminocarbonyl, alkylthiocarbonyl, alkoxyl, phosphate, phosphonato, phosphinato, cyano, amino (including alkyl amino, dialkylamino, arylamino, diarylamino, and alkylarylamino), acylamino (including alkylcarbonylamino, arylcarbonylamino, carbamoyl and ureido), amidino, imino, sulfhydryl, alkylthio, arylthio, thiocarboxylate, sulfates, sulfonato, sulfamoyl, sulfonamido, nitro, trifluoromethyl, cyano, azido, heterocyclyl, or an aromatic or heteroaromatic moiety. Heterocyclic groups can also be substituted at one or more constituent atoms with, for example, a lower alkyl, a lower alkenyl, a lower alkoxy, a lower alkylthio, a lower alkylamino, a lower alkylcarboxyl, a nitro, a hydroxyl, —$CF_3$, or —CN, or the like.

The term "halo" or "halogen" refers to fluoro, chloro, bromo, and iodo. "Counterion" is used to represent a small, negatively charged species such as fluoride, chloride, bromide, iodide, hydroxide, acetate, and sulfate.

The terms "substituted" as in "substituted alkyl," "substituted aryl," and the like, as alluded to in some of the aforementioned definitions, is meant that in the alkyl, aryl, or other moiety, at least one hydrogen atom bound to a carbon (or other) atom is replaced with one or more non-hydrogen substituents. Examples of such substituents include, without limitation: functional groups such as halo, hydroxyl, silyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl (including $C_2$-$C_{24}$ alkylcarbonyl (—CO-alkyl) and $C_6$-$C_{20}$ arylcarbonyl (—CO-aryl)), acyloxy (—O-acyl), $C_2$-$C_{24}$ alkoxycarbonyl (—(CO)—O-alkyl), $C_6$-$C_{20}$ aryloxycarbonyl (—(CO)—O-aryl), $C_2$-$C_{24}$ alkylcarbonato (—O—(CO)—O-alkyl), $C_6$-$C_{20}$ arylcarbonato (—O—(CO)—O-aryl), carboxy (—COOH), carboxylato (—COO—), carbamoyl (—(CO)—$NH_2$), mono-($C_1$-$C_{24}$ alkyl)-substituted carbamoyl (—(CO)—NH($C_1$-$C_{24}$ alkyl)), di-($C_1$-$C_4$ alkyl)-substituted carbamoyl (—(CO)—N($C_1$-$C_{24}$ alkyl)$_2$), mono-substituted arylcarbamoyl (—(CO)—NH-aryl), thiocarbamoyl (—(CS)—NH$_2$), carbamido (—NH—(CO)—NH$_2$), cyano (—CN), isocyano (—N$^+$C$^-$), cyanato (—O—CN), isocyanato (—ON$^+$C$^-$), isothiocyanato (—S—CN), azido (—N=N$^+$=N$^-$), formyl (—(CO)—H), thioformyl (—(CS)—H), amino (—NH$_2$), mono- and di-(C$_1$-C$_{24}$ alkyl)-substituted amino, mono- and di-(C$_5$-C$_2$O aryl)-substituted amino, C$_2$-C$_{24}$ alkylamido (—NH—(CO)-alkyl), C$_6$-C$_{20}$ arylamido (—NH—(CO)-aryl), imino (—CR=NH where R=hydrogen, C$_1$-C$_{24}$ alkyl, C$_5$-C$_{20}$ aryl, C$_6$-C$_{24}$ alkaryl, C$_6$-C$_{24}$ aralkyl, etc.), alkylimino (—CR=N(alkyl), where R=hydrogen, alkyl, aryl, alkaryl, etc.), arylimino (—CR=N (aryl), where R=hydrogen, alkyl, aryl, alkaryl, etc.), nitro (—NO$_2$), nitroso (—NO), sulfo (—SO$_2$—OH), sulfonato (—SO$_2$—O—), C$_1$-C$_{24}$ alkylsulfanyl (—S-alkyl; also termed "alkylthio"), arylsulfanyl (—S-aryl; also termed "arylthio"), C$_1$-C$_{24}$ alkylsulfinyl (—(SO)-alkyl), C$_5$-C$_{20}$ arylsulfinyl (—(SO)-aryl), C$_1$-C$_{24}$ alkylsulfonyl (—SO$_2$-alkyl), C$_5$-C$_{20}$ arylsulfonyl (—SO$_2$-aryl), phosphono (—P (O)(OH)$_2$), phosphonato (—P(O)(O$^-$)$_2$), phosphinato (—P (O)(O$^-$)), phospho (—PO$_2$), and phosphino (—PH$_2$); and the hydrocarbyl moieties C$_1$-C$_{24}$ alkyl, C$_2$-C$_{24}$ alkenyl, C$_2$-C$_{24}$ alkynyl, C$_5$-C$_{20}$ aryl, C$_6$-C$_{24}$ alkaryl, and C$_6$-C$_{24}$ aralkyl.

In addition, the aforementioned functional groups may, if a particular group permits, be further substituted with one or more additional functional groups or with one or more hydrocarbyl moieties such as those specifically enumerated above. Analogously, the above-mentioned hydrocarbyl moieties may be further substituted with one or more functional groups or additional hydrocarbyl moieties such as those specifically enumerated.

When the term "substituted" appears prior to a list of possible substituted groups, it is intended that the term apply to every member of that group. For example, the phrase "substituted alkyl, alkenyl, and aryl" is to be interpreted as "substituted alkyl, substituted alkenyl, and substituted aryl." Analogously, when the term "heteroatom-containing" appears prior to a list of possible heteroatom-containing groups, it is intended that the term apply to every member of that group. For example, the phrase "heteroatom-containing alkyl, alkenyl, and aryl" is to be interpreted as "heteroatom-containing alkyl, substituted alkenyl, and substituted aryl."

"Optional" or "optionally" means that the subsequently described circumstance may or may not occur, so that the description includes instances where the circumstance occurs and instances where it does not. For example, the phrase "optionally substituted" means that a non-hydrogen substituent may or may not be present on a given atom, and, thus, the description includes structures wherein a non-hydrogen substituent is present and structures wherein a non-hydrogen substituent is not present.

The terms "stable compound" and "stable structure" are meant to indicate a compound that is sufficiently robust to survive isolation, and as appropriate, purification from a reaction mixture, and formulation into an efficacious therapeutic agent.

The terms "free compound" is used herein to describe a compound in the unbound state.

Throughout the description, where compositions are described as having, including, or comprising, specific components, it is contemplated that compositions also consist essentially of, or consist of, the recited components. Similarly, where methods or processes are described as having, including, or comprising specific process steps, the processes also consist essentially of, or consist of, the recited processing steps. Further, it should be understood that the order of steps or order for performing certain actions is immaterial so long as the compositions and methods described herein remains operable. Moreover, two or more steps or actions can be conducted simultaneously.

The term "small molecule" is an art-recognized term. In certain embodiments, this term refers to a molecule, which has a molecular weight of less than about 2000 amu, or less than about 1000 amu, and even less than about 500 amu.

All percentages and ratios used herein, unless otherwise indicated, are by weight.

Embodiments described herein relate to compounds and methods of treating retinal degeneration associated with inherited rhodopsin protein misfolding mutations in the ocular tissue of a subject. It is believed that thermal- or photo-bleached rhodopsin mutations (e.g., P23H rhodopsin mutation) in the apo opsin form aggregates in situ, disrupting the disc organization of the rod outer segment (ROS), thereby compromising photoreceptor cell survival. The compounds described herein are small molecules that can act or behave as chaperones of rhodopsin and can have micromolar potency and efficacy equal or greater than 9-cis-retinal. The compounds described herein can potentially stabilize mutant rhodopsin in photoreceptor cells, and rescue the transport and glycosylation of unstable mutant opsin from the endoplasmic reticulum (ER) to the plasma membrane, thereby restoring rhodopsin homeostasis and preventing photoreceptor death related to retinal degeneration.

In some embodiments, a method of treating the retinal degeneration in a subject can include administering to the subject a therapeutically effective amount of a small molecule chaperone of rhodopsin. The small molecule chaperone of rhodopsin can include a compound of formula (I):

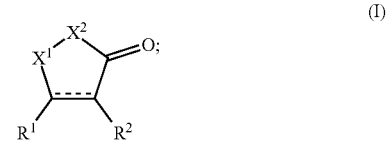

wherein X$^1$ is CH$_2$, C=O, N—R$^3$;
wherein X$^2$ is O or N—R$^4$.
wherein R$^1$ and R$^2$ are each independently selected from the group consisting of hydrogen, a substituted or unsubstituted cycloalkyl, heterocyclyl, aryl, and heteroaryl, wherein at least one of R$^1$ or R$^2$ is not H;
wherein R$^3$ and R$^4$ are each independently selected from the group consisting of hydrogen, a substituted or unsubstituted C$_1$-C$_{24}$ alkyl, C$_2$-C$_{24}$ alkenyl, C$_2$-C$_{24}$ alkynyl, C$_3$-C$_{20}$ aryl, heteroaryl, heterocycloalkenyl containing from 5-6 ring atoms (wherein from 1-3 of the ring atoms is independently selected from N, NH, N(C$_1$-C$_6$ alkyl), NC(O)(C$_1$-C$_6$ alkyl), O, and S), C$_6$-C$_{24}$ alkaryl, C$_6$-C$_{24}$ aralkyl, halo, —Si(C$_1$-C$_3$ alkyl)$_3$, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl, acyloxy, C$_2$-C$_{24}$ alkoxycarbonyl, C$_6$-C$_{20}$ aryloxycarbonyl, C$_2$-C$_{24}$ alkylcarbonato, C$_6$-C$_{20}$ arylcarbonato, carboxy, carboxylato, carbamoyl, C$_1$-C$_{24}$ alkyl-carbamoyl, arylcarbamoyl, thiocarbamoyl, carbamido, cyano, isocyano, cyanato, isocyanato, isothiocyanato, azido, formyl, thioformyl, amino, C$_1$-C$_{24}$ alkyl amino, C$_5$-C$_{20}$ aryl amino, C$_2$-C$_{24}$ alkylamido, C$_6$-C$_{20}$ arylamido, imino, alkylimino, arylimino, nitro, nitroso, sulfo, sulfonato, C$_1$-C$_{24}$ alkylsulfanyl, arylsulfanyl, C$_1$-C$_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof;

and pharmaceutically acceptable salts thereof.

In some embodiments, the small molecule chaperone of rhodopsin can include a compound of formula (II):

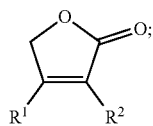

(II)

wherein $R^1$ and $R^2$ are each independently selected from the group consisting of hydrogen a substituted or unsubstituted cycloalkyl, heterocyclyl, aryl, and heteroaryl, wherein at least one of $R^1$ or $R^2$ is

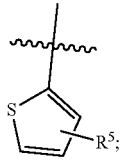

wherein $R^5$ is hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof;

and pharmaceutically acceptable salts thereof.

In some embodiments, the small molecule chaperone of rhodopsin can include a compound of formula (III):

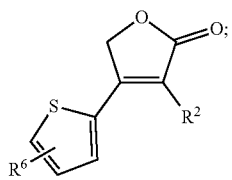

(III)

wherein $R^2$ and $R^6$ are each individually hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof;

and pharmaceutically acceptable salts thereof.

In other embodiments, the small molecule chaperone of rhodopsin can include a compound of formula (IV):

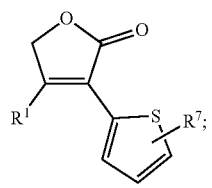

(IV)

wherein $R^2$ and $R^7$ are each individually hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, arylcarbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof;

and pharmaceutically acceptable salts thereof.

Examples of compounds for use in the methods described herein can include compounds having the following formulas selected from the group consisting of:

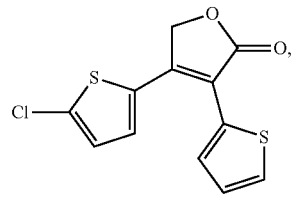

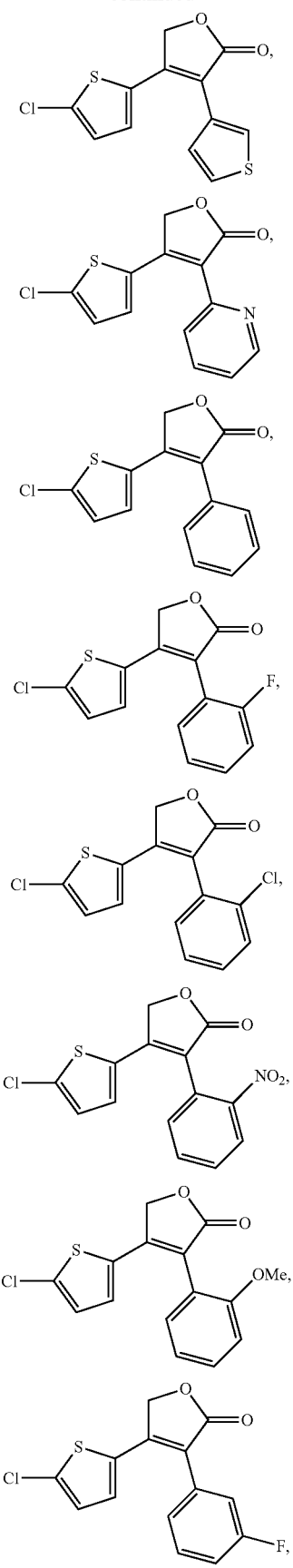
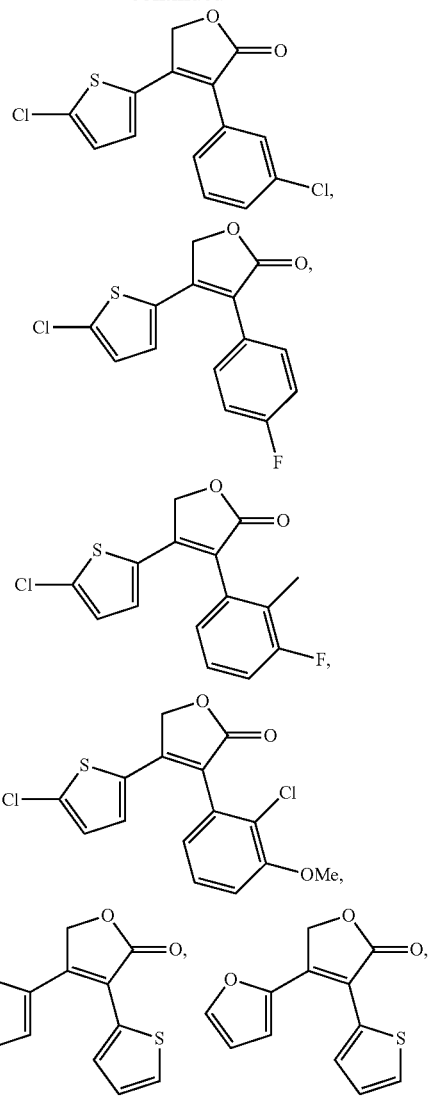
and pharmaceutically acceptable salts thereof.
Other examples of compounds for use in the methods described herein can include compounds having the following formulas selected from the group consisting of:
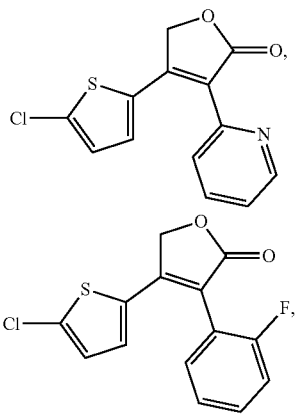

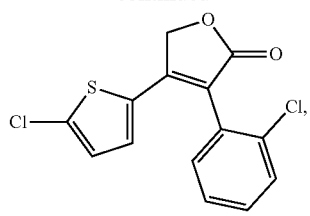
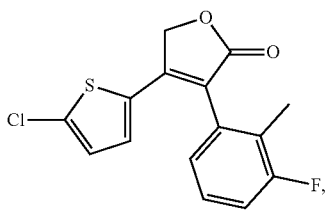
and pharmaceutically acceptable salts thereof.
Additional examples of compounds for use in the methods described herein can include compounds having the following formulas selected from the group consisting of:
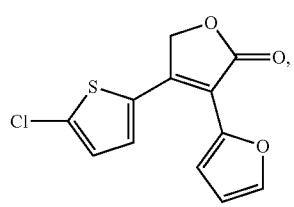
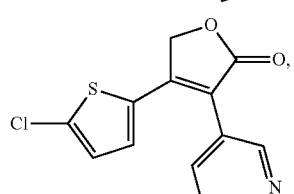
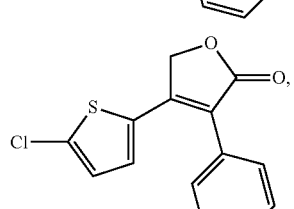
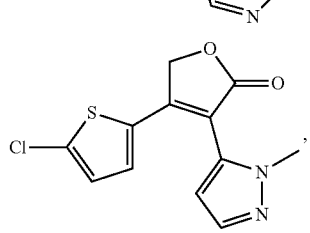
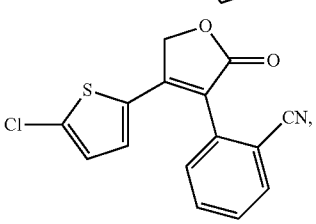
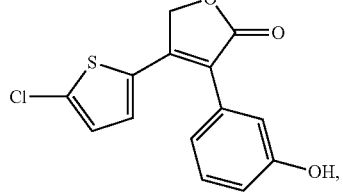
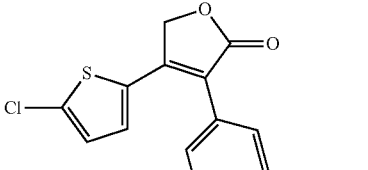
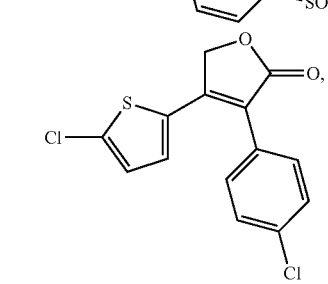
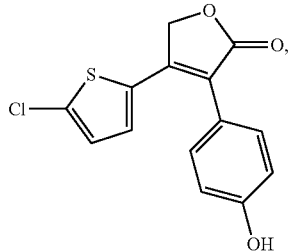
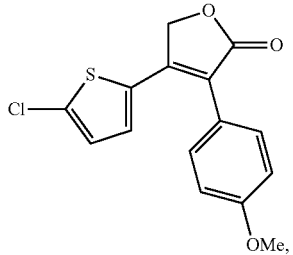
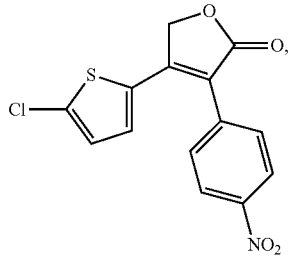
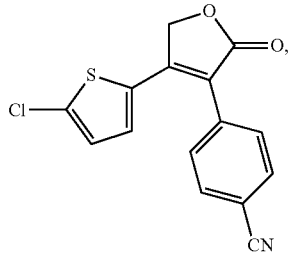

-continued
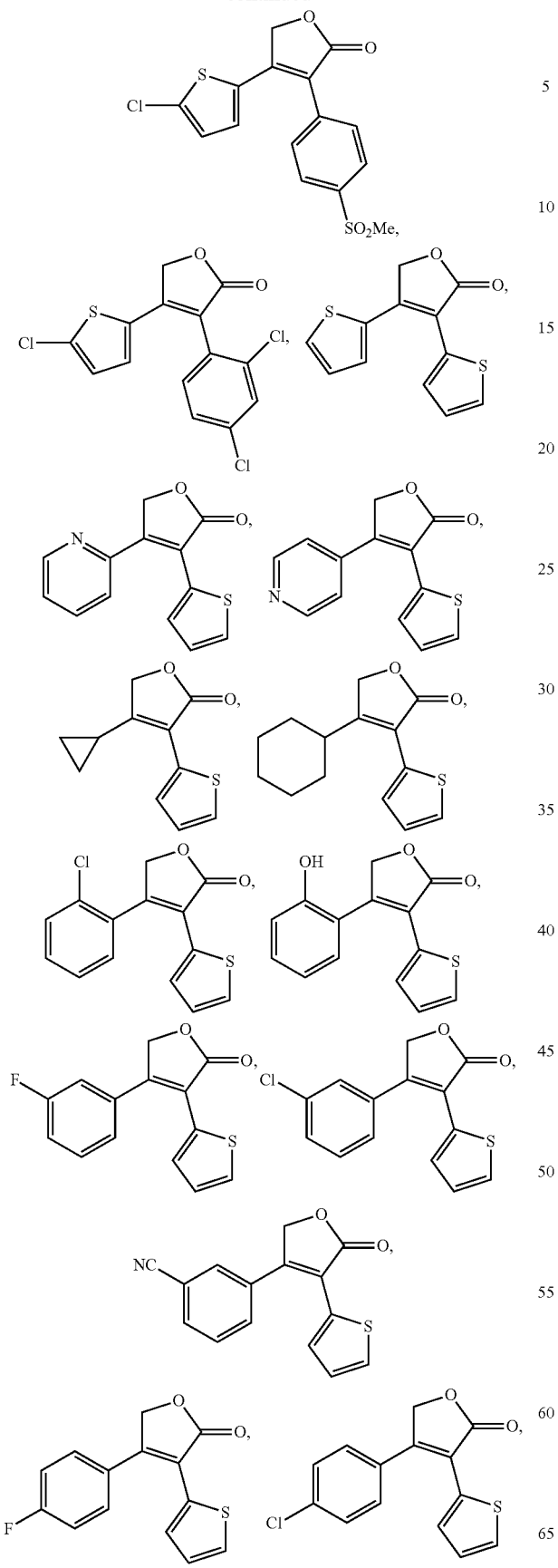
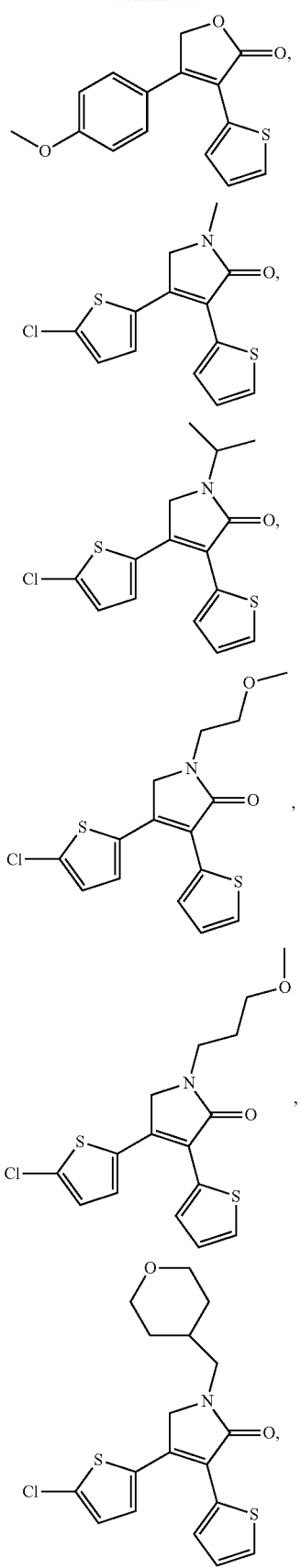

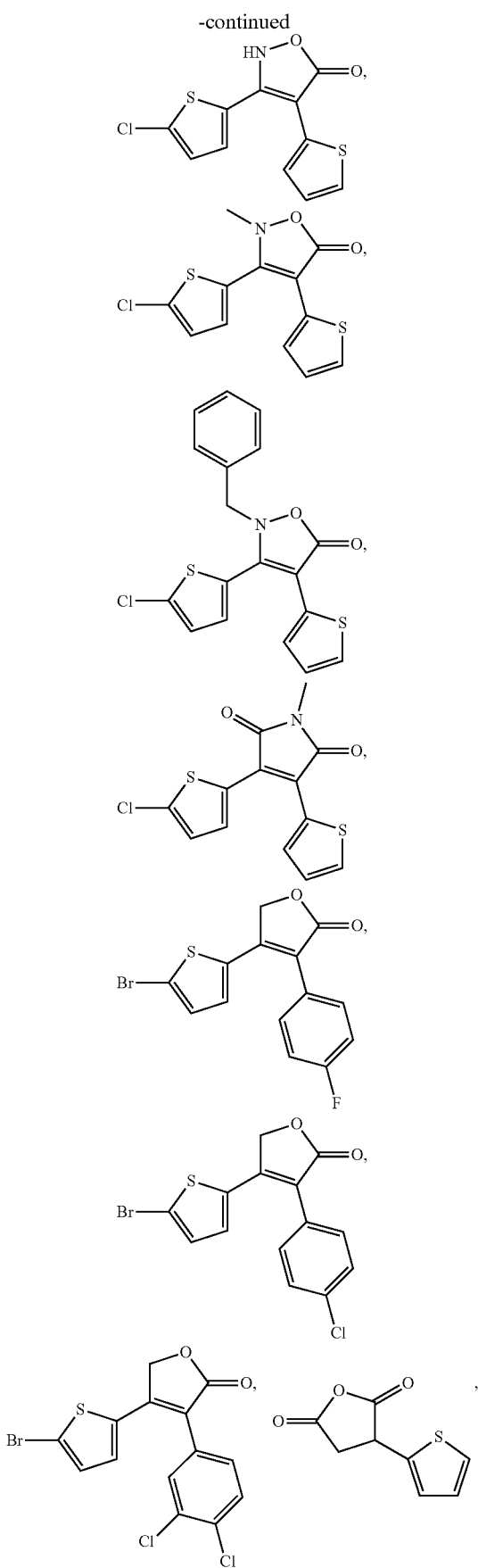

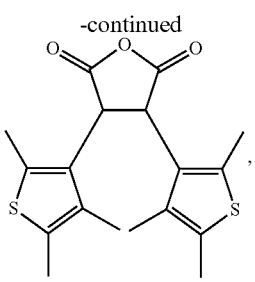

and pharmaceutically acceptable salts thereof.

Additional compounds for use in the methods described herein can be generated by further modifications to compound having the following formula (V):

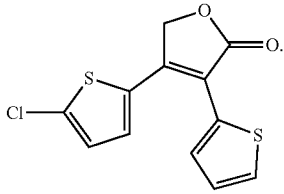

(V)

For example, additional compounds for use in a method described herein can be generated by modifying the furan-2(5H)-one ring, modifying the $C_3$ linkage of the furan-2(5H)-one ring of, and/or modifying the $C_4$ linkage of the furan-2(5H)-one ring of the compound having formula (V).

Candidate compound activity can be tested using the beta-galactosidase fragment complementation assay to measure and/or quantify the rescue of P23H opsin from ER to plasma membrane. Activity scores can be normalized with the effect from treatment with 5 µM 9-cis-retinal. In certain embodiments, effective compounds exhibit an efficacy higher than 20%.

Compounds described herein may be synthesized using standard synthetic techniques known to those of skill in the art or using methods known in the art in combination with methods described herein. In additions, solvents, temperatures and other reaction conditions presented herein may vary according to the practice and knowledge of those of skill in the art. Exemplary methods of synthesizing small molecule chaperone of rhodopsin compounds for use in a method described herein are illustrated in schemes 1-6 in the Example below.

The starting material used for the synthesis of compounds described herein can be obtained from commercial sources, such as Aldrich Chemical Co. (Milwaukee, Wis.), Sigma Chemical Co. (St. Louis, Mo.), or the starting materials can be synthesized. The compounds described herein, and other related compounds having different substituents can be synthesized using techniques and materials known to those of skill in the art, such as described, for example, in March, ADVANCED ORGANIC CHEMISTRY $4^{th}$ Ed., (Wiley 1992); Carey and Sundberg, ADVANCED ORGANIC CHEMISTRY $4^{th}$ Ed., Vols. A and B (Plenum 2000, 2001), and Green and Wuts, PROTECTIVE GROUPS IN ORGANIC SYNTHESIS $3^{rd}$ Ed., (Wiley 1999) (all of which are incorporated by reference in their entirety).

The compounds described herein can be provided and administered in the form of pharmaceutical compositions for the in vivo administration and inhibition of photoreceptor cell death in a subject. The pharmaceutical compositions can be administered to any subject that can experience the beneficial effects of the compounds described herein. Foremost among such animals are humans, although the present invention is not intended to be so limited.

The compounds used in methods described herein can be administered to the subject to treat retinal degeneration (e.g., retinal degeneration associated with rhodopsin mutations) using standard delivery methods including, for example, ophthalmic, topical, parenteral, subcutaneous, intravenous, intraarticular, intrathecal, intramuscular, intraperitoneal, intradermal injections, or by transdermal, buccal, oromucosal, oral routes or via inhalation. The particular approach and dosage used for a particular subject depends on several factors including, for example, the general health, weight, and age of the subject. Based on factors such as these, a medical practitioner can select an appropriate approach to treatment.

"Treating" or "treatment" as used herein, refers to the reduction in severity and/or frequency of symptoms, elimination of symptoms and/or underlying cause, prevention of the occurrence of symptoms and/or their underlying cause, and improvement or remediation of disease. Such treatment need not necessarily completely ameliorate the disease. For example, treatment of a subject with retinal degeneration by administration of the compounds described herein can encompass inhibiting or causing regression of the disease. Further, such treatment can be used in conjunction with other traditional treatments for retinal degeneration known to those of skill in the art.

Treatment according to the method described herein can be altered, stopped, or re-initiated in a subject depending on the status of ocular disorder. Treatment can be carried out as intervals determined to be appropriate by those skilled in the art. For example, the administration can be carried out 1, 2, 3, or 4 times a day. In some embodiments, the compounds can be administered after induction of retinal degeneration has occurred.

The treatment methods can include administering to the subject a therapeutically effective amount of a compound described herein. Pharmaceutical compositions for use in the methods described herein can have a therapeutically effective amount of the compound or salts thereof in a dosage in the range of 0.01 to 1,000 mg/kg of body weight of the subject, and more preferably in the range of from about 10 to 100 mg/kg of body weight of the patient.

The overall dosage will be a therapeutically effective amount depending on several factors including the overall health of a subject, the subject's disease state, severity of the condition, the observation of improvements and the formulation and route of administration of the selected agent(s). Determination of a therapeutically effective amount is within the capability of those skilled in the art. The exact formulation, route of administration and dosage can be chosen by the individual physician in view of the subject's condition.

The "therapeutically effective amount" of compounds and salts thereof used in the methods of the present invention varies depending upon the manner of administration, the age and body weight of the subject, and the condition of the subject to be treated, and ultimately will be decided by those skilled in the art. The term "therapeutically effective amount" refers to an amount (dose) effective in treating a subject, having, for example, retinal degeneration related disease or disorder (e.g. retinitis pigmentosa).

In some embodiments, the therapeutically effective amount of a compound described herein is the amount effective to: inhibit photoreceptor cell death in the subject; promote rod photoreceptor cell homeostasis in the subject inhibit early ER associated protein degradation (ERAD) pathway in photoreceptor cells of the subject; mobilize the P23H opsin from the endoplasmic reticulum to the plasma membrane of photoreceptor cells; stabilize the P23H rod opsin mutant protein in a subject; and/or inhibit bright light-induced retinal degeneration in a $Rdh8^{-/-}$-$Abca4^{-/-}$ mouse.

Formulation of the pharmaceutical compounds for use in the modes of administration noted above (and others) are known in the art and are described, for example, in Remington's Pharmaceutical Sciences (18th edition), ed. A. Gennaro, 1990, Mack Publishing Company, Easton, Pa. (also see, e.g., M. J. Rathbone, ed., Oral Mucosal Drug Delivery, Drugs and the Pharmaceutical Sciences Series, Marcel Dekker, Inc., N.Y., U.S.A., 1996; M. J. Rathbone et al., eds., Modified-Release Drug Delivery Technology, Drugs and the Pharmaceutical Sciences Series, Marcel Dekker, Inc., N.Y., U.S.A., 2003; Ghosh et al., eds., Drug Delivery to the Oral Cavity, Drugs and the Pharmaceutical Sciences Series, Marcel Dekker, Inc., N.Y., U.S.A., 2005; and Mathiowitz et al., eds., Bioadhesive Drug Delivery Systems, Drugs and the Pharmaceutical Sciences Series, Marcel Dekker, Inc., N.Y., U.S.A., 1999. Compounds of the invention can be formulated into pharmaceutical compositions containing pharmaceutically acceptable non-toxic excipients and carriers. The excipients are all components present in the pharmaceutical formulation other than the active ingredient or ingredients. Suitable excipients and carriers can be composed of materials that are considered safe and effective and may be administered to an individual without causing undesirable biological side effects, or unwanted interactions with other medications. Suitable excipients and carriers are those, which are composed of materials that will not affect the bioavailability and performance of the agent. As generally used herein "excipient" includes, but is not limited to surfactants, emulsifiers, emulsion stabilizers, emollients, buffers, solvents, dyes, flavors, binders, fillers, lubricants, and preservatives. Suitable excipients include those generally known in the art such as the "Handbook of Pharmaceutical Excipients", 4th Ed., Pharmaceutical Press, 2003.

In one example, a compound described herein can be provided in an ophthalmic preparation that can be administered to the subject's eye. The ophthalmic preparation can contain the compound in a pharmaceutically acceptable solution, suspension or ointment. Some variations in concentration will necessarily occur, depending on the particular compound employed, the condition of the subject to be treated and the like, and the person responsible for treatment will determine the most suitable concentration for the individual subject. The ophthalmic preparation can be in the form of a sterile aqueous solution containing, if desired, additional ingredients, for example, preservatives, buffers, tonicity agents, antioxidants, stabilizers, nonionic wetting or clarifying agents, and viscosity increasing agents.

Subjects affected with or at risk of retinal degeneration, which are not readily accessible or suitable for ophthalmic (e.g. eye-drops) and/or topical administration, can be treated by a systemic approach, such as intravenous infusion. For example, the compound can be administered at a low dosage by continuous intravenous infusion. In another example, in which a patient requires longer-term care, the compound can be administered intermittently (e.g., every 12-24 hours). In a variation of this approach, the initial or loading dose can be followed by maintenance doses that are less than, (e.g., half) the loading dose or by continuous infusion. The duration of such treatment can be determined by those having skill in the art, based on factors, for example, the severity of the condition and the observation of improvements.

When administering the compounds described herein to the subject by intravenous infusion, devices and equipment (e.g., catheters, such as central or peripheral venous catheters, tubing, drip chambers, flashback bulbs, injection Y sites, stopcocks, and infusion bags) can be used that are compatible with the compound.

The compounds can be administered to a subject to treat retinal degeneration in a subject. Retinal degeneration, as contemplated for treatment by the methods described herein, can include but is not limited to retinal degenerations associated with disrupted rhodopsin homeostasis and inherited retinal degeneration associated with rhodopsin mutations. In some embodiments, retinal degeneration selected from the group consisting of Leber congenital amaurosis, Stargardt disease, and retinitis pigmentosa.

One particular aspect of the present invention contemplates the treatment of retinitis pigmentosa in a subject. Retinitis pigmentosa as contemplated for treatment by methods of the present invention, can include but is not limited to autosomal dominate retinitis pigmentosa associated with a P23H RHO mutation.

In one embodiment, a subject is diagnosed as having symptoms of retinal degeneration (such as impaired vision, night blindness, retinal detachment, light sensitivity, tunnel vision, and loss of peripheral vision to total loss of vision), and then a disclosed compound is administered. In another embodiment, a subject may be identified as being at risk for developing retinal degeneration (risk factors may include family history or testing positive for a rhodopsin mutation), and then a disclosed compound is administered. In another embodiment, a subject may have retinal degeneration in both eyes, and then a disclosed compound is administered. In another embodiment, a subject may have retinal degeneration in one eye but not the other eye, and then a disclosed compound is administered to one or both eyes. In yet another embodiment, a subject may be diagnosed as having retinitis pigmentosa and then a disclosed compound is administered. In another embodiment, a subject is diagnosed as having symptoms of other forms of retinal degeneration whose etiology involves a rhodopsin mutation (e.g., a P23H rod opsin mutation) in photoreceptor cells of a subject, and then the compound is administered. In another embodiment, a subject may be identified as being at risk for developing other forms of retinal degeneration whose etiology a rhodopsin mutation) in photoreceptor cells, and then the disclosed compound is administered. In some embodiments, a compound is administered prophylactically. In some embodiments, a subject has been diagnosed as having the disease before retinal damage is apparent. In some embodiments, a human subject may know that he or she is in need of the retinal generation treatment or prevention.

In some embodiments, a subject may be monitored for the extent of retinal degeneration. A subject may be monitored in a variety of ways, such as by eye examination, dilated eye examination, fundoscopic examination, visual acuity test, and/or biopsy. Monitoring can be performed at a variety of times. For example, a subject may be monitored after a compound is administered. The monitoring can occur, for example, one day, one week, two weeks, one month, two months, six months, one year, two years, five years, or any other time period after the first administration of a compound. A subject can be repeatedly monitored. In some embodiments, the dose of a compound may be altered in response to monitoring.

Another strategy for treating a subject suffering from a retinal degeneration is to administer a therapeutically effective amount of a compound described herein along with a therapeutically effective amount of an additional compound that acts as a chaperone of rhodopsin and/or an anti-retinal degeneration agent or therapy. Examples of anti-retinal degeneration agents or therapies include but are not limited to supplements, such as vitamin A, DHA, and lutien, as well as optic prosthetic devices, gene therapy mechanisms and retinal sheet transplantations.

Therefore, in a further embodiment, the compounds described herein can be administered as part of a combination therapy with adjunctive therapies for treating retinal degeneration.

The phrase "combination therapy" embraces the administration of the compounds described herein and a therapeutic agent as part of a specific treatment regimen intended to provide a beneficial effect from the co-action of these therapeutic agents. When administered as a combination, the compounds, which act as a chaperone of rhodopsin, and a therapeutic agent can be formulated as separate compositions. Administration of these therapeutic agents in combination typically is carried out over a defined time period (usually minutes, hours, days or weeks depending upon the combination selected).

"Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. Sequential or substantially simultaneous administration of each therapeutic agent can be effected by any appropriate route including, but not limited to, oral routes, intravenous routes, intramuscular routes, and direct absorption through mucous membrane tissues. The therapeutic agents can be administered by the same route or by different routes. For example, a first therapeutic agent of the combination selected may be administered by intravenous injection while the other therapeutic agents of the combination may be administered orally. Alternatively, for example, all therapeutic agents may be administered orally or all therapeutic agents may be administered by intravenous injection. The sequence in which the therapeutic agents are administered is not narrowly critical. "Combination therapy" also can embrace the administration of the therapeutic agents as described above in further combination with other biologically active ingredients (such as, but not limited to, a second and different therapeutic agent) and non-drug therapies (e.g., optic prosthetic devices and retinal sheets).

In some embodiments, the compounds described herein can be administered in combination with an HDAC inhibitor. In some embodiments, an HDAC inhibitor can include short-chain fatty acids (e.g., Sodium Butyrate, Isovalerate, Valerate, 4-Phenylbutyrate (4-PBA), Phenylbutyrate (PB), Propionate, Butyramide, Isobutyramide, Phenylacetate, 3-Bromopropionate, Tributyrin, Valproic acid (Vpa), Valproate, Valproate semisodium and pivaloyloxymethyl butyrate (PIVANEX)).

In other embodiments, an HDAC inhibitor can include a hydroxamic acid derivative (e.g., suberoylanilide hydroxamic acid (SAHA, vorinostat), scriptaid, Trichostatin analogs such as Trichostatin A (TSA) and Trichostatin C, m-Carboxycinnamic acid bishydroxamide (CBHA), Pyroxamide, Salicylbishydroxamic acid, Suberoyl bishydroxamic acid (SBHA), Azelaic bishydroxamic acid (ABHA) Azelaic-1-hydroxamate-9-anilide (AAHA), 6-(3-Chlorophenylureido) carpoic hydroxamic acid (3Cl-UCHA), Oxamflatin [(2E)-5-[3-[(phenylsulfonyl) amino]phenyl]-pent-2-en-4-ynohydroxamic acid], A-161906 Scriptaid, PXD-101 (Prolifix), LAQ-824, CHAP, MW2796, MW2996; or any of the hydroxamic acids disclosed in U.S. Pat. Nos. 5,369,108, 5,932,616, 5,700,811, 6,087,367, and 6,511,990). In certain embodiments, the HDAC inhibitor is SAHA.

In still other embodiments, an HDAC inhibitor can include benzamide derivatives (e.g., CI-994; MS-275 [N-(2-aminophenyl)-4-[N-(pyridin-3-yl methoxycarbonyl)aminomethyl]benzamide] and 3'-amino derivative of MS-275).

In yet other embodiments, an HDAC inhibitor can include cyclic peptides (e.g., Trapoxin A (TPX)-cyclic tetrapeptide (cyclo-(L-phenylalanyl-L-phenylalanyl-D-pipecolinyl-L-2-amino-8-oxo-9,10-epoxy decanoyl)), FR901228 (FK 228, depsipeptide), FR225497 cyclic tetrapeptide, Apicidin cyclic tetrapeptide [cyclo(N—O-methyl-L-tryptophanyl-L-isoleucinyl-D-pipecolinyl-L-2-amino-8-oxodecanoyl)], Apicidin Ia, Apicidin Ib, Apicidin Ic, Apicidin IIa, and Apicidin IIb, CHAP, HC-toxin cyclic tetrapeptide, WF27082 cyclic tetrapeptide, and Chlamydocin.

Additional HDAC inhibitors can include natural products, such as psammaplins and Depudecin, Electrophilic ketone derivatives such as Trifluoromethyl ketones, α-keto amides such as N-methyl-α-ketoamides, LSD1 polypeptide, TNF-alpha (TNFα), an inducible transcription factor NF-AT (nuclear factor of activated T cells), and Anti-IκBα or IκBε agents.

The invention is further illustrated by the following example, which is not intended to limit the scope of the claims.

EXAMPLE

In this example, we identified small molecules that rescue the transport of P23H rod opsin. A novel pharmacological chaperone of rod opsin, YC-001, showed inverse agonist and non-competitive antagonist activities towards rod opsin. Just one preconditioning dose of YC-001 protected Abca4$^{-/-}$-Rdh8$^{-/-}$ mice from bright light-induced photoreceptor death, suggesting its broad application against retinal degeneration.

Methods
Stable Cell Lines

U2OS(PLC-EA/P23H-PK) cells. A U2OS stable cell line was generated by DiscoveRx, Inc. (Fremont, CA, USA) for the β-Gal fragment complementation assay used in the small molecule HTS for rescue of P23H opsin transport. U2OS cells that continually express P23H-PK and PLC-EA fusion proteins were generated. Briefly, this small subunit of R-Gal (PK fragment) was fused to the C-terminal of the mouse P23H opsin mutant, while the large EA fragment, a subunit of 1-Gal, was fused with PLC, a plasma membrane anchored peptide. Both constructs were subcloned by DicoveRx, Inc. and transferred into U2OS cells by viral infections. Positive clones were selected under treatment with hygromycin and geneticin. Expression of both fusion proteins was confirmed by immunostaining and immunoblots.

Three NIH3T3 stable cell lines, NIH3T3-(WT-opsin/GFP), NIH3T3-(P23H-opsin/GFP), and NIH3T3-(GFP) were previously generated which stably express mouse WT opsin and GFP; P23H opsin and GFP; and only GFP, respectively. GFP is expressed separately from opsin in these cell lines. NIH3T3 cells were from ATCC. DNA constructs for generating these stable cell lines were confirmed by Sanger sequencing. Expression of GFP was confirmed by green fluorescence imaging, and expression of P23H and WT opsin were confirmed by immunoblots.

Cell Culture and Media

Stable cell lines used in this study were cultured in Dulbecco's modified Eagle's medium (DMEM, Hyclone, Logan, UT, USA) with 10% fetal bovine serum (FBS; Hyclone) and 5 µg mL$^{-1}$ Plasmocin antimycoplasma reagent (InvivoGen, San Diego, CA, USA) at 37° C. in 5% $CO_2$. Cells were subcultured following the ATCC Animal Cell Culture Guide (www.atcc.org). When cells were seeded for assays in 96- or 384-well plates, they were cultured in medium containing 100 units mL$^{-1}$ penicillin, 100 µg mL$^{-1}$ streptomycin and 2.92 µg mL$^{-1}$ L-glutamine (Hyclone) along with appropriate assay components as described below.

Chemicals and Reagents

DDM (Affymetrix Inc., Maumee, OH, USA) was used to solubilize bovine opsin from ROS disc membranes. The β-Gal fragment complementation assay was performed with the Gal-Screen System (Applied Biosystem, Bedford, MA, USA). PNGaseF was purchased from NEB (Ipswich, MA, USA) for the deglycosylation of cell lysates. 4'6'-Diamidino-2-phenyl-indole (DAPI) and Hoechst33342 were purchased from Thermo Fisher Scientific (Grand Island, NY, USA) for nuclear staining. Cy3-conjugated goat anti-mouse secondary antibody was ordered from Jackson ImmunoResearch Laboratories, Inc. (catalogue number: 115-165-146, West Grove, PA, USA) for immunostaining. DMSO and 9-cis-retinal were obtained from Sigma-Aldrich Corp. (St. Louis, MO, USA). Mouse monoclonal B6-30 and 1D4 anti-rhodopsin antibodies were purified from hybridoma cells. Alexa488 conjugated B6-30 anti-rhodopsin antibody was obtained using the Alexa Fluor 488 Antibody Labeling Kit (Thermo Fisher Scientific). Forskolin was purchased from Tocris Biosciences (Bristol, UK). Scriptaid was purchased from Selleck Chemicals (Houston, TX, USA). YC-001 and its related compounds were synthesized and purified as described below under Medicinal Chemistry.

Small Molecule Libraries

To identify compounds rescuing the transport of P23H opsin, three chemical libraries were tested: the 25K University of Cincinnati Diversity Set, the 50K Life Chemicals Diversity Set, and the 2,400 Spectrum Collection with pharmacological active compounds. A total of 79,080 compounds were tested for their activities with the β-Gal fragment complementation assay.

β-Gal Fragment Complementation Assay for HTS

To identify active compounds that rescue the transport of P23H opsin from the ER to the plasma membrane, we employed a small molecule HTS using the β-Gal fragment complementation assay. Briefly, U2OS(PLC-EA/P23H-PK) cells were suspended in assay medium at 3×10$^5$ cells mL$^{-1}$. The cell suspension was dispensed into 384-well plates (Greiner Bio-one, Monroe, NC, USA) at 20 µL per well, with a Multidrop dispenser (Thermo Scientific, Waltham, MA, USA). Plates with cells then were centrifuged at 200 g for 15 s before incubation at 37° C. with 5% $CO_2$. Plates were removed 24 h later for treatment with tested compounds. A total of 248 plates containing 79,080 compounds from three small molecule libraries were paired with an equal number of assay plates with cultured cells. Due to a limited capacity, these plates were assayed in seven batches. An average of 56.3 nL of 10 mM compound in DMSO was dispensed into each well from column 3 to 22 of paired assay plates using a 50 nL 384-pintool system, such that the final concentration of each compound was 22.52 µM on average. To make the volumes of each well equal to 25 µL per well, columns 1, 3-22 and 24 were dispensed with 5 µL per well of assay medium, whereas columns 2 and 23 of each assay plate were dispensed with 5 µL per well of 0.5% DMSO and 5 µL per well of 25 µM 9-cis-retinal, as 0% and 100% controls, respectively. Each assay plate was shaken for 5 s before further incubation at 37° C. with 5% $CO_2$. After 24 h, assay plates were removed, and each well was incubated with 25 µL of 1× Gal-Screen assay buffer (1:24 substrate-buffer ratio). Assay plates were incubated in the dark for 60-90 min, and luminescence was read from each assay plate with an Envision microplate reader (PerkinElmer) during a 0.1 s per well integration time. The mean and s.d. of readouts in column 2 of each plate were calculated as $Mean_{0\%}$ and $SD_{0\%}$, whereas the average and s.d. of readouts in column 23 were calculated as $Mean_{100\%}$ and $SD_{100\%}$. Equation 1: Activity scores (%)=$(RLU_{cp}-Mean_{0\%})/(Mean_{100\%}-Mean_{0\%})\times 100\%$, where $RLU_{cp}$ is the relative luminescence unit derived for cells treated with a compound. Equation 2: Z'-factor=$1-3\times(SD_{0\%}+SD_{100\%})/(Mean_{100\%}-Mean_{0\%})$; Equation 3: signal-to-background (S/B) ratio=$Mean_{100\%}/Mean_{0\%}$. Activities of all tested compounds were registered with their compound ID by GeneData Screener (Genedata, Basel, Switzerland) and Pipeline Pilot software (Accelrys, San Diego, CA, USA). Hits, cherry-picked from a separate stock dose-dependent activity test, were selected with an activity score cutoff at 20%. Activity of each hit was tested again with the β-Gal fragment complementation assay in a 10-dose series with each dose tested in triplicate. The 10 doses tested were 80, 40, 20, 10, 5, 2.5, 1.25, 0.625, 0.313, and 0.156 µM. Dose-dependent curves of each hit compound were fitted with GeneData and Origin software.

Immunostain and Image-Based Analyses of P23H Mutant Opsin

To characterize the effect of active compounds on the localization of P23H mutant opsin in mammalian cells, an image-based assay was used with cells immunostained for WT or P23H mutant opsin protein. Briefly, NIH3T3-(P23H-opsin/GFP) or NIH3T3-(WT-opsin/GFP) cells were seeded at 5,000 cells per well in a 384-well cell-carrier plate (PerkinElmer) and incubated at 37° C. with 5% $CO_2$ for 2 h. Cells were treated with compounds as described for the β-Gal fragment complementation assay and incubated in assay medium for 24 h. The assay medium then was aspirated, and cells were fixed with 4% paraformaldehyde at 20 µL per well for 20 min at RT. Cells were immunostained in one of two ways: cell membranes were either permeabilized with 0.1% Triton X-100 for 15 min or left intact and then were incubated with 10% goat serum (Life Technologies). To detect opsin on the cell plasma membrane only, intact cells were immunostained with 20 µL per well of 20 µg $mL^{-1}$ B6-30 anti-rhodopsin antibody that recognizes the N-terminal epitope on the extracellular side of rhodopsin. To detect total opsin, cells were permeabilized with Triton X-100 and immunostained with 50 µg $mL^{-1}$ 1D4 anti-rhodopsin antibody specific for the C-terminal epitope on the intracellular side of rhodopsin. Opsin immunostaining was visualized by incubating cells with 5 µg $mL^{-1}$ Cy3-conjugated goat anti-mouse IgG antibody. Three washes with phosphate-buffered saline (PBS: 10 mM $Na_2HPO_4$, 1.8 mM $KH_2PO_4$, pH 7.4, 137 mM NaCl, and 2.7 mM KCl) were performed between each step of incubation with antibody. In the last wash with PBS, DAPI was added to each well at 300 nM. Fluorescence images were obtained with the Operetta High Content Imaging System (PerkinElmer) using a 20× long objective. Five fields were taken of each well for cell images using three channels for fluorescence: GFP (100 ms), Cy3 (300 ms), and DAPI (50 ms). Images were analyzed with Acapella software from the Columbus data storage and analysis system (PerkinElmer). For cells immunostained with opsin on the non-permeabilized cell membrane only, an average of total fluorescence intensity of Cy3 per cell was used to quantify opsin in each well of the 384-well plate. For cells immunostained with opsin in permeabilized whole cells, an average ratio of Cy3 intensity on the cell plasma membrane (PM) to that of the entire cell (opsin ratio PM-to-total) was calculated for each well of a 384-well plate to quantify opsin transport to the plasma membrane. The plasma membrane was defined within ±5% of the cell border. Cell shapes were revealed by GFP fluorescence.

Image-Based Analyses of Clarin1-N48K-Venus

HEK 293 stable cells co-expressing human clarin-1 N48K-Venus fluorescent protein and DsRed-Express-DR fusion protein were obtained from Dr. Yoshikazu Imanishi at Case Western Reserve University (CWRU). Cells were cultured in DMEM medium with 10% FBS following guidelines from ATCC. To test effects of YC-001 treatments on clarin-1 N48K-Venus amounts in these cells, an image-based assay was performed. Briefly, cells were seeded at 20,000 cells per well in 40 µL per well DMEM medium with 10% FBS in a 384-well PerkinElmer View plate coated with poly-D-lysine and cultured at 37° C. with 5% $CO_2$ for 24 h. Cells then were treated with 10 µL per well DMEM medium with 10% FBS containing 5× the final concentration of tested compounds. Such compounds included: MG-132 (Selleckchem, Houston, TX, USA), YC-001 (synthesized), scriptaid (Selleckchem) and tunicamycin (Sellechem). Each compound was tested with 10 doses in a 2-fold dilution series, featuring 3 biological replicates. The 384-well plate was put back for incubation at 37° C. with 5% $CO_2$. After 24 h of exposure to test compounds, the plate was removed, and the medium was aspirated and replaced by 20 µL per well of 4% paraformaldehyde for fixation at RT for 20 min. Cells then were washed once with 50 µL per well of PBS before adding 50 µL per well of PBS containing 10 µM of Hoechst33342 for nuclei staining. After 15 min of dark adaptation at RT, the plate was sealed with a transparent film and removed for imaging by an Operetta High Content Imager (Perkin Elmer). Each well was imaged for 4 fields in each corner of the well with four channels including bright field, YFP, DsRed and Hoechst33342. Images were analyzed by the Columbus storage and analysis system (Perkin Elmer). Hoechst33342 fluorescence images were used to define nuclei and count cells. Bright field images were employed to define cells and select populations of intact cell images. YFP and DsRed fluorescence intensities per cell were measured in each well.

Immunoblots and Quantification

NIH3T3-(P23H-opsin/GFP) or NIH3T3-(WT-opsin/GFP) cells were seeded in a 48-well plate (Corning Costar) at $3.2\times10^5$ cells per well and incubated at 37° C. with 5% $CO_2$ for 2 h. One hundred-µL of assay medium containing a compound at 5× its final concentration was added to each well. The plate was gently shaken for 5 s before further incubation at 37° C. with 5% $CO_2$ for 24 h. The assay medium then was aspirated, and cells were lysed with 100

μL per well PBS containing 0.1% Triton X-100 and complete protease inhibitor cocktail (Roche, Basel, Switzerland) followed by sonication for 3 s. Protein concentrations were determined with the Bradford assay. For PNGase F catalyzed deglycosylation, 3 μL of PNGase F (1,500 U, NEB) was added to the cell lysate and the mixture was incubated at room temperature for 1 h before immunoblotting. For NIH3T3-(P23H-opsin/GFP) cells, 15 μg of total protein were loaded per well onto an SDS-polyacrylamide gel; whereas for NIH3T3-(WT-opsin/GFP) cells, 10 μg of total protein was loaded per well. Opsin protein was immunostained with 0.2 μg mL$^{-1}$ horseradish peroxidase-conjugated 1D4 anti-rhodopsin antibody. Band intensities were measured with ImageJ software (http://imagej.nih.gov/ij/; National the Institutes of Health, Bethesda, MD, USA) and normalized to a glyceraldehyde 3-phosphate dehydrogenase (GAPDH) loading control. Full scans of immunoblotted membranes are shown in FIG. 17.

Preparation of Opsin Membranes

ROS membranes were isolated from bovine retinas under dim red light. To remove membrane associated proteins, ROS membranes were washed with a hypotonic buffer composed of 5 mM bis-tris propane (BTP) and 1 mM EDTA, pH 7.5, followed by gentle homogenization with subsequent centrifugation at 25,000 g for 30 min. This procedure was repeated four times. The final membrane pellet was suspended in 10 mM sodium phosphate buffer, pH 7.0, and 50 mM hydroxylamine to a 3 mg mL$^{-1}$ concentration of rhodopsin, placed on ice and illuminated with a 150 Watt bulb for 30 min. Membranes were pelleted by centrifugation at 16,000 g for 5 min and then washed four times with 10 mM sodium phosphate buffer, pH 7.0, and 2% bovine serum albumin followed by 4 washes with 10 mM sodium phosphate buffer, pH 7.0, and 2 washes with 20 mM BTP, pH 7.5, and 100 mM NaCl. The concentration of opsin was measured with a UV-visible spectrophotometer and quantified using the absorption coefficient $\varepsilon_{280\ nm}=81,200\ M^{-1}\ cm^{-1}$.

Ligand-Opsin Binding Assay

ROS membranes containing opsin were suspended in buffer composed of 20 mM BTP, pH 7.5, and 100 mM NaCl at a final concentration of 2.5 μM. YC-001, scriptaid or 9-cis-retinal were added to these membranes and incubated for a total of 30 min at RT. Treatment conditions included: 5 μM YC-001; 5 μM scriptaid; 5 μM 9-cis-retinal; incubation with x μM YC-001 for 15 min followed by addition of 5 μM 9-cis-retinal for another 15 min (x=2.5, 5, 10, 20, 40, 60, 80 μM); incubation with 5 μM YC-001 and 5 μM 9-cis-retinal together. In a separate experiment, opsin membranes were incubated with a mixture of YC-001 or scriptaid together with 9-cis-retinal. Membranes then were solubilized with 20 mM DDM for 10 min at RT and UV-visible spectra of these samples were measured. To follow the kinetics of isorhodopsin regeneration, opsin membranes were treated with 0, 20 or 60 μM YC-001 for 15 min at RT. The treated opsin membranes were solubilized with 20 mM DDM for 10 min and then treated with 5 μM 9-cis-retinal. UV-visible spectra of the samples were measured every 2 min until 2 h of reaction time at RT. Each condition was repeated three times. The time course of isorhodopsin regeneration was fitted by a second order exponential decay and apparent half-lives were obtained at the time when reaction reached half of the end-point product.

Alternatively, opsin incubated with the above ligands was purified by 1D4-immunoaffinity chromatography. Solubilized membrane lysates were cleared by centrifugation at 16,000 g for 15 min, and the supernatants were incubated with 1D4-immunoaffinity resin (6 mg of 1D4 anti-rhodopsin antibody per mL resin) equilibrated with 20 mM BTP, pH 7.5, 100 mM NaCl, 2 mM DDM for 1 h at RT. After washing, opsin samples were eluted by addition of 1D4 peptide (TETSQVAPA) (SEQ ID NO: 1) to the above buffer and their spectra were measured with a UV-visible spectrophotometer.

To test if YC-001 could replace the 11-cis-retinal chromophore in rhodopsin, freshly isolated ROS membranes (2.5 μM) were treated with 20 μM YC-001 for 60 min, and absorption spectra were taken before and after treatment. An absorption spectrum of 100 μM YC-001 in 20 mM BTP, pH 7.5, and 100 mM NaCl was used as the control.

To test if YC-001 stabilizes rod opsin, opsin samples (2.5 μM) were incubated with or without 10 μM YC-001 for 15 min, followed by solubilization in 20 mM DDM. Solubilized opsin samples were incubated at RT for 0, 1, 3, and 6 h before incubation with 10 μM 9-cis-retinal in the dark for isorhodopsin regeneration. UV-visible spectra of these samples then were measured.

Fluorescence Spectroscopy

To confirm the binding of YC-001 in the retinoid-binding pocket of rod opsin, quenching of Trp residues was monitored before and after adding increasing concentrations of YC-001, scriptaid or 9-cis-retinal ligands to ROS membranes containing opsin. Emission spectra were recorded with a Perkin Elmer L55 Luminescence Spectrophotometer at 20° C. between 300 and 450 nm after excitation at 295 nm, with excitation and emission slit bands set at 5 and 10 nm, respectively. Changes in Trp fluorescence ($\Delta F/F0$; where $\Delta F$ is the difference between the initial Trp fluorescence recorded at 330 nm (F0) and Trp fluorescence recorded at 330 nm at a specified YC-001 concentration) were plotted as a function of the ligand concentration. Binding curves were fitted by the Hill function using Origin software for each compound and the $EC_{50}$ was calculated. All experimental data were corrected for background and self-absorption of excitation and emission light (inner filter effect).

Bovine Opsin Crystallization for Raman Spectroscopy

Bleached ROS membranes bearing opsin were solubilized with either 20 mM BTP, pH 7.5, or 50 mM MES, pH 6.4, together with 130 mM NaCl, 1 mM MgCl$_2$, 10% sucrose, and 1% n-octyl-β-D-glucopyranoside (OG) for 1 h at 4° C. Insoluble debris was removed by centrifugation at 16,000 g for 5 min at 4° C. Crystallization screens were performed by the sparse matrix crystallization method based upon previously published crystallization conditions for rhodopsin and opsin. Each hanging drop was prepared by mixing equal volumes of solubilized opsin and a reservoir solution containing 3.0-3.6 M ammonium sulfate in 0.05-0.1 M sodium acetate buffer, pH 5.2-5.6. Crystals appeared within 2-5 days at 4° C. and were analyzed directly by Raman spectroscopy.

Raman Spectroscopy

Here, we used Raman microscopy to test if YC-001 binds rod opsin in a single crystal. A rod opsin crystal was transferred into 4.5 μL of fresh reservoir solution on a siliconized glass coverslip and transferred into a hanging drop crystallization tray where the well contained 1 mL of the same solution. An 80 mW, 647.1 nm Kr$^+$ laser beam (Innova 70 C, Coherent, Palo Alto, CA, USA) was focused on the rod opsin crystal with a 20× objective. The Raman spectrum of the rod opsin crystal was accumulated over 100×1 s. The laser beam was then focused on the drop around the crystal, and a Raman spectrum for the holding solution was acquired and subtracted from the spectrum of the opsin crystal. To test if YC-001 binds to the rod opsin, 0.5 μl of 100 mM YC-001 in DMSO was added to a 4.5 μl drop surrounding a rod opsin crystal. The opsin crystal was soaked with YC-001 for about 20 min to reach equilibrium, and then a Raman spectrum of the same opsin crystal was acquired for 100×1 s. In parallel, a Raman spectrum of the surrounding solution containing YC-001 was collected and subtracted from the spectrum of the YC-001 soaked crystal. To obtain the Raman difference spectrum, a secondary subtraction was performed as Equation 4: Raman difference spectrum=[Spectrum$_{(YC\text{-}001\ soaked\ opsin\ crystal)}$−Spectrum$_{(surrounding\ solution\ with\ YC\text{-}001)}$]−[Spectrum$_{(rod\ opsin\ crystal)}$−Spectrum$_{(surrounding\ solution)}$]. To obtain the YC-001 standard spectrum, a Raman spectrum of the surrounding solution was subtracted from the spectrum of 10 mM YC-001 in the surrounding solution. Because YC-001 was added to the crystal using DMSO as dissolving solution that is absent in the opsin crystal, the difference spectrum showed a peak at 1420 cm$^{-1}$ derived from DMSO.

cAMP Quantification Assay

NIH3T3-(Opsin/GFP) and NIH3T3-(GFP) were plated in two 96-well plates at a density of 50,000 cells per well in 100 μl of DMEM medium containing 10% FBS and antibiotics. After 24 h, cells were washed with Krebs Ringer bicarbonate buffer containing glucose (KRBG), and incubated with KRBG buffer containing 100 μM cAMP specific phosphodiesterase inhibitor, Ro 21-1724 (Tocris, UK) at RT for 10 min. Under dim red light, cells then were treated with 25 μL of 6× its final concentration of forskolin (final 20 μM) followed by addition of 25 μL 6× final concentration of 9-cis-retinal, YC-001 or 9-cis-retinal and YC-001 together. While one plate then was wrapped with aluminum foil, the second plate was exposed to regular room light. Both plates were kept in a cell culture incubator for 15 min at 37° C. in 5% $CO_2$. Levels of accumulated cAMP were detected with the Catchpoint cAMP fluorescent assay kit (Molecular Devices, Sunnyvale, CA USA) and the fluorescence with excitation/emission at 530/590 nm was read with a Flexstation3 plate reader (Molecular Devices) as described in the manufacturer's protocol.

$G_t$ Activation Assay $G_t$ was extracted and purified from frozen bovine ROS membranes as described in Preparation of Opsin Membranes. The intrinsic increase in the fluorescence from Gtα was measured with a L55 luminescence spectrophotometer (PerkinElmer Life Sciences) using an excitation and emission wavelengths of 300 and 345 nm, respectively. To test the effect of YC-001 on the basal activity of rod opsin, opsin membranes were incubated for 15 min at 20° C. with a 40 μM concentration of either YC-001, the non-active analogue-YC-014, 9-cis-retinal or a co-treatment with 9-cis-retinal and YC-001. DMSO-treated opsin membranes were used to obtain a baseline for the basal activity of opsin. The molar ratio of opsin to $G_t$ was 1:10, with opsin at a concentration of 100 nM and $G_t$ at 1000 nM. Opsin membranes treated with either 9-cis-retinal alone or a co-treatment of 9-cis-retinal and YC-001 were bleached for 1 min with a fiber light source (Dolan Jenner Industries Inc., Boxborough, MA) equipped with a 480 to 520 nm band-pass wavelength filter (Chroma Technology Corporation, Bellows Falls, VT, USA). This step was followed by the addition of 300 μM GTPγS (Sigma-Aldrich) to determine the GTPγS-induced complex dissociation and corresponding fluorescence changes. $G_t$ activation rates were determined and plotted for the first 100 s of the $G_t$ activation assay.

Animal Care and Treatment Conditions

Abca4$^{-/-}$Rdh8$^{-/-}$[42] mice with a 129Sv/Ev or C57BL/6 mixed background were used for light-induced retinal degeneration assays. Abca4$^{-/-}$Rdh8$^{-/-}$ mice were genotyped to confirm that they did not carry the Rd8 mutation but did carry the Leu variation at amino acid 450 of RPE65. Male and female C57BL/6 mice (Jackson Laboratory, Bar Harbor, ME) at six weeks of age were used to test the effects of YC-001 treatment on the retinoid cycle and bw as well as to determine parenterally administrated YC-001 enter the eyes. YC-001 was dissolved in DMSO at 80-160 mg mL$^{-1}$, and the solution was provided to mice by i.p. injection. All mice were housed and maintained in a 12 h light (≤10 lux)/12 h dark cycle in the Animal Resource Center at the School of Medicine, CWRU. Animal procedures and experimental protocols were approved by the Institutional Animal Care and Use Committee at CWRU and conformed to recommendations of both the American Veterinary Medical Association Panel on Euthanasia and the Association for Research in Vision and Ophthalmology.

Bright Light-Induced Retinal Degeneration

Retinal degeneration was initiated by exposing Abca4$^{-/-}$Rdh8$^{-/-}$ mice for 30 min to white light with an intensity of 10,000 lux (150-W spiral lamp, Hampton Bay, Home Depot, Atlanta, GA USA). Pupils of mice were dilated with 1% tropicamide 3 min before bright light exposure. YC-001 or DMSO were also administered i.p. 30 min before such exposure. The effects of YC-001 were tested at two dosages: 50 and 200 mg kg$^{-1}$ bw. The volume of each injection was less than 50 μL. Retinal structures were analyzed by SD-OCT seven days after bright light exposure. Mice were then euthanized, and their eyes were subjected to HE staining and imaging.

SD-OCT Imaging

To assess the effect of YC-001 treatment on Abca4$^{-/-}$Rdh8$^{-/-}$ mice following bright light-induced retinal degeneration, we performed ultrahigh-resolution SD-OCT (Bioptigen, Morrisville, NC) for in vivo imaging of mouse retinas. Briefly, pupils of mice were dilated with 1% tropicamide. Three min later, mice were anesthetized by i.p. injection of a cocktail containing ketamine (20 mg mL$^{-1}$) and xylazine (1.75 mg mL$^{-1}$) at a dose of 4 μL g$^{-1}$ bw. The A scan/B scan ratio was set at 1200 lines. Four frames of OCT images scanned at 0° were acquired in the B-mode, averaged, and saved as PDF files. To measure changes to photoreceptors in the retinas challenged with bright light and assess the effect of YC-001 on retinal protection, the thickness of the ONL was measured along the scanned SD-OCT image at 8 points from the nasal to temporal end of the retina. Each treatment group contained three mice, and a graph of ONL thicknesses was plotted to obtain the means and s.d.s of the triplicate samples.

Retinal Histology after HE Staining

To examine the overall structure of the retinas subjected to bright light and treatment with YC-001, mice were euthanized, and their eyes were removed and fixed in 4% paraformaldehyde and 0.5% glutaraldehyde before paraffin sectioning. Paraffin sections (5 μm thick) were stained with HE and imaged by light microscopy (Leica, Wetzlar, Germany).

Quantification of YC-001 in Mouse Eye by HPLC

To measure the amount of YC-001 in the eye following systemic delivery, YC-001 was administered to C57BL6 mice by i.p. injection at a dose of 200 mg kg$^{-1}$ bw. Mice then were euthanized at 30 min, 3 h and 24 h after these injections, and their eyes were removed for analysis. Eyes from two mice under the same treatment were homogenized on ice in 1 mL of PBS:methanol (1:1 ratio). Four-mL of hexanes were then added to the homogenized sample, and the mixture was vortexed for 15 s. The mixture was centrifuged at 3,220 g for 15 min at 4° C. to separate the hexanes from the aqueous layer. From the top hexane layer, 3.5 mL was transferred to a glass vial. This sample was then dried in a Savant speed vacuum concentrator (Thermofisher, Waltham, Massachusetts, USA) and dissolved in 300 µL methanol. One hundred-µL of dissolved sample were injected into an HPLC system connected to an Agilent Sil column (5 µm, 4.6×250 mm; Agilent Technologies, Santa Clara, CA) for separation with 10% ethyl acetate in hexanes at a flow rate 1.4 mL min$^{-1}$. A chromatogram of absorption at 340 nm was then obtained. A YC-001 standard was subjected to the same procedures as the ocular samples and used to establish a retention time at 13.2 min. By comparing ocular samples to its standard curve of YC-001, the amount of YC-001 was then quantified in pmol eye$^{-1}$ at different time points after its systemic administration. The identity of YC-001 in the peak fraction with a retention time of 13.2 min was confirmed by LC-MS using the same chromatography method as applied for HPLC.

Synthesis of YC-001

YC-001 was initially obtained from the University of Cincinnati for activity confirmation in mammalian cells. Its chemical structure was confirmed by nuclear magnetic resonance (NMR) spectroscopy and LC-MS. To supply enough compound for in vivo studies, YC-001 was synthesized as described in FIG. 9. Condensation of 2-bromo-1-(5-chlorothiophen-2-yl)ethan (1) and 2-(thiophen-2-yl)acetic acid (2) in the presence of trimethylamine, followed by treatment with 1,8-diazabicycolo[5.4.0]undec-7-ene (DBU) yielded the target compound, YC-001.

COX-1 Activity Assay

The effect of the compound YC-001 on cyclooxygenase 1 (COX-1) activity was evaluated using the COX1 Inhibitor Screening Kit (Abcam, Cambridge, MA, USA) according to the manufacture's protocol. Briefly, the assay is based on the fluorometric detection of Prostaglandin G2, the intermediate product generated by the COX-1 enzyme. COX reaction mix included ovine COX-1, COX probe and COX cofactor and was prepared in a 96-well plate. YC-001 working solutions were dissolved in DMSO, and then mixed with COX Reaction Mix to the final concentrations (80, 40, 20, 10, 5, 2.5, 1.25, 0.625, 0.312, 0.156, 0.078 and 0.039 µM). Equivalent volume of DMSO was used as vehicle control and SC560 was used as a positive control. All controls and samples were measured in triplicate. Then Arachidonic Acid was added into each well to initiate all the reactions at the same time. The fluorescence was measured at Ex/Em=535/587 nm in a kinetic mode for 15 min at 25° C. Five time points were chosen in the linear range of the plot and the corresponding values for the fluorescence were used to calculate the slope of the linear regression equation. Relative COX-1 activity was calculated as Equation 5:

$$\text{Relative } COX-1 \text{ Activity } (\%) = \frac{\text{Slope of sample}}{\text{Slope of Enzyme Control}} \times 100.$$

Metabolic Stability of YC-001

A standard metabolic stability assay was performed in the presence of mouse or human liver microsomes. YC-001 (5 µM) was incubated with the microsomes (0.125 mg mL$^{-1}$) resuspended in 0.2 mL of PBS buffer, pH 7.4 composed of 10 mM Na2HPO4, 1.8 mM KH2PO4, 137 mM NaCl, and 2.7 mM KCl. The enzymatic reaction to produce oxidized metabolites was initiated by addition of NADPH (1 mM). Samples were incubated at 37° C. for up to 240 min. Incubation without the cofactor was conducted in parallel to assess NADPH-independent clearance. The reactions were stopped with 0.2 mL of methanol followed by 0.3 mL chloroform. Residual YC-001 was extracted by vigorous shaking. To facilitate phase separation, the samples were spun down for 2 min, 15,000×g. The chloroform fraction was collected, dried down, and the extracted organic compounds were redissolved in 0.2 mL of methanol. To quantify YC-001, the samples were injected onto an Eclipse XDB-C18 column (4.6×150 mm, 5 µm) (Agilent Technologies) equilibrated with solvent composed of 30% acetonitrile in water (v/v), and 0.1% formic acid. YC-001 was eluted in a gradient of acetonitrile in water (30-100%) developed within 15 min at a flow rate of 1 mL min$^{-1}$, detected at 350 nm, and quantified by correlating peak areas with known quantities of an original synthetic standard.

To assist in the interpretation of the YC-001 metabolic clearance data, two benchmark compounds verapamil (2-(3, 4-dimethoxyphenyl)-5-[2-(3,4-dimethoxyphenyl)ethylmethylamino]-2-propan-2-ylpentanenitrile) (Sigma-Aldrich) and quinidine ((S)-[(2R,4S,5R)-5-ethenyl-1-azabicyclo[2.2.2]octan-2-yl]-(6-methoxyquinolin-4-yl) methanol) (Sigma-Aldrich) were in the same experimental conditions as YC-001. The enzymatic reactions were stopped by addition of 0.3 mL ice-cold acetonitrile. To enable mass spectrometry-based detection and quantification of these drugs, 1 nmol of internal standard d3-verapamil (Cayman Chemical Company, Ann Arbor, MI, USA) for verapamil or imipramine (3-(5,6-dihydrobenzo[b][1]benzazepin-11-yl)-N,N-dimethylpropan-1-amine) (Alfa Aesar, Haverhill, MA, USA) for quinidine were added to the samples before they were spun down (15 min at 15,000×g) and injected onto a C18 X-Bridge column (100×2.1 mm; 3.5 µm) (Waters, Milford, MA, USA). HPLC separation of verapamil, quinidine, and the internal standards was achieved by a linear gradient of acetonitrile from 30 to 100% in water (v/v) developed within 15 min at a flow rate of 0.5 mL min$^{-1}$. All solvents contained 0.1% formic acid (v/v). The HPLC eluate was sprayed into a L×Q linear-trap mass spectrometer (Thermo Fisher Scientific) via an electrospray probe operating in the positive ionization mode. Parameters of ionization and detection were tuned with synthetic standards for these drugs to achieve the highest possible sensitivity. Verapamil and its deuterated form were detected by selected reaction monitoring (SRM) using m/z 455.3→303.2 and 458.3→306.3 transitions, whereas quinidine and its corresponding internal standard (imipramine) were detected by fragmentation at m/z 326.3→307.2 and 281.2→86.1, respectively. For quantification, calibration curves were generated based on the linear relationship between ratios of the SRM ion intensities corresponding to the drug and the internal standard versus the molar ratios of these compounds.

Pharmacokinetics of YC-001 in Mice

C57BL/6J mice ranging from 8 to 12 weeks of age were purchased from Jackson Labs. For administration, YC-001 was dissolved in DMSO at 160 mg mL$^{-1}$. To obtain the blood clearance curve for YC-001, each animal was treated by intraperitoneal injection of YC-001 at 200 mg kg$^{-1}$ bw. After administration, blood was collected at 5, 10, 15, 20, 30, 45, 60 and 90 min from the orbital sinus and dropped into K$_2$EDTA blood collection tubes (FisherScientific). Mice were anesthetized with a ketamine/xylazine cocktail two min before blood collection. The blood samples were then incubated at 4° C. for 2 h before centrifugation at 1,800×g for 20 min to collect the supernatant that was the plasma. Plasma was mixed with twice the volume of methanol and then stored at −80° C. YC-001 was extracted from the samples (300 to 600 μL) with 0.6 mL chloroform. The chloroform fraction was collected, dried, and the extracted organic compounds were dissolved in 0.25 mL of methanol. One hundred-μL of each sample was injected onto an Eclipse XDB-C18 column (4.6×150 mm, 5 μm) and YC-001 was detected and quantified as described in the section Metabolic stability of YC-001.

Micro Ames Test for YC-001

To determine the potential genotoxicity of YC-001, a Micro Ames test was performed by the Charles River Laboratories, Inc. The S9 microsomal fraction was obtained from Moltox Molecular Toxicology, Inc. (Boone, NC, USA). A premixture was prepared including 25 μL of S9 mix (10% v/v S9 fraction in 8 mM $MgCl_2$, 33 mM KCl, 100 mM sodium phosphate buffer, pH 7.4, +S9) or phosphate buffer (0.2 M sodium phosphate, pH 7.4, 0S9), 5 μL of bacterial culture (>1000×$10^6$ bacteria $mL^{-1}$) and 100 μL of molten top agar supplemented with 0.05 mM biotin and minimal histidine (0.05 mM) and minimal tryptophan (0.05 mM). The 24-well plates were prepared by adding 1.3 mL of minimal bottom agar (1.3% agar, Vogel-Bonner medium E and 0.25% glucose) to each well. A 10 μL aliquot of YC-001 working solution/negative/positive control was added to each well followed by addition of 130 μL of the premixture. The plates kept on a leveled surface for 1 h while the top agar solidified, then were incubated at 37° C. for 72 h. After this period, plates were stored at 4° C. before revertant colony counts were manually recorded using an inverted microscope. A total of five bacterial strains were tested including *S. typhimurium* TA1535 hisG46 rfa ΔuvrB (T1535), *S. typhimurium* TA97a hisO1242 rfa ΔuvrB pKM101(TA97a), *S. typhimurium* TA98 hisD3052 rfa ΔuvrB pKM101 (TA98), *S. typhimurium* TA100 hisG46 rfa ΔuvrB pKM101 (TA100), and *E. coli* WP2 trp uvrA pKM101 (WP2). For each bacterial strain YC-001 was tested at a total of eight dosages in duplicate: 250, 75, 25, 7.5, 2.5, 0.75, 0.25, and 0.075 μg per well, with or without S9 metabolism. Without S9, positive controls for each bacterial strain were as follows: 0.05 μg per well sodium azide (NaAz) for TA1535 and TA100, 2.0 μg per well 9-aminoacridine hemihydrate (9-AC) for TA97a, 0.2 μg per well 2-nitrofluorene (2NF) for TA98, 0.1 μg per well 4-nitroquinoline N-oxide (NQO) for WP2. With S9, the positive controls for the five strains were: 0.1 μg per well 2-aminoanthracene (2AA) for TA1535, TA97a, TA98 and TA100, and 2 μg per well 2AA for WP2. Positive results (indicative of mutagenic potential) required both the following criteria: 1) The tested compound show more than 2 times the revertant colony counts than negative controls for TA100, TA97a and WP2 or more than 3 times for TA98 and TA1535; 2) the increased revertant colony counts reveal a concentration dependence. Negative results (not indicative of mutagenic potential) required the revertant colony counts of tested compounds to be less than 2 times of negative controls for TA100, TA97a, and WP2 or less than 3 times for T98 and TA1535.

Cell Surface Immunostain for Rhodopsin Mutants

Human rhodopsin cDNA was placed into the pcDNA3.1 (+) vector (pcDNA3.1-hOpsin). Site directed mutagenesis was performed following the QuickChange II site-directed mutagenesis kit (Agilent Technologies Inc.). Primers for the following mutations were as follows:

```
T4R-forward,
                                    (SEQ ID NO: 2)
5'-atgaatggcagagaaggccctaacttctacg-3';
```

```
T4R-reverse,
                                    (SEQ ID NO: 3)
5'-cgtagaagttagggccttctctgccattcat-3';

P53R-forward,
                                    (SEQ ID NO: 4)
5'-gctgggcttccgcatcaacttcctcacgc-3';

P53R-reverse,
                                    (SEQ ID NO: 5)
5'-gcgtgaggaagttgatgcggaagcccagc;

G106R-forward,
                                    (SEQ ID NO: 6)
5'-ggatacttcgtcttcaggcccacaggatgca-3';

G106R-reverse,
                                    (SEQ ID NO: 7)
5'-tgcatcctgtgggcctgaagacgaagtatcc-3';

C110Y-forward,
                                    (SEQ ID NO: 8)
5'-cgggcccacaggatacaatttggagggcttc-3';

C110Y-reverse,
                                    (SEQ ID NO: 9)
5'-gaagccctccaaattgtatcctgtgggcccg-3';

D190N-forward,
                                    (SEQ ID NO: 10)
5'-gctcgtgtggaatcaactactacacgctcaag-3';

D190N-reverse,
                                    (SEQ ID NO: 11)
5'-cttgagcgtgtagtagttgattccacacgagc-3';

P267L-forward,
                                    (SEQ ID NO: 12)
5'-gatctgctgggtgctctacgccagcgtggc-3';

P267L-reverse,
                                    (SEQ ID NO: 13)
5'-gccacgctggcgtagagcacccagcagatc-3'.
```

DNA vectors with rhodopsin mutations were confirmed by Sanger sequencing. After NIH3T3 cells were transfected with pcDNA3.1-hOpsin or its mutants for 24 h, these cells were resuspended and seeded into a 96-well plate with an optic bottom (Corning). Seeded cells were treated with YC-001 (40, 10 or 2.5 μM), 9-cis-retinal (5 μM) or DMSO (0.1% v/v). Each condition was repeated in three wells. The treated plate was covered in tin foil and incubated at 37° C. with 5% $CO_2$ for 24 h. Cells were then immunostained with Alexa 50 μg $mL^{-1}$ 488-conjugated B6-30 anti-rhodopsin antibody. Cells were not exposed to detergents so that cell membranes were kept intact and only rhodopsin on the cell surface was immunostained. Alexa 488 fluorescence was imaged by the ImageExpress (Molecular Devices) high-content imager with a 20× objective.

Medicinal Chemistry of YC-001

Analogues of YC-001 (YC-022 to YC-069) were synthesized by Charles River, Inc. (Wilmington, MA, USA). Detailed synthetic steps are described in FIG. 18. LC-MS and NMR data of purified YC-001, and YC-022 to YC-069. YC-002-YC-021 were purchased from commercial vendors including Enamine LLC (Monmouth Jct., NJ, USA), Matrix Scientific (Columbia, SC, USA) and Tokyo Chemical Industry Co., Ltd. (Portland, OR, USA). Chemical purities of the YC compounds were higher than 94%, as determined by NMR and LC-MS. Activities of YC compounds were tested with the β-Gal fragment complementation assay, as described in a prior section. All YC compounds were tested at 10 doses, each in triplicate: 80, 40, 20, 10, 5, 2.5, 1.25, 0.625, 0.313, and 0.156 μM. Activity scores were standardized to the effect of 5 µM 9-cis-retinal under dark conditions. YC derivatives with efficacies higher than 20% to that of 9-cis-retinal were considered active compounds.

Retinoid Cycle Analyses

To test if treatment with YC-001 affects visual pigment regeneration, we quantified the 11-cis-retinyl oxime extracted from retinas of C57BL/6 mice after different periods of dark adaptation following exposure to bright light. Mice at 6 weeks of age were administered YC-001 at 200 mg kg$^{-1}$ bw via i.p. injection. At 30 min following YC-001 administration, eyes were dilated with 1% tropicamide. Mice then were anesthetized with a cocktail containing 20 mg mL$^{-1}$ of ketamine and 1.75 mg mL$^{-1}$ of xylazine at a dose of 4 µL g$^{-1}$ bw. Anesthetized mice were exposed to bright light with an intensity of 10,000 lux for 10 min to bleach about 90% of the rhodopsin pigment. Mice then were returned to the dark for recovery. Animals then were euthanized at 0, 2, 4, 6 or 24 h after bleaching and recovery in the dark, and their eyes were removed and homogenized in 1 mL of 1:1 PBS:ethanol mixture (v/v) containing 40 mM hydroxylamine. For each time point, three mice were used as replicates. Homogenized eye samples were incubated at RT for 20 min. In the dark, 4 mL of hexanes were added to each sample and the mixture was vigorously shaken for 2 min before centrifugation at 3,200 g for 10 min, and transfer of the top hexanes phase to a glass tube. Hexanes were then evaporated in a speedvac concentrator for 30 min. Dried samples containing retinoids were suspended in 300 µL hexanes and transferred to a glass vial for HPLC analysis. 11-cis-Retinyl oxime released from the regenerated rhodopsin pigments were separated on an Agilent Sil column (5 µm, 4.6×250 mm) with an isocratic flow of 10% ethyl acetate in hexanes (1.5 mL min$^{-1}$) and detected at 325 nm. Amounts of 11-cis-retinyl oximes per eye were quantified by normalizing the peak area to an 11-cis-retinyl oxime standard. 11-cis-Retinyl oximes were quantified in three eye samples per condition, and the means and s.d.s were calculated.

ERG Analyses

C57BL/6 mice at 2 months of age were placed in the dark overnight. Mice then were divided into a YC-001-treated group, a DMSO-treated group, and an unbleached group. Each group contained 3 mice (2 females and 1 male). Mice were given a single dose of YC-001 at 200 mg kg$^{-1}$ by i.p. injection. The DMSO group was treated with an equivalent volume of DMSO compared to the YC-001-treated group. One h after YC-001 or DMSO administration, mouse eyes were treated with 1% tropicamide eye drops for pupil dilation, exposed to 2,000 lux of illumination for 5 min and returned to the dark. Mice were anesthetized after a bleach for scotopic ERG recordings. Briefly, every 5 min a single-flash scotopic ERG at 1.6 cd·s·m$^{-2}$ was recorded until 1 h after a bleach. A-wave amplitudes of each ERG recording were measured, averaged from three animals, and plotted as a function of time and fitted to a linear function using Origin software version 8.1.

Bw Measurements

To estimate the long-term toxicity of YC-001 in mice, we administered YC-001 to C57BL/6 mice by daily i.p. injections from Day 14 to 38 after birth with one of two doses, either 100 mg kg$^{-1}$ or 200 mg kg$^{-1}$ bw. Equivalent volumes of DMSO were injected into control groups. Bws of treated mice were measured daily. Each dosage group contained 3 mice including males and females. No deaths were observed either during the treatment phase or for 25 days following treatment.

Statistics

Data collected for the β-Gal fragment complementation assay, image-based analyses, and the cAMP quantification assay included three biological replicates. Positive and negative controls were repeated 8 or 6 times, whereas compounds were tested in triplicate at six to ten concentrations. Effects of the tested compounds were analyzed in a dose-dependent manner to exclude random errors. For the opsin binding assay, isorhodopsin regeneration assay, compound stability assay and G$_t$ activation assay, each experiment was repeated 3 individual times and parameters were averaged from those repeats with error bars as s.d.s. The effect of each compound was either plotted in a dose-dependent or time-dependent manner as compared with controls. All samples were included in the analyses.

For animal studies, two doses of YC-001 were used, with each dose tested in three animals including males and females. Age-matched animals were selected from the same one or two litters and were grouped randomly into different treatment conditions after ensuring that every group had at least one male and one female animal. Personnel who performed the retinal function, retinal imaging, or retinoid analyses were blinded as to the treatment status of these mice. All samples were included for animal studies. Sample size for the animal studies was validated by Gpower3 software using the post-hoc power analysis for a two-tailed t-test[70]. Effect size index was calculated in Equation 6:

$$d = \frac{|\mu 1 - \mu 2|}{\sqrt{0.5x(\sigma 1^2 + \sigma 2^2)}},$$

>5, that made the power (1−β error probability)>0.99 for sample size of 3. Average ONL thicknesses were µ1 and µ2 from SD-OCT of retinas treated with 200 mg kg$^{-1}$ either YC-001 or DMSO, and σ1 and σ2 were s.d.s of those from YC-001- and DMSO-treated retinas, respectively.

Results

Identification of YC-001 by HTS

Using a cell-based β-Gal fragment complementation assay, a HTS was carried out to identify small molecules that promote the transport of the unstable P23H mutant opsin protein from the ER to the plasma membrane (FIG. 1). A total of 79,080 compounds were tested at an average dose of 22.5 µM with the quality control parameter Z'-factor ranged from 0.55-0.84. Among 29 other hits selected with efficacies greater than 50% and potencies less than 20 µM, the activity of YC-001 showed a potency of 7.8 µM and an efficacy at 150-310% of the control activity score (FIG. 1E) that achieved a maximum within 15 h (FIG. 1F). Variability of YC-001's efficacy of 150 to 310% was seen between experiments. No additive effect was seen with YC-001 and 9-cis-retinal co-treatment (FIG. 1G), suggesting a similar mechanism of action for these two compounds. Importantly, YC-001 activity was not affected when cells were exposed to light, whereas the activity of the 9-cis-retinal positive control required that cells be incubated in the dark.

Confirmation of YC-001's Activity

To confirm the activity of hit compounds identified by the HTS, high-content imaging analysis was used in NIH3T3 cells stably co-expressing mouse P23H opsin and green fluorescent protein (GFP) immunostaining the rod opsin mutant on the plasma membrane only, or in the whole cell. Images taken by both immunostaining methods showed that the P23H opsin on the plasma membrane was increased by treatment with either YC-001 or 9-cis-retinal in a dose-dependent manner (FIG. 2). Meanwhile, the ratio of P23H opsin stain in the ER region to total P23H opsin staining decreased by treatment with YC-001, suggesting that P23H opsin was mobilized from the ER to the plasma membrane, instead of just a change of its total amount (FIG. 2M,N). At a concentration higher than 10 µM, 9-cis-retinal killed most cells, whereas YC-001 up to 40 µM did not affect cell number. A total of 10 hit compounds were confirmed with activity rescuing the transport of P23H opsin (Table 1) and none of these hit compounds resembled the chemical structure of 11-cis-retinal, the natural ligand and pharmacological chaperone of rod opsin. YC-001 (FIG. 1C), known as CID 2377702 in the PubChem database, was screened previously in 16 other bioassays but demonstrated no known activities (https://pubchem.ncbi.nlm.nih.gov). Due to its novel pharmacological activity discovered in this study, YC-001 was selected for further investigation. Scriptaid, a pan-histone deacetylase inhibitor, also showed strong activity in rescuing P23H opsin transport (Table 1). Moreover, co-treatment with YC-001 and scriptaid produced a synergistic effect, suggesting distinctive targets for these two active compounds. YC-001 did not affect the amount or stability of the clarin-1 N48K mutant that causes Type III Usher syndrome in HEK 293 cells, suggesting the activity of YC-001 is specific to rod opsin (Table 1).

TABLE 1

Compounds with top activities for rescuing P23H opsin transport compared to 9-cis-retinal.

| Compound name | Structure | β-Gal fragment complementation assay Activity score (%) | | | Immunostaining HCS$^a$ MEM-Total ratio$^b$ | | Improved glycosylation$^c$ |
|---|---|---|---|---|---|---|---|
| | | EC$_{50}$ (µM) | Max (fit) | Max (Exp) | EC$_{50}$ (µM) | Max (fit) | |
| Scriptaid | 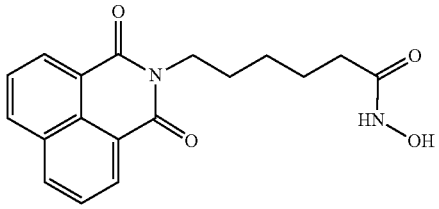 [SMILES: O=C(CCCCCN1C(=O)c2cccc3cccc(c23)C1=O)NO] | 3.09 | 98.2 | 98 | 0.38 | 0.070 | n |
| F5581-0240 | 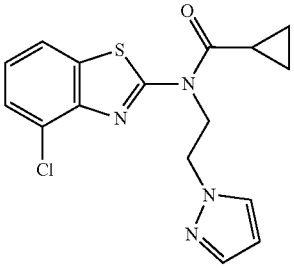 [SMILES: O=C(C1CC1)N(CCn1cccn1)c1nc2c(Cl)cccc2s1] | 5.93 | 230 | 244 | 0.64 | 0.010 | y |
| F6257-1860 | 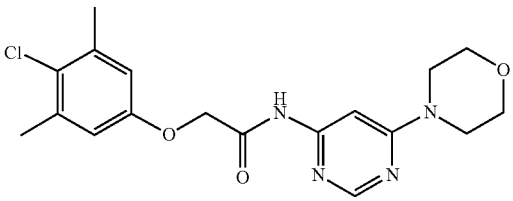 [SMILES: Cc1cc(OCC(=O)Nc2cc(N3CCOCC3)ncn2)cc(C)c1Cl] | 10.7 | 234 | 211 | 1.07 | 0.022 | n |
| F5937-0207 | 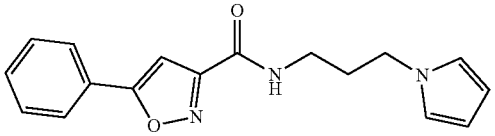 [SMILES: O=C(NCCCn1cccc1)c1cc(-c2ccccc2)on1] | 8.38 | 37.3 | 32.8 | 1.33 | 0.021 | n |

TABLE 1-continued

Compounds with top activities for rescuing P23H opsin transport compared to 9-cis-retinal.

| Compound name | Structure | β-Gal fragment complementation assay Activity score (%) | | | Immunostaining HCS[a] MEM-Total ratio[b] | | Improved glycosylation[c] |
|---|---|---|---|---|---|---|---|
| | | EC$_{50}$ (μM) | Max (fit) | Max (Exp) | EC$_{50}$ (μM) | Max (fit) | |
| F3382-5924 | | 28.6 | 155 | 931 | 2.42 | 0.046 | y |
| YC-001 | | 8.7 | 310 | 310 | 2.75 | 0.030 | y |
| F2902-1134 | | 21.6 | 31.5 | 23.1 | 4.15 | 0.031 | n |
| F6244-1415 | | 8.61 | 25.2 | 24.8 | 4.2 | 0.063 | n |
| F5875-0200 | | 25.0 | 51.6 | 31.8 | 6.2 | 0.041 | n |

TABLE 1-continued

Compounds with top activities for rescuing P23H opsin transport compared to 9-cis-retinal.

| Compound name | Structure | β-Gal fragment complementation assay Activity score (%) | | | Immunostaining HCS[a] MEM-Total ratio[b] | | Improved glycosylation[c] |
|---|---|---|---|---|---|---|---|
| | | $EC_{50}$ (μM) | Max (fit) | Max (Exp) | $EC_{50}$ (μM) | Max (fit) | |
| F5111-0031 | *(structure)* | 54.3 | 165 | 60.4 | 6.76 | 0.025 | y |
| 9-cis-retinal | *(structure)* | 2.7 | 159 | 123 | 0.377 | 0.019 | y |

Note:
[a]HCS, high-content screening;
[b]MEM-total, the ratio of the fluorescence intensity of P23H rod opsin on the plasma membrane to that in the whole cell;
[c]n = no; y = yes YC-001 Improved the Glycosylation of the P23H Opsin Mutant Compromised transport of P23H opsin is associated with its lack of Golgi processing as a glycosylated transmembrane protein that is reflected by its shift in molecular mass differing from that of WT opsin as detected by immunoblotting (FIG. 3A, lanes 7 and 9). Upon treatment with increasing concentrations of YC-001, three bands at 50, 75 and 120 kDa emerged in immunoblots of cell lysates expressing P23H opsin (FIG. 3A, lanes 1-6). While the bands at 50 and 120 kDa were also detected in immunoblots of WT opsin and P23H opsin from cells treated with 9-cis-retinal, consistent with mature glycosylated forms of opsin, the band at 75 kDa could represent an immature intermediate product of glycosylated P23H opsin dimer formed upon treatment with YC-001. Quantitatively, the total amount of P23H opsin reached a maximum when treated with 5 or 10 μM YC-001 (FIG. 3B). PNGaseF incubations confirmed that shifted molecular mass of P23H opsin by treatment of YC-001 or 9-cis-retinal was due to the improvement of glycosylation (FIG. 3C). In contrast, treatment with scriptaid does not affect the glycosylation of this mutant opsin (FIG. 3D). The glycosylation of opsin varies between cell types in which it is expressed. Here we used NIH3T3 cells to show that immature glycosylated P23H rod opsin can be further processed in cells treated with 9-cis-retinal or YC-001.

YC-001 Reversibly Binds Rod Opsin

To test whether YC-001 binds rod opsin and act as a pharmacological chaperone, a ligand-binding assay was performed using Trp fluorescence to monitor the chromophore pocket conformation in bovine opsin. Titration of opsin in the disc membranes with either 9-cis-retinal or YC-001 quenched the Trp fluorescence at 330 nm corresponding to the conformational change of Trp 265 in the chromophore pocket (FIG. 3E,F and FIG. 11) The $EC_{50}$ of YC-001 was 0.98±0.05 μM (FIG. 3f), comparable to the $EC_{50}$ of 9-cis-retinal to rod opsin at 1.20±0.10 μM (FIG. 3E). This finding suggested that YC-001 either binds to opsin in the chromophore pocket, or its allosteric binding affects the chromophore pocket conformation. In contrast, scriptaid didn't affect Trp fluorescence, suggesting that it doesn't bind to rod opsin (FIG. 3G and FIG. 10C).

To test if YC-001 is competitive with 9-cis-retinal for binding to rod opsin, pigment regeneration of opsin was monitored in ROS disc membranes by absorption spectroscopy. The peak at 495 nm was due to Schiff base linkage formation between 9-cis-retinal and the K296 in the chromophore pocket, which was used to quantify the regenerated isorhodopsin (FIG. 4a,b). An absorption at 340 nm was seen when YC-001 was dissolved in the buffer or added to rod opsin in disc membrane (FIG. 4a), suggesting that YC-001 does not form a chromophore analogue when bound to opsin. The absorption at 495 nm was reduced when an increasing concentration of YC-001 was added with 5 μM 9-cis-retinal simultaneously or sequentially to rod opsin in disc membranes (FIG. 4a and FIG. 4c), suggesting that less isorhodopsin was generated in the presence of YC-001 competing with 9-cis-retinal in a short time frame. When scriptaid and 9-cis-retinal were added simultaneously or sequentially to rod opsin in disc membranes, the absorption peak at 495 nm overlapped with that regenerated with only 9-cis-retinal (FIG. 4b), indicating that scriptaid does not compete with 9-cis-retinal in the chromophore-binding pocket.

The kinetics of isorhodopsin regeneration was traced when disc membranes were treated with YC-001 and 9-cis-retinal sequentially (FIG. 4d). An increasing concentration of YC-001 treatment didn't affect the total amount of regenerated isorhodopsin pigment at the end the reaction, but slowed down the kinetics of pigment regeneration, as demonstrated by an increase in apparent half-life.

Disc membranes were then treated either with YC-001 and 9-cis-retinal individually, simultaneously or sequentially for a total of 30 min, followed by opsin or isorhodopsin purification. The purified isorhodopsin by treatment with YC-001 and 9-cis-retinal showed a prominent absorption at 495 nm with a small shoulder at 340 nm, suggesting that most of the YC-001 was washed out during opsin/isorhodopsin purification (FIG. 11). This result confirmed that the interaction between YC-001 and opsin is reversible.

Whereas rhodopsin is quite stable, rod opsin is unstable at room temperature (RT). While aging at RT, YC-001 treated rod opsin showed a significantly longer half-life compared to that of opsin alone (FIG. 4e), suggesting YC-001 stabilizes the rod opsin structure.

To further characterize the molecular binding of YC-001 to rod opsin, we attempted to obtain the YC-001:opsin complex as a crystal structure but with little success. Using Raman spectroscopy, vibrational modes from YC-001 were clearly seen in the difference spectrum obtained by subtracting the rod opsin spectrum from the complex spectrum, in comparison to the spectrum of YC-001 in DMSO (FIG. 4f). Vibrational modes of YC-001 did not shift significantly when detected in the YC-001:opsin crystal, but these peaks were narrower than those in the free YC-001 spectrum, suggesting the non-covalent binding of YC-001 to rod opsin.

YC-001 is an Inverse Agonist and Antagonist of Rod Opsin

While acting as a pharmacological chaperone, does YC-001 binding also affect intracellular signaling of rod opsin? Here, a cAMP assay was used to address this issue (FIG. 5). In mammalian cells, heterologously expressed isorhodopsin couples to the endogenous Gi/o signaling cascade when activated by light. The NIH3T3-(WT-opsin/GFP) cells (FIG. 5a) exhibited lower cAMP level than the NIH3T3-(GFP) cells (FIG. 5b), suggesting the basal activity of rod opsin through the activated Gi/o pathway that inhibits adenylate cyclase, responsible for the synthesis of cAMP. Upon light exposure, the NIH3T3-(WT-opsin/GFP) cells treated with 9-cis-retinal showed significantly reduced cAMP level, confirming that isorhodopsin had activated Gi/o signaling (FIG. 5a). However, YC-001 treated NIH3T3-(WT-opsin/GFP) cells evidenced a dose-dependent increase in cAMP levels as compared to non-treated cells (FIG. 5b,c) with an $EC_{50}$ value of 8.22 μM, either in the dark or light, suggesting that YC-001 silences the basal activity of rod opsin. Co-treated with 1 μM 9-cis-retinal under light, YC-001 also induced a dose-dependent elevation in cAMP levels in NIH3T3-(WT-opsin/GFP) cells under light exposure (FIG. 5c), suggesting that YC-001 antagonizes the isorhodopsin formation or the photoactivation capabilities of isorhodopsin. The 9-cis-retinal dose-response curve with 40 μM YC-001 co-treatment revealed a 3-fold increase in the $EC_{50}$, and the curve shifted upward compared to the dose curve obtained by 9-cis-retinal treatment alone (FIG. 5d). Together, to our knowledge, YC-001 is the first non-retinal compound that has been revealed to have both inverse agonist and antagonist activity toward rod opsin.

To confirm the inverse agonist and antagonist activity of YC-001 toward rod opsin, the initial rate of $G_t$ activation was measured by a fluorescence change due to GTPγS uptake leading to dissociation of the Gt:opsin complex. Bovine rod opsin has a basal activity for $G_t$ activation. Upon treatment with 40 μM YC-001, the initial rate of $G_t$ activation for opsin was substantially reduced (FIG. 5e,f, black line and point, $\ln(k_{initial})=-6.1$) compared to the DMSO control group (FIG. 5e,f, grey line and point, $\ln(k_{initial})=-5.3$), confirming that YC-001 silenced the constitutive activity of rod opsin. Moreover, opsin treated with YC-014 lacking pharmacological chaperone activity (Table 2) at 40 μM also showed a slightly decreased rate of $G_t$ activation (FIG. 5e,f, blue line and point, $\ln(k_{initial})=-5.7$), which could be due to weak binding of YC-014 to rod opsin that is not sufficient to stabilize the P23H opsin mutant. When co-treated with 40 μM 9-cis-retinal and 40 μM YC-001, regenerated isorhodopsin showed a reduced rate of $G_t$ activation upon illumination (FIG. 5e,f, orange line and point, $\ln(k_{initial})=-4.9$) compared to that regenerated by 9-cis-retinal alone (FIG. 5e,f, magenta line and point, $\ln(k_{initial})=-4.6$), confirming that YC-001 antagonizes isorhodopsin coupled $G_t$ activation.

TABLE 2

Medicinal Chemistry of YC-001 with modifications linked to the $C_3$ of the furan-2(5H)-one ring (

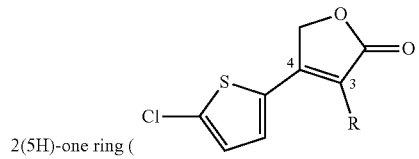

). Activities of compounds were tested with the β-Gal fragment complementation assay to quantify the rescue of P23H opsin from the ER to the plasma membrane. Activity scores were normalized to the effect of treatment with 5 μM 9-cis-retinal. Compounds with efficacies greater than 20% are listed in bold type.

| Number | Compound name | R | Molecular weight | Potency $EC_{50}$ (μM) | Efficacy (%) |
|---|---|---|---|---|---|
| 1 | YC-001 | 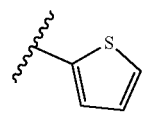 | 282.77 | 8.39 | 248 |

TABLE 2-continued

Medicinal Chemistry of YC-001 with modifications linked to the $C_3$ of the furan-2(5H)-one ring ( 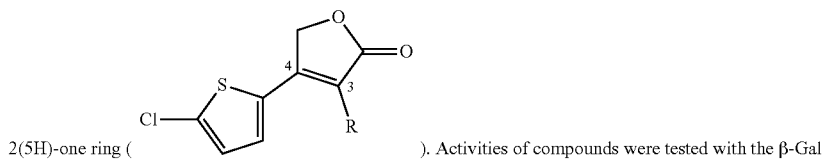 ). Activities of compounds were tested with the β-Gal fragment complementation assay to quantify the rescue of P23H opsin from the ER to the plasma membrane. Activity scores were normalized to the effect of treatment with 5 μM 9-cis-retinal. Compounds with efficacies greater than 20% are listed in bold type.

| Number | Compound name | R | Molecular weight | Potency $EC_{50}$ (μM) | Efficacy (%) |
|---|---|---|---|---|---|
| 2 | YC-051 |  | 282.77 | 10.90 | 169 |
| 3 | YC-028 | 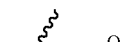 | 266.70 | NA | NA |
| 4 | YC-043 | 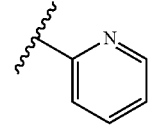 [SMILES: *c1ccccn1] | 277.73 | 19.00 | 214 |
| 5 | YC-030 | 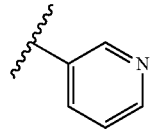 [SMILES: *c1cccnc1] | 277.73 | NA | NA |
| 6 | YC-031 | 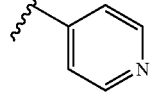 | 277.73 | NA | NA |
| 7 | YC-057 | 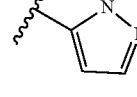 | 280.73 | NA | NA |
| 8 | YC-047 | 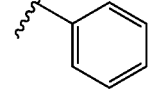 | 276.74 | 9.87 | 188 |
| 9 | YC-068 | 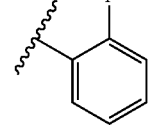 [SMILES: *c1ccccc1] | 294.73 | 5.66 | 261 |
| 10 | YC-032 | 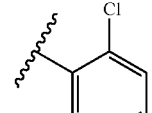 | 311.18 | 5.80 | 288 |

TABLE 2-continued

Medicinal Chemistry of YC-001 with modifications linked to the $C_3$ of the furan-2(5H)-one ring ( 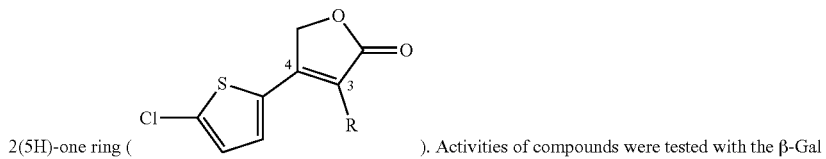 ). Activities of compounds were tested with the β-Gal fragment complementation assay to quantify the rescue of P23H opsin from the ER to the plasma membrane. Activity scores were normalized to the effect of treatment with 5 μM 9-cis-retinal. Compounds with efficacies greater than 20% are listed in bold type.

| Number | Compound name | R | Molecular weight | Potency $EC_{50}$ (μM) | Efficacy (%) |
|---|---|---|---|---|---|
| 11 | YC-013 | 2-NO₂-phenyl | 321.73 | 11.0 | 111 |
| 12 | YC-033 | 2-OMe-phenyl | 306.76 | 8.50 | 38.3 |
| 13 | YC-036 | 2-CN-phenyl | 301.75 | NA | NA |
| 14 | YC-050 | 3-F-phenyl | 294.73 | 7.36 | 131 |
| 15 | YC-034 | 3-Cl-phenyl | 311.18 | 4.75 | 43.5 |
| 16 | YC-041 | 3-OH-phenyl | 292.74 | NA | NA |
| 17 | YC-045 | 3-SO₂Me-phenyl | 354.83 | NA | NA |
| 19 | YC-053 | 4-F-phenyl | 294.73 | 24.1 | 32.9 |

TABLE 2-continued

Medicinal Chemistry of YC-001 with modifications linked to the $C_3$ of the furan-2(5H)-one ring ( 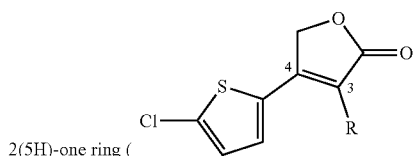 ). Activities of compounds were tested with the β-Gal fragment complementation assay to quantify the rescue of P23H opsin from the ER to the plasma membrane. Activity scores were normalized to the effect of treatment with 5 μM 9-cis-retinal. Compounds with efficacies greater than 20% are listed in bold type.

| Number | Compound name | R | Molecular weight | Potency $EC_{50}$ (μM) | Efficacy (%) |
|---|---|---|---|---|---|
| 20 | YC-027 | 4-Cl-phenyl | 311.18 | NA | NA |
| 21 | YC-023 | 4-OH-phenyl | 292.74 | NA | NA |
| 22 | YC-052 | 4-OMe-phenyl | 306.77 | 7.13 | 10 |
| 23 | YC-014 | 4-NO$_2$-phenyl | 321.73 | NA | NA |
| 24 | YC-039 | 4-CN-phenyl | 301.75 | NA | NA |
| 25 | YC-022 | 4-SO$_2$Me-phenyl | 354.83 | NA | NA |
| 26 | YC-054 | 2-Me-3-F-phenyl | 308.76 | 3.53 | 227 |
| 27 | YC-056 | 2-Cl-3-OMe-phenyl | 341.21 | 9.39 | 104 |

TABLE 2-continued

Medicinal Chemistry of YC-001 with modifications linked to the $C_3$ of the furan-2(5H)-one ring (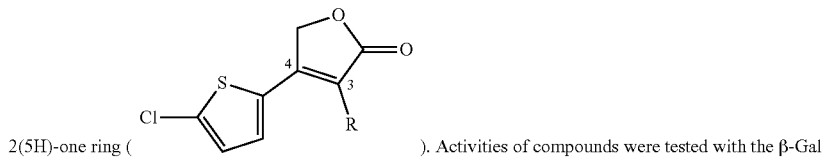). Activities of compounds were tested with the β-Gal fragment complementation assay to quantify the rescue of P23H opsin from the ER to the plasma membrane. Activity scores were normalized to the effect of treatment with 5 µM 9-cis-retinal. Compounds with efficacies greater than 20% are listed in bold type.

| Number | Compound name | R | Molecular weight | Potency $EC_{50}$ (µM) | Efficacy (%) |
|---|---|---|---|---|---|
| 28 | YC-055 | (2,4-dichlorophenyl) | 345.63 | 5.33 | 11 |

YC-001 Protects Abca4$^{-/-}$Rdh8$^{-/-}$ Mice from Retinal Damage

Due to the abundance and physiological significance of rhodopsin in ROS, its homeostasis is closely connected with photoreceptor survival. Thus, YC-001 as a pharmacological chaperone and modulator of rod opsin should also protect photoreceptors by stabilizing bleached opsin and antagonizing phototransduction activity in light-induced models of retinal degeneration. We previously developed a bright light-induced retinal degeneration model for pharmacological testing. Here, 6-week-old Abca4$^{-/-}$Rdh8$^{-/-}$ mice, a model characterized by its increased susceptibility to bright light-induced photoreceptor degeneration, were preconditioned with YC-001 at two doses: 50 or 200 mg kg$^{-1}$ body weight (bw) by intraperitoneal (i.p.) injection along with DMSO as a vehicle control. Thirty min after treatment, mice were exposed to bright light (10,000 lux) for 30 min. Seven days later, retinal structures of these mice were imaged by spectral domain-optical coherence tomography (SD-OCT) (FIG. 6a-d) and histological hematoxylin and eosin (HE) staining (FIG. 6e,f). Whereas DMSO-treated mouse retinas featured significantly diminished outer nuclear layers (ONLs) (FIG. 6a,d,f), indicating the loss of photoreceptor cells, YC-001-treated mice evidenced a dose-dependent protection of the ONL from light-induced damage (FIG. 6b-d,f). These findings demonstrate that YC-001 protects Abca4$^{-/-}$Rdh8$^{-/-}$ mice from bright light-induced retinal degeneration.

YC-001 is Detected in the Mouse Retina

A high-performance liquid chromatography (HPLC) (FIG. 7a-c) and mass spectrometry (MS) (FIG. 12) analysis was performed to determine if YC-001 can be detected in C57BL/6 mouse eyes after systemic administration. About 70 pmol per eye of YC-001 was detected at 0.5 h after i.p. injection at 200 mg kg$^{-1}$ bw, increasing to 280 pmol per eye at 3 h, and then diminishing to an undetectable level by 24 h (FIG. 7c). This result confirmed that YC-001 enters mouse eyes after systemic administration but is not retained for prolonged periods.

YC-001 does not Inhibit the Visual or Retinoid Cycle

To test if YC-001 affects the visual cycle, 11-cis-retinoid regeneration was analyzed from photobleached mice treated with YC-001 (FIG. 7d). Compared to the DMSO control group, the YC-001-treated group showed little difference in the recovery of 11-cis-retinyl oxime, suggesting that YC-001 does not affect the visual chromophore regeneration.

YC-001 does not Delay Rhodopsin Regeneration In Vivo

To determine whether YC-001 antagonizes rhodopsin signaling in vivo, the scotopic electroretinogram (ERG) recovery after bleaching was recorded in mice treated with either YC-001 or DMSO. Compared to a non-bleached age-matched control group, both YC-001- and DMSO-treated mice showed significant reductions of the initial scotopic ERG responses (FIG. 7e) followed by a linear increase of the a-wave responses over 1 hour with similar recovery rates. Considering that scotopic ERG a-wave responses directly represent a rod photoreceptors' response to light, YC-001 did not inhibit rhodopsin regeneration after bleach.

YC-001 Shows No Acute Toxicity

To test if high doses of YC-001 could cause severe toxicity, we administered YC-001 (200 and 100 mg kg$^{-1}$ bw) or DMSO to C57BL/6 mice by daily i.p. injections from Day 14 to 38 after birth. All mice survived the treatment period with no obvious behavioral or bw growth changes when comparing the YC-001-treated groups and DMSO group (FIG. 7f), suggesting virtually no acute toxicity of YC-001.

YC-001 Shows No Evidence of Mutagenicity

To assess the risk of tumorgenesis by YC-001 treatment, Ames bacterial mutation tests were performed in a total of five bacteria strains. The negative results of YC-001 in the Ames test (Table 3) suggests that YC-001 has a low risk of mutagenicity if tested in vivo.

TABLE 3

Medicinal Chemistry of YC-001 with modifications linked to $C_4$ of the furan-2(5H)-one ring ( 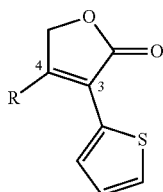 ). Activities of compounds were tested with the β-Gal fragment complementation assay to quantify the rescue of P23H opsin from the ER to the plasma membrane. Activity scores are normalized to the effect of treatment with 5 μM 9-cis-retinal. Compounds with efficacies higher than 20% are listed in bold type.

| Number | Compound name | R | Molecular weight | Potency (μM) | Efficacy (%) |
|---|---|---|---|---|---|
| 1 | YC-001 | Cl-thiophene | 282.77 | 8.39 | 248 |
| 2 | YC-021 | F-thiophene | 266.30 | 103.00 | 160 |
| 3 | YC-002 | thiophene | 248.31 | 33.00 | 6 |
| 4 | YC-049 | furan | 232.26 | 91.90 | 112 |
| 5 | YC-026 | 2-pyridyl | 243.28 | NA | NA |
| 6 | YC-046 | 4-pyridyl | 243.28 | NA | NA |
| 7 | YC-025 | cyclopropyl | 206.26 | NA | NA |
| 8 | YC-024 | hexyl | 248.34 | NA | NA |
| 9 | YC-038 | 2-Cl-phenyl | 276.74 | NA | NA |

TABLE 3-continued

Medicinal Chemistry of YC-001 with modifications linked to $C_4$ of the furan-2(5H)-one ring ( 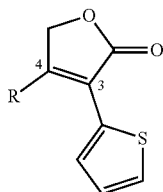 ). Activities of compounds were tested with the β-Gal fragment complementation assay to quantify the rescue of P23H opsin from the ER to the plasma membrane. Activity scores are normalized to the effect of treatment with 5 μM 9-cis-retinal. Compounds with efficacies higher than 20% are listed in bold type.

| Number | Compound name | R | Molecular weight | Potency (μM) | Efficacy (%) |
|---|---|---|---|---|---|
| 10 | YC-042 | 2-OH-phenyl | 258.29 | NA | NA |
| 11 | YC-035 | 3-F-phenyl | 260.28 | NA | NA |
| 12 | YC-048 | 3-Cl-phenyl | 276.74 | NA | NA |
| 13 | YC-040 | 3-NC-phenyl | 267.30 | NA | NA |
| 14 | YC-044 | 4-F-phenyl | 260.28 | 37.60 | 10 |
| 15 | YC-003 | 4-Cl-phenyl | 276.74 | 22.00 | 5 |
| 16 | YC-037 | 4-OMe-phenyl | 272.32 | NA | NA |

YC-001 does not Affect Cyclooxygenase 1 Activity

The furanone ring of YC-001 is also seen in the non-steroidal anti-inflammatory drugs inhibiting cyclooxygenase (COX) enzymes, thus one can argue the retinal protection of YC-001 may be due to its anti-inflammatory effects via inhibition of COX-1 that is expressed in all tissues. We measured and didn't see changes of the COX-1 enzymatic activity in the presence of up to 80 μM of YC-001 (FIG. 13).

YC-001 Showed Clearance by Phase I Hepatic Enzymes

Even though $EC_{50}$ of YC-001 is at the micromolar level in vitro, its efficacy in the $Abca4^{-/-}Rdh8^{-/-}$ mice required a higher dose of systemic administration. To address the difference of effective dosage of YC-001 in vitro and in vivo, we characterized the pharmacokinetics of YC-001 in C57BL/6 mice by i.p. injections. A first-order elimination of YC-001 was observed in the mouse plasma featured with a short half-life ($T_{1/2}$) at 34.5 min and an initial plasma concentration ($C_0$) at 7.28 µg mL$^{-1}$. Using the $T_{1/2}$ and $C_0$, we further estimated the elimination rate constant ($K_e$), the volume of distribution ($V_d$) and Clearance. The high Clearance of YC-001 at 0.552 L min$^{-1}$ kg$^{-1}$ bw was due to a high $K_e$ at 0.0201 min$^{-1}$ and a large $V_d$ at 27.5 L kg$^{-1}$ bw (FIG. 14). While the large $V_d$ is due to the hydrophobicity of YC-001, the high elimination rate constant suggests a high rate of metabolism or secretion by the liver and kidney. Indeed, by measuring the stability of this compound in isolated mouse and human liver microsomes, we found that YC-001 has an even higher initial clearance compared to the fast clearance drug, verapamil (FIG. 15). The main metabolite of YC-001 showed an increased molecular mass by 16, suggesting the addition of an oxygen atom to YC-001.

YC-001 Rescues Multiple Rod Opsin Mutants in adRP

To test if YC-001 rescues other rhodopsin misfolding mutations than the P23H, a total of six Class II mutations of human rod opsin were generated: T4R, P53R, G106R, C110Y, D190N, and P267L (FIG. 8a). NIH3T3 cells were transfected with WT or mutant opsin constructs followed by treatment with DMSO or YC-001. Cell surface immunostaining of rod opsin was imaged by fluorescence microscopy. Upon DMSO treatment, all rod opsin mutants except T4R showed dim background fluorescence, whereas immunostaining of WT-opsin and T4R opsin were clearly seen on the cell membrane (FIG. 8b). Under YC-001 treatment, cell surface staining of G106R, D190N, and P267L, but not P53 or C110Y mutants increased significantly (FIG. 8b). Differences in YC-001's efficacy between each mutant could reflect variations between their folding defects. Residues P23, G106 and D190 are located on the extracellular/intradiscal side of the rhodopsin structure surrounding the anti-parallel β-plug of the retinal binding pocket, and YC-001 was able to rescue the transport in these mutants. Residues P53, and P267 are located on the transmembrane helixes, but only P267L with its sidechain facing towards the chromophore binding pocket was rescued by YC-001. Residue C110 forms the only disulfide bond of rhodopsin with C187, which is essential to stabilize the entire structure of the protein, and YC-001 was not effective for this mutant.

Varying efficacies of YC-001 among these six Class II mutants suggest that the structural stability defects among Class II mutations differ and may require different small molecule chaperones for their stabilization.

Medicinal Chemistry of YC-001

To improve its efficacy, potency, and solubility, a medicinal chemistry study of YC-001-related compounds was undertaken. YC-001 analogs obtained from commercial vendors or by customized synthesis were denoted as YC-002 to YC-063. YC-001 has three chemical moieties (FIG. 1c): I, a 2-chlorothiophene ring; II, a furan-2(5H)-one ring; and III, a thiophene ring. Each of these moieties was modified individually. Activities of YC compounds in rescuing P23H opsin transport were then tested with the β-Gal fragment complementation assay (Tables 2-5). Changes in moiety III were better tolerated and retained the activity as pharmacological chaperones of opsin (Table 2), whereas moieties II and I were more resistant to changes (Tables 3 and 4), except for some activity that remained in YC-002, YC-021, and YC-049 (Table 3). Notably, among compounds modified in moiety III, activity was preserved or improved by substitutions with 3-thiophene (YC-051), a phenyl ring (YC-047), or 2-pyridine (YC-043), whereas substitution with furan (YC-028) failed to retain activity. Among phenyl substitutions derived from YC-047, ortho-modifications on the phenyl ring retained relatively higher efficacies (YC-068, YC-032, YC-013, and YC-033), whereas the corresponding meta-modifications displayed lower efficacies (YC-050 and YC-034), and para-modifications had little efficacy (YC-053). Substitutions on the phenyl ring of YC-047 favored the sequence —F=—Cl>—NO$_2$>—OMe, if modified at the same position. Interestingly, the pyridine substitutions of moiety III also revealed that activity was preserved with 2-pyridine (YC-047) but not 3- or 4-pyridine (YC-030 or YC-031). In summary, we hypothesize that moieties II and I of YC-001 bind in a small region of the opsin pocket, allowing only minor changes, whereas moiety III resides in a relatively larger part of the binding pocket, thereby tolerating a larger spectrum of modifications. The S atom in moiety III might interact with opsin. The medicinal chemistry study of YC-001 also yielded four active compounds with improved potency, efficacy, or solubility (YC-043, YC-068, YC-032, and YC-054). These compounds might be especially useful for further crystallography and in vivo studies.

TABLE 4

Medicinal Chemistry of YC-001 with modifications of the furan-2(5H)-one ring. Activities of the compounds were tested with the β-Gal fragment complementation assay to quantify the rescue of P23H opsin from the ER to the plasma membrane. Activity scores were normalized to the effect of treatment with 5 µM 9-cis-retinal. Only YC-001 showed an efficacy higher than 20% and is listed in bold type.

| Compound Number | name | Scaffold | R | Molecular weight | Potency (µM) | Efficacy (%) |
|---|---|---|---|---|---|---|
| 1 | YC-001 | | | 282.77 | 8.39 | 248 |

TABLE 4-continued

Medicinal Chemistry of YC-001 with modifications of the furan-2(5H)-one ring. Activities of the compounds were tested with the β-Gal fragment complementation assay to quantify the rescue of P23H opsin from the ER to the plasma membrane. Activity scores were normalized to the effect of treatment with 5 μM 9-cis-retinal. Only YC-001 showed an efficacy higher than 20% and is listed in bold type.

| Compound Number | Compound name | Scaffold | R | Molecular weight | Potency (μM) | Efficacy (%) |
|---|---|---|---|---|---|---|
| 2 | YC-060 | 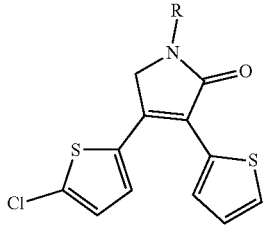 |  | 281.78 | 24.6 | 7.1 |
| 3 | YC-058 | 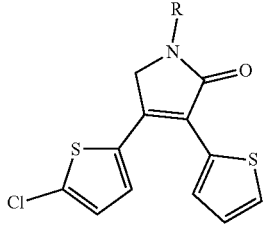 |  | 295.81 | NA | NA |
| 4 | YC-063 | 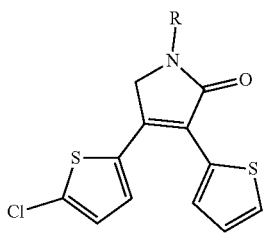 |  | 323.864 | NA | NA |
| 5 | YC-059 | 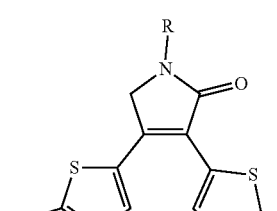 | 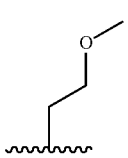 [SMILES: *CCOC] | 339.86 | NA | NA |
| 6 | YC-062 | 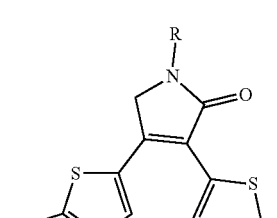 | 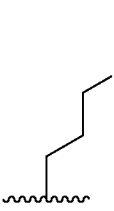 | 353.89 | NA | NA |
| 7 | YC-066 | 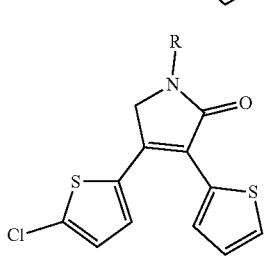 | 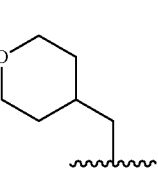 | 379.928 | NA | NA |

TABLE 4-continued

Medicinal Chemistry of YC-001 with modifications of the furan-2(5H)-one ring. Activities of the compounds were tested with the β-Gal fragment complementation assay to quantify the rescue of P23H opsin from the ER to the plasma membrane. Activity scores were normalized to the effect of treatment with 5 μM 9-cis-retinal. Only YC-001 showed an efficacy higher than 20% and is listed in bold type.

| Number | Compound name | Scaffold | R | Molecular weight | Potency (μM) | Efficacy (%) |
|---|---|---|---|---|---|---|
| 8 | YC-064 | | H— | 283.755 | NA | NA |
| 9 | YC-065 | | (methyl) | 297.782 | NA | NA |
| 10 | YC-067 | | (benzyl) | 373.88 | NA | NA |
| 11 | YC-069 | | (cyclopropylmethyl) | 337.84 | NA | NA |
| 12 | YC-061 | | (N-methylmaleimide) | 304.75 | NA | NA |

TABLE 5

Medicinal chemistry of YC-001 with more than one site modified. Activities of compounds were tested with the β-Gal fragment complementation assay to quantify the rescue of P23H opsin from the ER to the plasma membrane. Activity scores are normalized to the effect of treatment with 5 μM 9-cis-retinal. Only YC-001 showed an efficacy higher than 20% and is listed in bold type.

| Number | Compound name | Scaffold | Rs | Molecular weight | Potency (μM) | Efficacy (%) |
|---|---|---|---|---|---|---|
| 1 | YC-001 | | | 282.77 | 8.39 | 248 |

TABLE 5-continued

Medicinal chemistry of YC-001 with more than one site modified. Activities of compounds were tested with the β-Gal fragment complementation assay to quantify the rescue of P23H opsin from the ER to the plasma membrane. Activity scores are normalized to the effect of treatment with 5 μM 9-cis-retinal. Only YC-001 showed an efficacy higher than 20% and is listed in bold type.

| Number | Compound name | Scaffold | Rs | Molecular weight | Potency (μM) | Efficacy (%) |
|---|---|---|---|---|---|---|
| 2 | YC-009 | furanone scaffold with $R_1$ at 4, $R_2$ at 3 | 5-Br-thiophen-2-yl; 4-F-phenyl | 339.18 | 7.20 | 10 |
| 3 | YC-011 | furanone scaffold with $R_1$ at 4, $R_2$ at 3 | 5-Br-thiophen-2-yl; 4-Cl-phenyl | 355.63 | 7.50 | 10 |
| 4 | YC-008 | furanone scaffold with $R_1$ at 4, $R_2$ at 3 | 5-Br-thiophen-2-yl; 3,4-diCl-phenyl | 390.07 | 25.00 | 11 |
| 5 | YC-016 | succinic anhydride with thiophen-2-yl substituent | — | 182.19 | NA | NA |
| 6 | YC-018 | succinic anhydride with two (2,4,5-trimethylthiophen-3-yl) substituents | — | 348.48 | 138.00 | 95 |

This example shows, YC-001, a non-retinoid ligand of rod opsin rescued the transport and glycosylation of the P23H rod opsin mutant in mammalian cells. Significantly, YC-001 binds rod opsin non-covalently without regulation by light. Because regeneration of rhodopsin involves covalent bond formation, whereas YC-001 binds to opsin non-covalently, the total amount of regenerated rhodopsin will not be affected by YC-001 treatment if given sufficient time. Therefore, this observation can explain why there is no additive effect when YC-001 was co-treated with 9-cis-retinal (FIG. 1g). In this manner, the pharmacological chaperone activity of YC-001 could stabilize the P23H opsin both during its biosynthesis and after the mutant opsin has been bleached in the ROS discs. In contrast, for the other active compound scriptaid that also increases the transport of P23H opsin to the plasma membrane, there is no evidence to show that it binds to rod opsin. First, scriptaid does not affect the fluorescence of Trp265 in rod opsin; second, scriptaid does not compete with 9-cis-retinal for isorhodopsin regeneration; third, scriptaid does not affect the glycosylation of P23H opsin; and finally, the synergy between scriptaid and YC-001 on the transport of P23H opsin suggests different mechanisms of actions between the two molecules. Scriptaid as a histone deacetylase inhibitor, affected a total of 6% of the entire transcriptome. Rather than directly binding to rod opsin, scriptaid may improve P23H opsin transport through transcriptional regulation of multiple pathways including cytoskeleton dynamics, proteolysis, and vesicle transport.

Slowing the visual cycle has shown therapeutic potential for Stargardt disease, which lacks a functional all-trans-retinal flippase, ABCA4. Different from previously developed modulators of retinoid cycle components, YC-001 can slow the regeneration of rhodopsin and thus reduce all-trans-retinal production stimulated by light. We found that just a single dose of YC-001 protected the retinas of $Abca4^{-/-}$ $Rdh8^{-/-}$ mice from bright light-induced retinal degeneration. Lacking ABCA4 and retinol dehydrogenase 8 (RDH8), these double knockout mice have defects in clearing all-trans-retinal released from photobleached rhodopsin, thereby making photoreceptors vulnerable to bright light-damage due to all-trans-retinal's acute cytotoxicity. The protection observed with YC-001 is likely due to its antagonistic activity that competes with 11-cis-retinal for pigment regeneration and phototransduction. Because YC-001 binds to rod opsin reversibly, whereas 11-cis-retinal binds and forms a Schiff base linkage with rod opsin, competition between the two molecules should ultimately favor the latter. Therefore, we observed competition between YC-001 and 9-cis-retinal for opsin binding in mammalian cells (over a 15 to 30 min period), but not a reduction of 11-cis-retinyl oxime released from dark-adapted bleached retinas treated with YC-001 relative to the DMSO control group (timeframe in hours), or any scotopic ERG changes manifested upon YC-001 treatment. The retinal protection of Abca4$^{-/-}$ Rdh8$^{-/-}$ mice suggests a therapeutic potential for YC-001 in light-induced retinal degenerations.

From the above description of the invention, those skilled in the art will perceive improvements, changes and modifications. Such improvements, changes and modifications within the skill of the art are intended to be covered by the appended claims. All references, publications, and patents cited in the present application are herein incorporated by reference in their entirety.

What is claimed is:

1. A compound having formula (I);

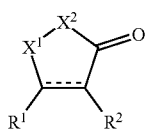

(I)

wherein $X^1$ is $CH_2$, C=O, or N—$R^3$;

wherein $X^2$ is O or N—$R^4$;

wherein at least one of $X^1$ is not N—$R^3$ or $X^2$ is not N—$R^4$;

wherein $R^1$ and $R^2$ are each independently selected from the group consisting of hydrogen, a substituted or unsubstituted cycloalkyl, heterocyclyl, aryl, and heteroaryl, wherein at least one of $R^1$ or $R^2$ is a substituted or unsubstituted thiophene;

wherein $R^3$ and $R^4$ are each independently selected from the group consisting of hydrogen, a substituted or unsubstituted $C_1$-$C_{24}$ alkyl, $C_2$-$C_{24}$ alkenyl, $C_2$-$C_{24}$ alkynyl, $C_3$-$C_{20}$ aryl, heteroaryl, heterocycloalkenyl containing from 5-6 ring atoms (wherein from 1-3 of the ring atoms is independently selected from N, NH, N($C_1$-$C_6$ alkyl), NC(O)($C_1$-$C_6$ alkyl), O, and S), $C_6$-$C_{24}$ alkaryl, $C_6$-$C_{24}$ aralkyl, halo, —Si($C_1$-$C_3$ alkyl)$_3$, hydroxyl, sulfhydryl, $C_1$-$C_{24}$ alkoxy, $C_2$-$C_{24}$ alkenyloxy, $C_2$-$C_{24}$ alkynyloxy, $C_5$-$C_{20}$ aryloxy, acyl, acyloxy, $C_2$-$C_{24}$ alkoxycarbonyl, $C_6$-$C_{20}$ aryloxycarbonyl, $C_2$-$C_{24}$ alkylcarbonato, $C_6$-$C_{20}$ arylcarbonato, carboxy, carboxylato, carbamoyl, $C_1$-$C_{24}$ alkyl-carbamoyl, aryl-carbamoyl, thiocarbamoyl, carbamido, cyano, isocyano, cyanato, isocyanato, isothiocyanato, azido, formyl, thioformyl, amino, $C_1$-$C_{24}$ alkyl amino, $C_5$-$C_{20}$ aryl amino, $C_2$-$C_{24}$ alkylamido, $C_6$-$C_{20}$ arylamido, imino, alkylimino, arylimino, nitro, nitroso, sulfo, sulfonato, $C_1$-$C_{24}$ alkylsulfanyl, arylsulfanyl, $C_1$-$C_{24}$ alkylsulfinyl, $C_5$-$C_{20}$ arylsulfinyl, $C_1$-$C_{24}$ alkylsulfonyl, $C_5$-$C_{20}$ arylsulfonyl, phosphono, phosphonato, phosphinato, phospho, or phosphino or combinations thereof;

and pharmaceutically acceptable salts thereof.

2. A compound having formula (III):

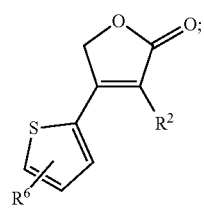

(III)

wherein $R^2$ and $R^6$ are each individually hydrogen, a substituted or unsubstituted $C_1$-$C_{24}$ alkyl, $C_2$-$C_{24}$ alkenyl, C$_2$-C$_{24}$ alkynyl, C$_3$-C$_{20}$ aryl, heteroaryl, heterocycloalkenyl containing from 5-6 ring atoms (wherein from 1-3 of the ring atoms is independently selected from N, NH, N(C$_1$-C$_6$ alkyl), NC(O)(C$_1$-C$_6$ alkyl), O, and S), C$_6$-C$_{24}$ alkaryl, C$_6$-C$_{24}$ aralkyl, halo, —Si(C$_1$-C$_3$ alkyl)$_3$, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl, acyloxy, C$_2$-C$_{24}$ alkoxycarbonyl, C$_6$-C$_{20}$ aryloxycarbonyl, C$_2$-C$_{24}$ alkylcarbonato, C$_6$-C$_{20}$ arylcarbonato, carboxy, carboxylato, carbamoyl, C$_1$-C$_{24}$ alkyl-carbamoyl, arylcarbamoyl, thiocarbamoyl, carbamido, cyano, isocyano, cyanato, isocyanato, isothiocyanato, azido, formyl, thioformyl, amino, C$_1$-C$_{24}$ alkyl amino, C$_5$-C$_{20}$ aryl amino, C$_2$-C$_{24}$ alkylamido, C$_6$-C$_{20}$ arylamido, imino, alkylimino, arylimino, nitro, nitroso, sulfo, sulfonato, C$_1$-C$_{24}$ alkylsulfanyl, arylsulfanyl, C$_1$-C$_{24}$ alkylsulfinyl, C$_5$-C$_{20}$ arylsulfinyl, C$_1$-C$_{24}$ alkylsulfonyl, C$_5$-C$_{20}$ arylsulfonyl, phosphono, phosphonato, phosphinato, phospho, or phosphino or combinations thereof;

and pharmaceutically acceptable salts thereof.

3. A compound having formula (IV):

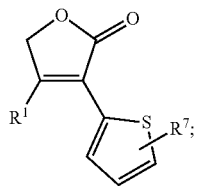

(IV)

wherein R$^1$ and R$^7$ are each individually hydrogen, a substituted or unsubstituted C$_1$-C$_{24}$ alkyl, C$_2$-C$_{24}$ alkenyl, C$_2$-C$_{24}$ alkynyl, C$_3$-C$_{20}$ aryl, heteroaryl, heterocycloalkenyl containing from 5-6 ring atoms (wherein from 1-3 of the ring atoms is independently selected from N, NH, N(C$_1$-C$_6$ alkyl), NC(O)(C$_1$-C$_6$ alkyl), O, and S), C$_6$-C$_{24}$ alkaryl, C$_6$-C$_{24}$ aralkyl, halo, —Si(C$_1$-C$_3$ alkyl)$_3$, hydroxyl, sulfhydryl, C$_1$-C$_{24}$ alkoxy, C$_2$-C$_{24}$ alkenyloxy, C$_2$-C$_{24}$ alkynyloxy, C$_5$-C$_{20}$ aryloxy, acyl, acyloxy, C$_2$-C$_{24}$ alkoxycarbonyl, C$_6$-C$_{20}$ aryloxycarbonyl, C$_2$-C$_{24}$ alkylcarbonato, C$_6$-C$_{20}$ arylcarbonato, carboxy, carboxylato, carbamoyl, C$_1$-C$_{24}$ alkyl-carbamoyl, arylcarbamoyl, thiocarbamoyl, carbamido, cyano, isocyano, cyanato, isocyanato, isothiocyanato, azido, formyl, thioformyl, amino, C$_1$-C$_{24}$ alkyl amino, C$_5$-C$_{20}$ aryl amino, C$_2$-C$_{24}$ alkylamido, C$_6$-C$_{20}$ arylamido, imino, alkylimino, arylimino, nitro, nitroso, sulfo, sulfonato, C$_1$-C$_{24}$ alkylsulfanyl, arylsulfanyl, C$_1$-C$_{24}$ alkylsulfinyl, C$_5$-C$_{20}$ arylsulfinyl, C$_1$-C$_{24}$ alkylsulfonyl, C$_5$-C$_{20}$ arylsulfonyl, phosphono, phosphonato, phosphinato, phospho, or phosphino or combinations thereof;

and pharmaceutically acceptable salts thereof.

4. The compound of claim 1, wherein R$^3$ and R$^4$ are each independently selected from the group consisting of hydrogen, a substituted or unsubstituted C$_1$-C$_{24}$ alkyl, a substituted or unsubstituted cycloalkyl, heterocyclyl, aryl, and heteroaryl.

5. The compound of claim 1, wherein the compound is selected from the group consisting of:

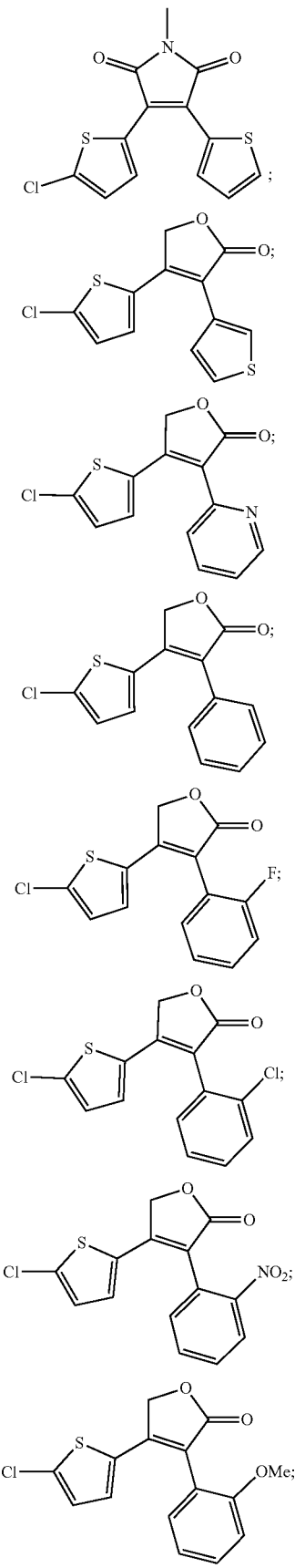

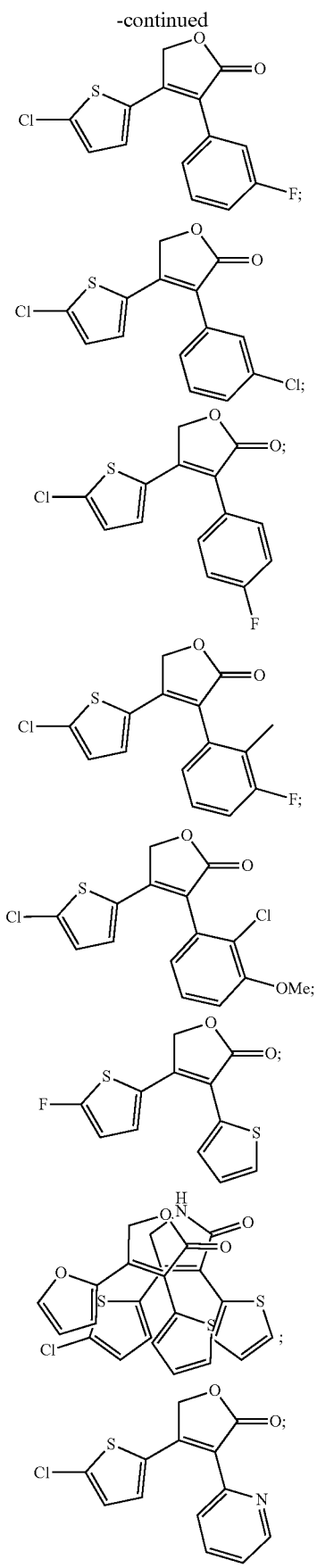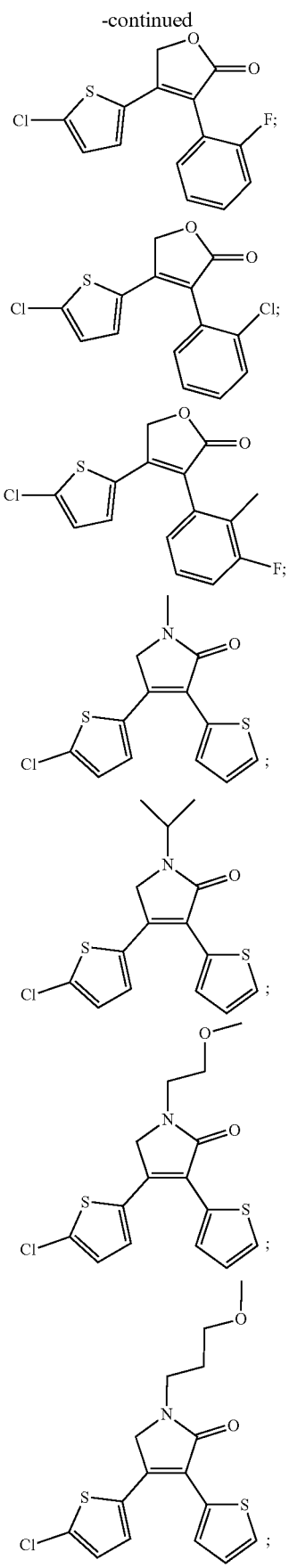

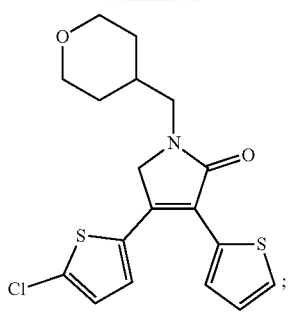
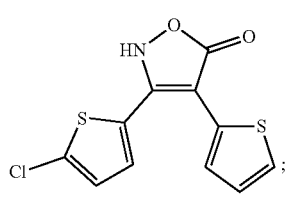
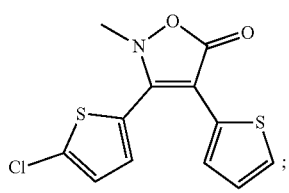
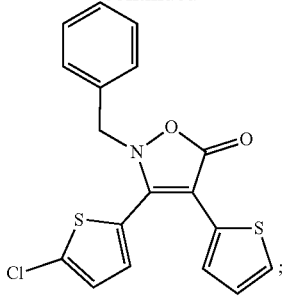
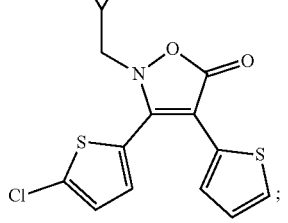
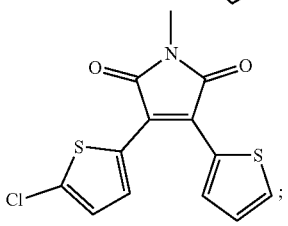
and pharmaceutically acceptable salts thereof.
* * * * *

SEQUENCE LISTING

```
Sequence total quantity: 13
SEQ ID NO: 1            moltype = AA   length = 9
FEATURE                 Location/Qualifiers
REGION                  1..9
                        note = Synthetic Construct
source                  1..9
                        mol_type = protein
                        organism = synthetic construct
SEQUENCE: 1
TETSQVAPA                                                                          9

SEQ ID NO: 2            moltype = DNA  length = 31
FEATURE                 Location/Qualifiers
source                  1..31
                        mol_type = other DNA
                        organism = Homo sapiens
SEQUENCE: 2
atgaatggca gagaaggccc taacttctac g                                                 31

SEQ ID NO: 3            moltype = DNA  length = 31
FEATURE                 Location/Qualifiers
source                  1..31
                        mol_type = other DNA
                        organism = Homo sapiens
SEQUENCE: 3
cgtagaagtt agggccttct ctgccattca t                                                 31

SEQ ID NO: 4            moltype = DNA  length = 29
FEATURE                 Location/Qualifiers
source                  1..29
                        mol_type = other DNA
                        organism = Homo sapiens
SEQUENCE: 4
gctgggcttc cgcatcaact tcctcacgc                                                    29

SEQ ID NO: 5            moltype = DNA  length = 29
FEATURE                 Location/Qualifiers
source                  1..29
                        mol_type = other DNA
                        organism = Homo sapiens
SEQUENCE: 5
gcgtgaggaa gttgatgcgg aagcccagc                                                    29

SEQ ID NO: 6            moltype = DNA  length = 31
FEATURE                 Location/Qualifiers
source                  1..31
                        mol_type = other DNA
                        organism = Homo sapiens
SEQUENCE: 6
ggatacttcg tcttcaggcc cacaggatgc a                                                 31

SEQ ID NO: 7            moltype = DNA  length = 31
FEATURE                 Location/Qualifiers
source                  1..31
                        mol_type = other DNA
                        organism = Homo sapiens
SEQUENCE: 7
tgcatcctgt gggcctgaag acgaagtatc c                                                 31

SEQ ID NO: 8            moltype = DNA  length = 31
FEATURE                 Location/Qualifiers
source                  1..31
                        mol_type = other DNA
                        organism = Homo sapiens
SEQUENCE: 8
```

```
cgggcccaca ggatacaatt tggagggctt c                                            31

SEQ ID NO: 9           moltype = DNA   length = 31
FEATURE                Location/Qualifiers
source                 1..31
                       mol_type = other DNA
                       organism = Homo sapiens
SEQUENCE: 9
gaagccctcc aaattgtatc ctgtgggccc g                                            31

SEQ ID NO: 10          moltype = DNA   length = 32
FEATURE                Location/Qualifiers
source                 1..32
                       mol_type = other DNA
                       organism = Homo sapiens
SEQUENCE: 10
gctcgtgtgg aatcaactac tacacgctca ag                                           32

SEQ ID NO: 11          moltype = DNA   length = 32
FEATURE                Location/Qualifiers
source                 1..32
                       mol_type = other DNA
                       organism = Homo sapiens
SEQUENCE: 11
cttgagcgtg tagtagttga ttccacacga gc                                           32

SEQ ID NO: 12          moltype = DNA   length = 30
FEATURE                Location/Qualifiers
source                 1..30
                       mol_type = other DNA
                       organism = Homo sapiens
SEQUENCE: 12
gatctgctgg gtgctctacg ccagcgtggc                                              30

SEQ ID NO: 13          moltype = DNA   length = 30
FEATURE                Location/Qualifiers
source                 1..30
                       mol_type = other DNA
                       organism = Homo sapiens
SEQUENCE: 13
gccacgctgg cgtagagcac ccagcagatc                                              30
```